United States Patent
Brister et al.

(10) Patent No.: US 8,162,969 B2
(45) Date of Patent: *Apr. 24, 2012

(54) INTRAGASTRIC DEVICE

(75) Inventors: Mark C. Brister, Encinitas, CA (US); Nelson Quintana, San Diego, CA (US); Kaushik A Patel, Poway, CA (US); Neil R. Drake, San Diego, CA (US); Antonio C. Llevares, Chula Vista, CA (US); Dubravka Markovic, San Diego, CA (US); Andrew P. Rasdal, San Diego, CA (US); Amy D. L. VandenBerg, San Diego, CA (US)

(73) Assignee: Obalon Therapeutics, Inc., Carlsbad, CA (US)

( * ) Notice: Subject to any disclaimer, the term of this patent is extended or adjusted under 35 U.S.C. 154(b) by 338 days.

This patent is subject to a terminal disclaimer.

(21) Appl. No.: 12/580,132

(22) Filed: Oct. 15, 2009

(65) Prior Publication Data

US 2010/0100117 A1    Apr. 22, 2010

Related U.S. Application Data

(60) Provisional application No. 61/105,932, filed on Oct. 16, 2008.

(51) Int. Cl.
*A61M 29/00* (2006.01)
(52) U.S. Cl. .................................. 606/196
(58) Field of Classification Search ............ 606/1, 151, 606/153, 192, 196, 197, 199; 604/270, 506, 604/539, 890.1; 128/898; 206/522; 424/453; 446/186, 213, 224; 623/2.17, 2.18, 1.26
See application file for complete search history.

(56) References Cited

U.S. PATENT DOCUMENTS

| | | | |
|---|---|---|---|
| 3,788,322 | A | 1/1974 | Michaels |
| 3,797,492 | A | 3/1974 | Place |
| 4,133,315 | A | 1/1979 | Berman et al. |
| 4,234,454 | A | 11/1980 | Strope |
| 4,236,521 | A | 12/1980 | Lauterjung |

(Continued)

FOREIGN PATENT DOCUMENTS

DE    3540936    10/1986

(Continued)

OTHER PUBLICATIONS

Al Kahtani et al., Bio-Enteric Intragastric Balloon In Obese Patients: A Retrospective Analysis Of King Faisal Specialist Hospital Experience; Obes Surg; Aug. 28, 2008.

(Continued)

*Primary Examiner* — Kevin T Truong
(74) *Attorney, Agent, or Firm* — Knobbe Martens Olson & Bear LLP

(57) ABSTRACT

An implant configured for ingestion by a patient. After the implant has been swallowed by the patient and is disposed within the target location, e.g. the patient's stomach, an inflation subcomponent causes the implant to expand from a compact delivery state to an expanded, volume-occupying, deployed state. In the deployed state the implant creates a sensation of satiety in the patient stomach and thereby aids in limiting food intake and obesity. After a predetermined time a deflation subcomponent is actuated and the implant reduces in size so as to allow it to pass through the remainder of the patient's digestive track. The device may further incorporate tracking and visualization subcomponents, as well as pharmaceutical delivery subcomponents.

26 Claims, 45 Drawing Sheets

U.S. PATENT DOCUMENTS

| | | | |
|---|---|---|---|
| 4,246,893 A | 1/1981 | Berson |
| 4,416,267 A | 11/1983 | Garren et al. |
| 4,485,805 A | 12/1984 | Foster, Jr. |
| 4,517,979 A | 5/1985 | Pecenka |
| 4,560,392 A | 12/1985 | Basevi |
| 4,607,618 A | 8/1986 | Angelchik |
| 4,694,827 A | 9/1987 | Weiner et al. |
| 4,723,547 A | 2/1988 | Kullas et al. |
| 4,739,758 A | 4/1988 | Lai et al. |
| 4,812,315 A | 3/1989 | Tarabishi |
| 4,813,934 A | 3/1989 | Engelson et al. |
| 4,857,029 A | 8/1989 | Dierick et al. |
| 4,899,747 A | 2/1990 | Garren et al. |
| 4,917,885 A | 4/1990 | Chiba et al. |
| 4,925,446 A | 5/1990 | Garay et al. |
| 4,929,214 A | 5/1990 | Lieberman |
| 5,049,106 A | 9/1991 | Kim et al. |
| 5,084,061 A | 1/1992 | Gau et al. |
| 5,129,915 A | 7/1992 | Cantenys et al. |
| 5,234,454 A | 8/1993 | Bangs |
| 5,259,399 A | 11/1993 | Brown |
| 5,308,326 A | 5/1994 | Zimmon |
| 5,431,917 A | 7/1995 | Yamamoto et al. |
| 5,728,119 A | 3/1998 | Smith et al. |
| 5,852,889 A | 12/1998 | Rinaldi |
| 5,868,141 A | 2/1999 | Ellias |
| 5,897,205 A | 4/1999 | Sinsteden |
| 5,910,128 A | 6/1999 | Quinn |
| 6,427,089 B1 | 7/2002 | Knowlton |
| 6,454,785 B2 | 9/2002 | De Hoyos Garza |
| 6,579,301 B1 | 6/2003 | Bales et al. |
| 6,682,473 B1 | 1/2004 | Matsuura et al. |
| 6,733,512 B2 | 5/2004 | McGhan et al. |
| 6,981,980 B2 | 1/2006 | Sampson et al. |
| 6,988,983 B2 | 1/2006 | Connors et al. |
| 7,101,396 B2 * | 9/2006 | Artof et al. ............ 623/2.18 |
| 7,192,397 B2 | 3/2007 | Lewkowicz et al. |
| 7,682,306 B2 | 3/2010 | Shah |
| 7,699,863 B2 | 4/2010 | Marco et al. |
| 7,753,949 B2 * | 7/2010 | Lamphere et al. ........ 623/1.26 |
| 7,972,378 B2 * | 7/2011 | Tabor et al. ............ 623/2.17 |
| 2003/0021822 A1 | 1/2003 | Lloyd |
| 2003/0171768 A1 | 9/2003 | McGhan |
| 2004/0044351 A1 | 3/2004 | Searle |
| 2004/0186502 A1 | 9/2004 | Sampson |
| 2005/0222329 A1 | 10/2005 | Shah et al. |
| 2005/0267405 A1 | 12/2005 | Shah |
| 2006/0058829 A1 | 3/2006 | Sampson et al. |
| 2007/0100208 A1 | 5/2007 | Lewkowicz et al. |
| 2007/0104754 A1 | 5/2007 | Sterling et al. |
| 2007/0104755 A1 | 5/2007 | Sterling et al. |
| 2007/0156248 A1 | 7/2007 | Marco et al. |
| 2007/0207199 A1 | 9/2007 | Sogin et al. |
| 2007/0212559 A1 | 9/2007 | Shah |
| 2008/0051866 A1 | 2/2008 | Chen et al. |
| 2008/0172079 A1 | 7/2008 | Birk |
| 2008/0306506 A1 | 12/2008 | Leatherman et al. |
| 2009/0182424 A1 | 7/2009 | Marco et al. |
| 2009/0192535 A1 | 7/2009 | Kasic, II et al. |
| 2009/0259246 A1 | 10/2009 | Eskaros et al. |
| 2010/0100116 A1 | 4/2010 | Brister et al. |
| 2010/0137897 A1 | 6/2010 | Brister et al. |

FOREIGN PATENT DOCUMENTS

| | | |
|---|---|---|
| EP | 0103481 | 3/1984 |
| EP | 0246999 | 11/1987 |
| JP | 62286470 | 12/1987 |
| WO | WO 87/00034 | 1/1987 |
| WO | WO 99/25418 | 5/1999 |
| WO | WO 01/68007 | 9/2001 |
| WO | WO 02/16001 | 2/2002 |
| WO | WO 02/40081 | 5/2002 |
| WO | WO 02/091961 | 11/2002 |
| WO | WO 03/055420 | 7/2003 |
| WO | WO 2004/084763 | 10/2004 |
| WO | WO 2006/020929 | 2/2006 |
| WO | WO 2007/136735 | 11/2007 |
| WO | WO 2010/045477 | 4/2010 |
| WO | WO 2010/045482 | 4/2010 |

OTHER PUBLICATIONS

Al-Momen et al., Intragastric Balloon For Obesity: A Retrospective Evaluation Of Tolerance And Efficacy; Obes Surg; 2005;15(1):101-5.

Benjamin et al., Double-Blind Controlled Trial of the Garren-Edwards Gastric Bubble: An Adjunctive Treatment for Exogenous Obesity, Gastroenterology, vol. 95, No. 3, pp. 581-588, Sep. 1988.

Carvalho et al., An Improved Intragastric Balloon Procedure Using A New Balloon: Preliminary Analysis Of Safety And Efficacy, Obes Surg, 2008.

Coskun et al., Bioenterics Intragastric Balloon: Clinical Outcomes Of The First 100 Patients-A Turkish Experience, Obes Surg, Sep. 2008; 18(9):1154-6. published online Jun. 3, 2008.

Dastis et al., Intragastric Balloon For Weight Loss: Results In 100 Individuals Followed For At Least 2.5 Years; Endoscopy. Jul. 2009; 41(7):575-80; published online Jul. 8, 2009.

De Waele et al., Endoscopic Volume Adjustment Of Intragastric Balloons For Intolerance, Obes Surg; Apr. 2001; 11(2):223-4.

Doldi et al., Treatment Of Morbid Obesity With Intragastric Balloon in Association With Diet; Obes Surg; 2002; 12(4):583-7.

Dumonceau, Evidence-Based Review Of The Bioenterics Intragastric Balloon For Weight Loss, Obes Surg. Dec. 2008;18(12):1611-7. published online Jun. 21, 2008.

Durrans et al., Comparison Of Weight Loss With Short Term Dietary And Intragastric Balloon Treatment; Gut 1989, 30, 565-568.

Eckhauser et al., Hydrostatic Balloon Dilation for Stomal Stenosis after Gastric Partitioning, Surgical Gastroenterology, vol. 3, No. 1, pp. 43-50, 1984.

European Search Report dated Feb. 21, 2008 for EP App. No. 04757774.

European Search Report dated Jun. 22, 2010 for EP App. No. 10004281.1 filed Mar. 17, 2004.

European Search Report dated Sep. 14, 2009 for EP App. No. 05786479 filed Aug. 15, 2005.

Evans et al., Intragastric Balloon In The Treatment Of Patients With Morbid Obesity, British Journal of Surgery; 2001; 88:1245-1248.

Fernandes et al., Intragastric Balloon For Obesity (Review); Cochrane Review; Jan. 24, 2007; Issue 1.

Forestieri et al., Heliosphere Bag In The Treatment of Severe Obesity: Preliminary Experience, Obes Surg; May 2006; 16(5):635-7.

Gaggiotti et al., Adjustable Totally Implanted Intragastric Prosthesis (ATIIP). Endogast for Treatment Of Morbid Obesity: One Year Follow-Up Of A Multicenter Prospective Clinical Survey; Obesity Surgery. 2007: 17, 949-956.

Geliebter et al., Gastric balloon to treat obesity: a double-blind study in nondieting subjects, The American Journal of Clinical Nutrition, vol. 51, pp. 584-588, 1990.

Genco et al., Bioenterics Intragastric Balloon (BIB): A Short-Term, Double-Blind, Randomized, Controlled, Crossover Study On Weight Reduction In Morbidly Obese Patients; International Journal of Obesity (Lond); Jan. 2006; 30(1):129-33; published online Sep. 27, 2005.

Genco et al., Bioenterics Intragastric Balloon: The Italian Experience With 2,515 Patients; Obes Surg; 2005: 15(8):1161-4.

Genco et al., Intragastric Balloon or Diet Alone? A Retrospective Evaluation, Obes Surg, Aug. 2008; 18(8):989-92. published online May 16, 2008.

Genco et al., Laparoscopic Sleeve Gastrectomy Versus Intragastric Balloon: A Case-Control Study, Surg Endosc. Springer Science & Business Media, published online Jan. 24, 2009.

Gottig et al., Analysis Of Safety And Efficacy Of Intragastric Balloon in Extremely Obese Patients, Obes Surg, Jun. 2009; 19(6):677-83. published online Mar. 17, 2009.

Imaz et al., Safety And Effectiveness Of The Intragastric Balloon For Obesity. A Meta-Analysis; Obes Surg; Jul. 2008;18(7):841-6; published online May 6, 2008.

International Preliminary Report on Patentability dated Dec. 1, 2005 for PCT/US2004/008178 file Mar. 17, 2004.

International Preliminary Report on Patentability dated Jan. 13, 2009 for PCT/US2008/028850 filed Aug. 15, 2005.

International Search Report and Written Opinion dated Oct. 15, 2004 for PCT/US2004/08178 filed Mar. 17, 2004.

International Search Report dated Jul. 8, 2010 for PCT/US2009/060881 filed Oct. 15, 2009.

International Search Report dated Jun. 25, 2008 for PCT/US2005/28850 filed Aug. 15, 2005.

International Search Report dated May 26, 2010 for PCT/US2009/060874 filed Oct. 15, 2009.

Langer, R., Drug delivery and targeting, Nature, Suuplement to vol. 392, No. 6679, pp. 5-10, Apr. 1998.

Malik; Endoluminal And Transluminal Surgery: Current Status And Future Possibilities; Surgical Endoscopy; 2006; 20(8):1179-92.

Martin et al., Safety of the Ullorex Oral Intragastric Balloon for the Treatment of Obesity, Journal of Diabetic Science and Technology, vol. 1, Issue 4, pp. 574-581, Jul. 2007.

Mathus-Vliegen et al., Intragastric Ballon in the Treatment of Super-morbid Obesity—Double-Blind, Sham-Controlled, Crossover Evaluation of 500-Milliliter Balloon, Gastroenterology, vol. 99, No. 2, pp. 362-369, Aug. 1990.

Melissas et al., The Intragastric Balloon—Smoothing The Path To Bariatric Surgery, Obes Surg 2006; 16:897-902.

Mion et al., Tolerance And Efficacy Of An Air-Filled Balloon In Non-Morbidly Obese Patients: Results Of A Prospective Multicenter Study; Obes Surg; Jul. 2007; 17(7):764-769.

Nieben et al., Ingtragastric Balloon as an Artificial Bezoar for Treatment of Obesity, The Lancet, vol. 1, No. 8265, pp. 198-199, Jan. 1982.

Ramhamadany et al, Effect Of The Gastric Balloon Versus Sham Procedure On Weight Loss In Obese Subjects; Gut 1989; 30; 1054-1057.

Rodriguez-Hermosa et al., Gastric Necrosis: A Possible Complication Of The Use Of The Intragastric Balloon In A Patient Previously Submitted To Nissen Fundoplication; Obes Surg; 19:1456-1459; published online Jun. 9, 2009.

Roman et al., Intragastric Balloon For "Non-Morbid" Obesity: A Retrospective Evaluation Of Tolerance And Efficacy; Obes Surg; Apr. 2004; 14(4):539-44.

Sallet et. al. Brazilian Multicenter Study of the Intragastric Balloon; Obesity Surgery; Aug. 2004; 14(7); 991-998.

Totte et al., Weight Reduction By Means Of Intragastric Device: Experience With The Bioenterics Intragastric Balloon; Obes Surg; Aug. 2001; 11(4):519-23.

Trande et al., Efficacy, Tolerance And Safety of New Intragastric Air-Filled Balloon (Heliosphere Bag) For Obesity: The Experience Of 17 Cases; Obes Surg; Dec. 10, 2008.

Vansonnenberg et al., Percutaneous Gastrostomy: Use of Intragastric Ballon Support, Radiology, vol. 152, No. 2, pp. 531-532, Aug. 1984.

Wahlen et al., The Bioenterics Intragastric Balloon (BIB): How to Use It; Obes Surg; 2001;11(4):524-7.

* cited by examiner

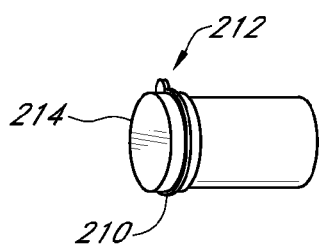  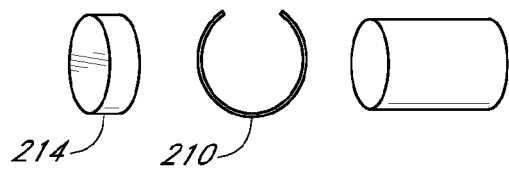
FIG. 17A          FIG. 17B
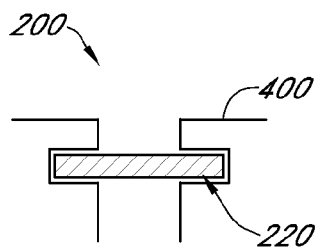 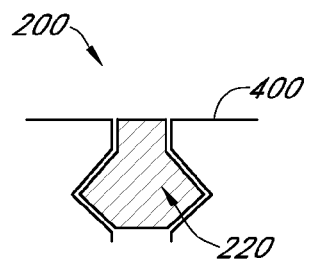
FIG. 18          FIG. 19

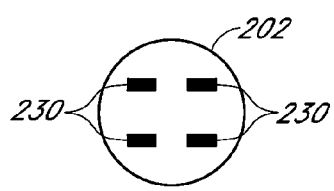
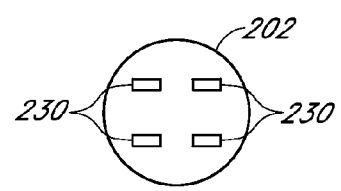
FIG. 20A         FIG. 20B
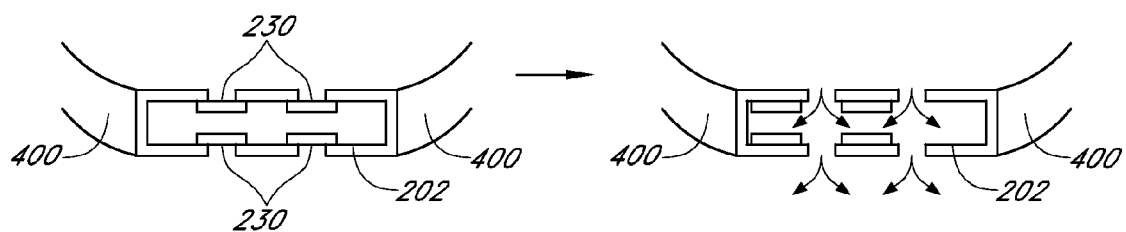
FIG. 20C         FIG. 20D

INTRAGASTRIC DEVICE

CROSS-REFERENCE TO RELATED APPLICATIONS

This application claims priority under 35 U.S.C. §119(e) to U.S. Provisional Application No. 61/105,932, filed Oct. 16, 2008, the contents of which is hereby incorporated by reference herein in its entirety and is hereby made a portion of this specification.

FIELD OF THE INVENTION

The preferred embodiments relate to devices and methods for treating obesity. More particularly, the present invention is related to intragastric devices and methods of fabricating, deploying, monitoring, and retrieving thereof.

BACKGROUND OF THE INVENTION

Obesity is a major health problem in developed countries. Obesity puts you at greater risk of developing high blood pressure, diabetes and many other serious health problems. In the United States, the complications of overweight and obesity are estimated to affect nearly one in three American adults, with an annual medical cost of over $80 billion and, including indirect costs such as lost wages, a total annual economic cost of over $120 billion. Except for rare pathological conditions, weight gain is directly correlated to overeating.

Noninvasive methods for reducing weight include increasing metabolic activity to burn calories and/or reducing caloric intake, either by modifying behavior or with pharmacological intervention to reduce the desire to eat. Other methods include surgery to reduce the stomach's volume, banding to limit the size of the stoma, and intragastric devices that reduce the desire to eat by occupying space in the stomach.

Intragastric volume-occupying devices provide the patient a feeling of satiety after having eaten only small amounts of food. Thus, the caloric intake is diminished while the subject is satisfied with a feeling of fullness. Currently available volume-occupying devices have many shortcomings. For example, complex gastric procedures are required to insert some devices.

U.S. Pat. No. 4,133,315, the contents of which are incorporated herein by reference, discloses an apparatus for reducing obesity comprising an inflatable, elastomeric bag and tube combination. The bag can be inserted into the patient's stomach by swallowing. The end of the attached tube distal to the bag remains in the patient's mouth. A second tube is snaked through the nasal cavity and into the patient's mouth. The tube ends located in the patient's mouth are connected to form a continuous tube for fluid communication through the patient's nose to the bag. Alternatively, the bag can be implanted by a gastric procedure. The bag is inflated through the tube to a desired degree before the patient eats so that the desire for food is reduced. After the patient has eaten, the bag is deflated. The tube extends out of the patient's nose or abdominal cavity throughout the course of treatment.

U.S. Pat. Nos. 5,259,399, 5,234,454 and 6,454,785, the contents of which are incorporated herein by reference, disclose intragastric volume-occupying devices for weight control that must be implanted surgically.

U.S. Pat. Nos. 4,416,267; 4,485,805; 4,607,618; 4,694,827; 4,723,547; 4,739,758; 4,899,747 and European Patent No. 246,999, the contents of which are incorporated herein by reference, relate to intragastric, volume-occupying devices for weight control that can be inserted endoscopically. Of these, U.S. Pat. Nos. 4,416,267; 4,694,827; 4,739,758 and 4,899,747 relate to balloons whose surface is contoured in a certain way to achieve a desired end. In U.S. Pat. Nos. 4,416,267 and 4,694,827, the balloon is torus-shaped with a flared central opening to facilitate passage of solids and liquids through the stomach cavity. The balloon of U.S. Pat. No. 4,694,827 has a plurality of smooth-surfaced convex protrusions. The protrusions reduce the amount of surface area which contacts the stomach wall, thereby reducing the deleterious effects resulting from excessive contact with the gastric mucosa. The protrusions also define channels between the balloon and stomach wall through which solids and liquids may pass. The balloon of U.S. Pat. No. 4,739,758 has blisters on its periphery that prevent it from seating tightly against the cardia or pylorus.

The balloons of U.S. Pat. Nos. 4,899,747 and 4,694,827, are inserted by pushing the deflated balloon and releasably attached tubing down a gastric tube. U.S. Pat. No. 4,723,547 discloses a specially adapted insertion catheter for positioning its balloon. In U.S. Pat. No. 4,739,758, the filler tube effects insertion of the balloon. In U.S. Pat. No. 4,485,805, the balloon is inserted into a finger cot that is attached by string to the end of a conventional gastric tube that is inserted down the patient's throat. The balloon of European Patent No. 246,999 is inserted using a gastroscope with integral forceps.

In U.S. Pat. Nos. 4,416,267; 4,485,805; 4,694,827; 4,739,758; 4,899,747 and European Patent No. 246,999, the balloon is inflated with a fluid from a tube extending down from the patient's mouth. In these patents, the balloon also is provided with a self-sealing hole (U.S. Pat. No. 4,694,827), injection site (U.S. Pat. No. 4,416,267, U.S. Pat. No. 4,899,747), self-sealing fill valve (U.S. Pat. No. 4,485,805), self-closing valve (European Patent No. 246,999) or duck-billed valve (U.S. Pat. No. 4,739,758). U.S. Pat. No. 4,723,547 uses an elongated thick plug and the balloon is filled by inserting a needle attached to an air source through the plug.

U.S. Pat. No. 4,607,618 describes a collapsible appliance formed of semi-rigid skeleton members joined to form a collapsible hollow structure. The appliance is not inflatable. It is endoscopically inserted into the stomach using an especially adapted bougie having an ejector rod to release the collapsed appliance. Once released, the appliance returns to its greater relaxed size and shape.

U.S. Pat. No. 5,129,915, the contents of which are incorporated herein by reference, relates to an intragastric balloon that is intended to be swallowed and that inflates automatically under the effect of temperature. U.S. Pat. No. 5,129,915, discusses three ways that an intragastric balloon might be inflated by a change in temperature. A composition comprising a solid acid and non-toxic carbonate or bicarbonate is separated from water by a coating of chocolate, cocoa paste or cocoa butter that melts at body temperature. Alternatively, citric acid and an alkaline bicarbonate coated with non-toxic vegetable or animal fat melting at body temperature and which placed in the presence of water, would produce the same result. Lastly, the solid acid and non-toxic carbonate or bicarbonate are isolated from water by an isolation pouch of low-strength synthetic material which it will suffice to break immediately before swallowing the bladder. Breaking the isolation pouches causes the acid, carbonate or bicarbonate and water to mix and the balloon to begin to expand immediately. A drawback of thermal triggering of inflation as suggested by U.S. Pat. No. 5,129,915 is that it does not afford the degree of control and reproducibility of the timing of inflation that is desirable and necessary in a safe self-inflating intragastric balloon.

SUMMARY OF THE INVENTION

A free-floating, intragastric, volume-occupying device that can be inserted into the stomach simply by the patient swallowing it and letting peristalsis deliver it into the stomach in the same manner that food is delivered is desirable.

Volume-occupying devices and methods for manufacturing, deploying, inflating, tracking, deflating and retrieving of such devices are provided. The devices and methods of the preferred embodiments may be employed for treating obesity. Methods employing the device of the preferred embodiments need not utilize invasive procedures, but rather the device may simply be swallowed by a patient. Once in the stomach of the patient, the device will increase in volume. After a predetermined time period has passed, or upon demand, the device will decrease in volume and pass through the remainder of the patient's digestive tract.

In certain preferred embodiments the inflation subcomponent of the device is incorporated within the interior or into the wall of the volume-occupying subcomponent. Inflation may be achieved through a chemical reaction between reactive agents producing a gas or other fluid byproduct. Various types of environmentally sensitive and mechanical barriers may be employed to compartmentalize the reactive agents so as to delay inflation until the device is in the patient's stomach. Alternatively, inflation of the volume-occupying subcomponent may be achieved by electrical or mechanical means actuated by an exterior signal such as radiofrequency (RF) or a magnetic field or pulse. Alternatively, the volume-occupying subcomponent may be comprised of a thermo-elastic polymer susceptible to volume expansion upon introduction to a predefined temperature or to the pH environment of the stomach. Alternatively, the volume-occupying subcomponent may be comprised of a memory polymer designed to form an expanded volume-occupying subcomponent in its relaxed state and that is restricted to a swallowable size prior to ingestion with such restriction breaking or degrading in the stomach to allow the volume-occupying subcomponent to expand. Inflation may also be achieved by use of a removable tube that initially remains in fluid contact with the device after it has been swallowed by the patient.

In other embodiments, the volume-occupying subcomponent of devices may be formed by injection, blow or rotational molding of a flexible, gas-impermeable, biocompatible material, such as, for example, polyurethane or polyethylene terephthalate. Materials that may be used to improve the gas impermeability of the volume-occupying subcomponent include, but are not limited to, silicon oxide (SiOx), gold or any noble metal, PET coated with saran, conformal coatings and the like. To facilitate greater gas-impermeable characteristics, the volume-occupying subcomponent may be further coated with one or more gas-barrier compounds. Alternatively, the volume-occupying subcomponent may be formed of a Mylar polyester film coating or kelvalite, silver or aluminum as a metallicized surface to provide a gas impermeable barrier. The volume-occupying subcomponent may further incorporate a weighting element either located within its interior or within its wall.

In certain preferred embodiments, deflation subcomponents may be integrated into the wall of the volume-occupying subcomponent or at the head region of the volume-occupying subcomponent at the end of the volume-occupying subcomponent shaft. Deflation of the device may be either time dependant or on-demand. Deflation may be triggered by, for example, chemical degradation, lithotripsy techniques, externally applied magnetic field, remotely activated microchips; voltage differences; and light degrading compounds.

In further embodiments, the device employs a delivery state in which the device is packaged such that the device may be swallowed while producing minimal discomfort to the patient. In a delivery state, the device may be packaged into a capsule. Alternatively, the device may be coated with a material operable to confine the device and facilitate swallowing. Various techniques may also be employed to ease swallowing of the device including, for example, wetting, temperature treating, lubricating, and treating with pharmaceuticals such as anesthetics.

In other embodiments, the devices may incorporate a tracking or visualization component that enables physicians to determine the location and/or orientation of the device within the patient's body. Tracking subcomponents may include incorporating a barium stripe or geometric shape into the wall of the volume-occupying subcomponent. Tracking and visualization, may also be achieved by incorporation of a microchip, infrared LED tag, ultraviolet absorbing compounds, fluorescent or colored compounds and incorporation of metalized strips and patterns into the volume-occupying subcomponent or other subcomponents of the device. Such techniques may also be used to obtain certain device specific information and specifications while the device remains inside the patient's body.

In other preferred embodiments, the device may also serve as a means for delivering pharmaceuticals to a patient, either in conjunction with obesity treatment or independent thereof. For example, the device may be coated or otherwise impregnated with pharmaceuticals for control of stomach acid, treatment of gastroesophageal reflux disease (GERD), nausea, control of body weight, control of blood glucose, modulation of gastric emptying, modulation of gastric absorption, modulation of hormone levels and satiety signaling.

In a first aspect, a swallowable, self-inflating intragastric balloon system is provided comprising: a balloon comprising a self-sealing valve system attached to a wall of the balloon in a central lumen of the balloon by an adhesive with a shear force greater than about 40 N, the self-sealing valve system comprising a septum, a retaining structure, and a continuous ring, wherein the septum has a durometer that is less than a durometer of the retaining structure, wherein the continuous ring is configured to exert a compressive force on the septum, wherein the balloon has a weight of less than about 15 g, wherein the balloon is configured to have a shape upon full inflation selected from the group consisting of ellipsoid, spheroid, and oblate spheroid, and wherein the balloon is configured to have a volume of from about 90 $cm^3$ to about 350 $cm^3$ upon full inflation; an inner container within the central lumen of the balloon, the inner container containing from about 0.28 grams to about 4 grams of an inflation agent, wherein up to about 80 wt. % of a total amount of the inflation agent is powdered citric acid, with a remainder of the inflation agent comprising powdered sodium bicarbonate; and an outer container configured to be swallowed by a patient without assistance, the outer container comprising a material and a structure configured to control timing of inflation, and containing the inner container and the balloon in a compacted state.

In an embodiment of the first aspect, the retaining structure comprises a material selected from the group consisting of silicone, rubber, acrylic, epoxy, a thermoplastic elastomer, and a thermoplastic polyurethane.

In an embodiment of the first aspect, the system further comprises an inoculation spacer situated in the central lumen of the balloon adjacent to the septum.

In an embodiment of the first aspect, the activation agent comprises an aqueous solution of up to about 50% citric acid in solution into the central lumen of the balloon, and wherein a total amount of citric acid in the inflation agent and the activation agent combined creates a pH of about 6 or less in a residual liquid remaining after completion of a $CO_2$ generating reaction of the inflation agent.

In an embodiment of the first aspect, the inoculation spacer is in a form of a tube or a cylinder.

In an embodiment of the first aspect, the balloon is situated in the outer container in a deflated and folded state, wherein folds of the balloon are configured to localize an activation agent injected into the central lumen of the balloon adjacent to the inner container.

In an embodiment of the first aspect, the system further comprises a void space in the outer container configured for occupation by activation agent injected inside the central lumen of the balloon, wherein a volume of the void space is from about 0.3 ml to about 4.5 ml.

In an embodiment of the first aspect, the septum has a durometer of about 20 Shore A to about 60 Shore D, and wherein the retaining structure has a durometer of from about 40 Shore D to about 70 Shore D, In an embodiment of the first aspect, the continuous ring is radio-opaque.

In an embodiment of the first aspect, the balloon is configured to have, upon full inflation, an internal nominal pressure at about 37° C. of from about 0 Pa to about 103421 Pa.

In an embodiment of the first aspect, the balloon is configured to have, upon full inflation, a nominal radius of from about 2.5 cm to about 7.6 cm, a nominal height of from about 0.6 cm to about 7.6 cm.

In an embodiment of the first aspect, from about 10 wt. % to about 80 wt. % of the total amount of the inflation agent is powdered citric acid.

In an embodiment of the first aspect, the inner container has a longest dimension of from about 1.9 cm to 2.7 cm, a width of from about 0.6 cm to about 1 cm, and a volume of from about 0.41 ml to about 1.37 ml.

In an embodiment of the first aspect, the outer container has a longest dimension of from about 2.4 cm to 6.3 cm, a width of from about 0.9 cm to about 2.4 cm, and a volume of from about 1.2 ml to about 8.25 ml.

In an embodiment of the first aspect, at least one of the inner container or the outer container comprises gelatin.

In an embodiment of the first aspect, at least one of the inner container or the outer container comprises a gelatin capsule.

In an embodiment of the first aspect, the balloon is fully sealed 360 degrees around with no external opening or orifice to the central lumen.

In an embodiment of the first aspect, the balloon has a smooth surface.

In a second aspect, a method for fabricating a swallowable, self-inflating intragastric balloon system is provided, the method comprising: adhering a self-sealing valve system to a first half of a wall of a balloon by an adhesive with a shear force greater than about 40 N, the self-sealing valve system comprising a septum, a retaining structure, and a continuous ring, wherein the septum has a durometer that is less than a durometer of the retaining structure, wherein the continuous ring is configured to exert a compressive force on the septum; joining the first half of the wall of the balloon to a second half of the wall of the balloon, wherein either the first half of the wall of the balloon or the second half of the wall of a balloon comprises a hole having a smallest dimension of at least about 0.6 cm, and a largest dimension of no more than about 3.8 cm; inverting the balloon through the hole; placing an inner container within a central lumen of the inverted balloon, the inner container containing from about 0.28 grams to about 4 grams of an inflation agent, wherein up to about 80 wt. % of a total amount of the inflation agent is powdered citric acid, with a remainder of the inflation agent comprising powdered sodium bicarbonate; and applying a patch of a material to seal the hole, whereby a balloon having a smooth outer surface is obtained, wherein the balloon has a weight of less than about 15 g, wherein the balloon is configured have a shape upon full inflation selected from the group consisting of ellipsoid, spheroid, and oblate spheroid, and wherein the balloon is configured to have a volume of from about 90 $cm^3$ to about 350 $cm^3$ upon full inflation.

In an embodiment of the second aspect, joining comprises welding or adhesively adhering.

In a third aspect, a method for inflating a swallowable, self-inflating intragastric balloon is provided, comprising: a balloon comprising a self-sealing valve system attached to a wall of the balloon in a central lumen of the balloon by an adhesive with a shear force greater than about 40 N, the self-sealing valve system comprising a septum, a retaining structure, and a continuous ring, wherein the septum has a durometer that is less than a durometer of the retaining structure, wherein the continuous ring is configured to exert a compressive force on the septum, wherein the balloon has a weight of less than about 15 g, wherein the balloon is configured have a shape upon full inflation selected from the group consisting of ellipsoid, spheroid, and oblate spheroid, and wherein the balloon is configured to have a volume of from about 90 $cm^3$ to about 350 $cm^3$ upon full inflation; an inner container within the central lumen of the balloon, the inner container containing from about 0.28 grams to about 4 grams of an inflation agent, wherein up to about 80 wt. % of a total amount of the inflation agent is powdered citric acid, with a remainder of the inflation agent comprising powdered sodium bicarbonate; an outer container configured to be swallowed by a patient without assistance, the outer container comprising a material and a structure configured to control timing of inflation, and containing the inner container and the balloon in a compacted state; and an inoculation spacer configured to guide a needle into the septum for injection of an activation agent into the central lumen of the balloon while avoiding puncture of the inner container, wherein the inoculation spacer is situated in the outer container, adjacent to the septum; injecting an activation agent into the central lumen of the balloon through the wall of the balloon atop the septum and through the septum itself using the inoculation spacer as a guide, whereby degradation of the inner container is initiated; thereafter allowing the system to be swallowed by a patient in need thereof; degrading the outer container in a stomach of the patient; initiating inflation by contact of the activation agent with the inflation agent via degradation of the inner container, wherein inflation is initiated no earlier than about 30 seconds after injection of the activation agent; unfolding the balloon via inflation from about 60 seconds to about 15 minutes after injection of activation agent; and inflating the balloon such that at least about 10% of the occupyable volume of the balloon is filled within about 30 minutes, at least about 60% of the occupyable volume of the balloon is filled within about 12 hours, and at least about 90% of the occupyable volume of the balloon is filled within about 24 hours.

In an embodiment of the third aspect, the activation agent is substantially localized in the balloon adjacent to the inner container upon injection.

In an embodiment of the third aspect, the balloon is compacted such that, upon initiating inflation, the balloon unfolds in a manner that creates a surface area sufficiently large so as to prohibit the balloon from passing through the pyloric sphincter.

In an embodiment of the third aspect, a pH of any remnant liquid inside the central lumen of the balloon is acidic such that any balloon leakage or breach that allows stomach acid to enter the balloon does not initiate reinflation of the balloon.

In an embodiment of the third aspect, allowing the system to be swallowed by a patient in need thereof comprises swallowing, via normal peristalsis, the outer container containing the inner container, inoculation spacer, and the balloon in a compacted state.

In an embodiment of the third aspect, the inner container comprises a gelatin capsule.

BRIEF DESCRIPTION OF THE DRAWINGS

FIGS. 17A and B are perspective views of a deflation subcomponent, in accordance with a preferred embodiment.

FIG. 18 is a cross-sectional view of a deflation subcomponent, in accordance with a preferred embodiment.

FIG. 19 is a cross-sectional view of a deflation subcomponent, in accordance with a preferred embodiment.

FIGS. 20A-D are cross-sectional views of a deflation subcomponent, in accordance with a preferred embodiment.

FIG. 44A depicts a silicone head 441 with radioopacity ring 442, trimmed 30 D silicone septum 443, Nylon 6 inoculation spacer 444, folded balloon 445, inner container 446, and outer container 447 as constituents of the system in unassembled form.

FIG. 45A is a perspective view; and FIG. 45B is a side view.

FIG. 46A is a perspective view; FIG. 46B is a side view; and FIG. 46C is a top view.

FIG. 47A is a perspective view; FIG. 47B is a top view; FIG. 47C is a bottom view; FIG. 47D is a side view; and FIG. 47E is a cross section view through A-A.

DETAILED DESCRIPTION OF THE PREFERRED EMBODIMENT

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

The term "degradable" as used herein is a broad term, and is to be given its ordinary and customary meaning to a person of ordinary skill in the art (and is not to be limited to a special or customized meaning), and refers without limitation to a process by which structural integrity of the balloon is compromised (e.g., by chemical, mechanical, or other means (e.g., light, radiation, heat, etc.) such that deflation occurs. The degradation process can include erosion, dissolution, separation, digestion, disintegration, delamination, comminution, and other such processes.

The term "swallowable" as used herein is a broad term, and is to be given its ordinary and customary meaning to a person of ordinary skill in the art (and is not to be limited to a special or customized meaning), and refers without limitation to ingestion of a balloon by a patient such that the outer capsule and its constituents are delivered to the stomach via normal peristalsis movement. While the systems of preferred embodiments are swallowable, they are also configured by ingestion by methods other than swallowing. The swallowability of the system is derived, at least in part, by the outer container size, which is sufficient to contain the inner container and its constituents, an amount of activation agent injected prior to administration, the balloon size, and the balloon material thickness. The system is preferably of a size less than the average normal esophagus diameter.

Described herein is an orally ingestible device that is able to traverse the alimentary canal. The device may be useful, for example, as an intragastric volume-occupying device. The device overcomes one or more of the above-described problems and shortcomings found in current intragastric volume-occupying devices.

Figure 1A:
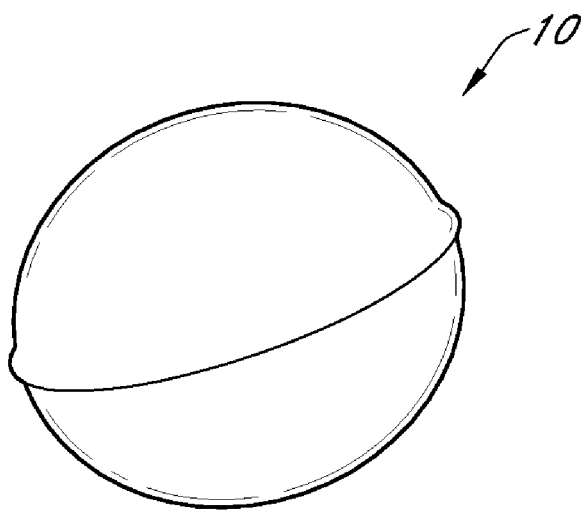
FIG. 1A is a perspective view of an exemplary intragastric volume-occupying device in an inflated state, in accordance with a preferred embodiment.
Figure 1B:
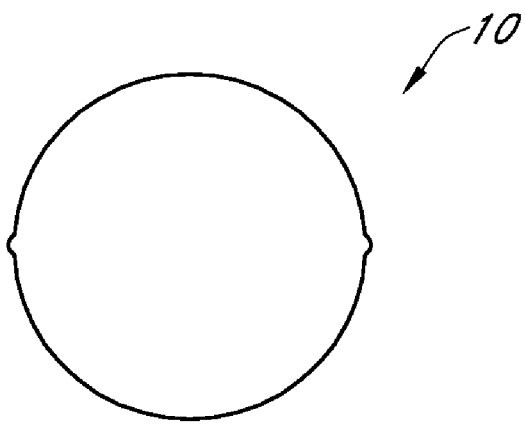
FIG. 1B is a cross-sectional view of an exemplary intragastric volume-occupying device in an inflated state, in accordance with a preferred embodiment.
Figure 2A:
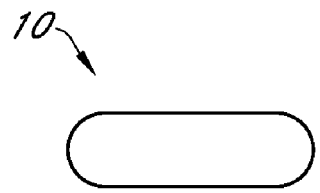
FIG. 2A is a cross-sectional view of an exemplary intragastric volume-occupying device in a delivery state, in accordance with a preferred embodiment.
Figure 3A:
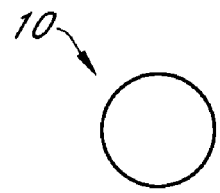
FIG. 3A is a cross-sectional view of an exemplary intragastric volume-occupying device in a delivery state, in accordance with a preferred embodiment.
Figure 2B:
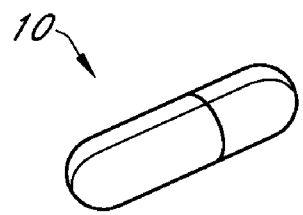
FIG. 2B is a perspective view of an exemplary intragastric volume-occupying device in a delivery state, in accordance with a preferred embodiment.
Figure 3B:
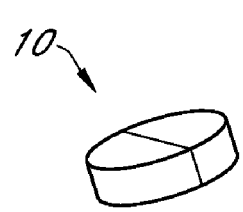
FIG. 3B is a perspective view of an exemplary intragastric volume-occupying device in a delivery state, in accordance with a preferred embodiment.
Figure 4A:
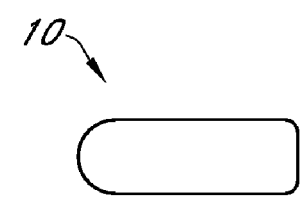
FIG. 4A is a cross-sectional view of an exemplary intragastric volume-occupying device in a delivery state, in accordance with a preferred embodiment.
Figure 5A:
FIG. 5A is a cross-sectional view of an exemplary intragastric volume-occupying device in a delivery state, in accordance with a preferred embodiment.
Figure 4B:
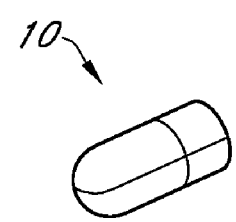
FIG. 4B is a perspective view of an exemplary intragastric volume-occupying device in a delivery state, in accordance with a preferred embodiment.
Figure 5B:
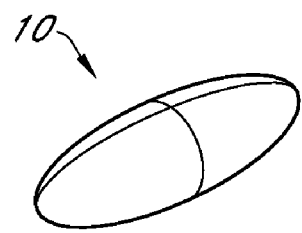
FIG. 5B is a perspective view of an exemplary intragastric volume-occupying device in a delivery state, in accordance with a preferred embodiment.

FIG. 1A is an illustration of a device 10 in an inflated state according to the present invention. FIG. 1B is a cross-sectional illustration of the device 10. Certain preferred embodiments employ a volume-occupying subcomponent, an inflation subcomponent, a deflation subcomponent, and a delivery subcomponent. Devices according to the present inventions may further comprise a tracking subcomponent and/or a drug delivery subcomponent. FIGS. 2A through 5B are illustrations of the devices 10 according to the present invention that are in a delivery state, e.g., the devices 10 are in a compact, non-inflated state. FIGS. 2A, 3A, 4A, and 5A are cross-sectional views of the devices 10 and FIGS. 2B, 3B, 4B, and 5B are perspective views of the corresponding devices 10. Generally, in the delivery state, the device 10 is in the form of an ingestible capsule or other similarly sized and shaped package.

In order to more clearly describe the subject matter of the preferred embodiments, different embodiments of the same subcomponent will be described under a single relevantly-titled subheading. This organization is not intended to limit the manner in which embodiments of different subcomponents may be combined in accordance with the present invention.

Inflation Subcomponents

Devices according to the present invention are intended for ingestion by a patient and deployment without the need to resort to invasive methods. It is therefore desirable that the device of the preferred embodiments be operable to conform to a compact delivery state which can be swallowed by a patient with minimal discomfort. Once in the stomach, it is desirable for the device to assume a substantially larger deployed state. In order to achieve the transition from a delivery state to a deployed state the device is subjected to an inflation step performed by an inflation subcomponent.

The inflation subcomponent may generally be located entirely within the volume-occupying subcomponent or integrated into the wall of the volume-occupying subcomponent. As will be further described below, the inflation subcomponent may be self-contained, e.g., all elements necessary for inflation of the volume-occupying subcomponent are situated on or within the device at the time the patient ingests the device in the delivery state. Alternatively, in order to inflate, the inflation subcomponent may require outside inputs such as fluids, activation agents, or externally generated signals or other forms of communication.

In certain preferred embodiments, the volume-occupying subcomponent is filled with a fluid using tubing which is subsequently pulled away from the volume-occupying subcomponent. One end of the volume-occupying subcomponent has a port connected to tubing of sufficient length that when unwound can span the entire length of the esophagus, from mouth to stomach. This tubing is connected to the volume-occupying subcomponent with a duct valve that can tear away from the volume-occupying subcomponent and self-seal once the volume-occupying subcomponent is inflated. A physician secures one end of the tubing as the patient swallows the device. Once the device is residing within the stomach, the physician uses the tube to transmit a fluid, such as air, into the volume-occupying subcomponent and thereby inflate it. After the volume-occupying subcomponent is fully inflated, the tubing is released and can be pulled out from inside the patient.

The tube may be released in a number of manners that are either novel or known in the art. For example, the tubing may be detached by the physician by applying a gentle force, or tug, on the tubing. Alternatively, the tubing may be detached by the physician by actuating a remote release, such as a magnetic or electronic release. Additionally, the tubing may be released from the volume-occupying subcomponent by an automatic ejection mechanism. Such an ejection mechanism may be actuated by the internal pressure of the inflated volume-occupying subcomponent. For example, the ejection mechanism may be sensitive to a specific pressure beyond which it will open so as to release any excess pressure and simultaneously release the tube. This embodiment provides a desirable feature through combining release of the tubing with a safety valve that serves to avert accidental over inflation of the volume-occupying subcomponent in the patient's stomach.

This automatic release embodiment also provides the benefit that the device inflation step may be more closely monitored and controlled by the physician. Current technology allows for a self-inflating intragastric volume-occupying subcomponent which generally begins to inflate in a four minute timeframe after injection with an activation agent such as citric acid. A drawback to this approach is that the volume-occupying subcomponent may begin to inflate prior to the physician knowing whether the device is truly residing within the stomach. In some cases, the capsule may still be in the esophagus at the time when inflation starts to occur. Patients with gastric dumping syndrome or rapid gastric emptying may end up with the volume-occupying subcomponent in their small intestine prior to the time that inflation occurs. It would therefore be a safer alternative to inflate the volume-occupying subcomponent on command, once the physician can ascertain that the volume-occupying subcomponent is residing in the correct location.

In certain other preferred embodiments, the volume-occupying subcomponent is inflated by one or more chemical reactions that take place once the device is positioned within the stomach. Such chemical reactions may include, but are not limited to: combining wax, $O_2$, and heat to form $CO_2$ and $H_2O$; combining $NaHCO_3$ and acetic acid or citric acid to form $CO_2$ and $H_2O$; combining sugar and yeast to form ethanol and $CO_2$; combining $C_xH_y$, an $xO_2$, and energy to form $xCO_2$ and $yH_2O$; combining sulfur and $O_2$ to form $SO_2$; combining potassium and water to form $H_2$ and KOH; combining $C_6H_{12}O_6$ and yeast to form $2C_2H_5OH$ and $2CO_2$; combining cupric bicarbonate and heat to form CuO, water and $CO_2$; combining magnesium and $H_2SO_4$ to form $H_2$ and $MgSO_4$; combining $NaHCO_3$ and HCl to form water, $CO_2$, and NaCl; a combustion reaction; or combining dry ice and heat to form $CO_2$. In such embodiments it may or may not be necessary to compartmentalize or otherwise separate the components of the chemical reaction while the device is in the delivery state. When compartmentalization is necessary, one skilled in the art will understand that various methods exist for temporarily separating the components, including but not limited to employing: temperature sensitive barriers, energy sensitive barriers, time sensitive barriers, light sensitive barriers, other environmentally sensitive barriers, chemically sensitive barriers, and mechanical barriers.

Figure 6:
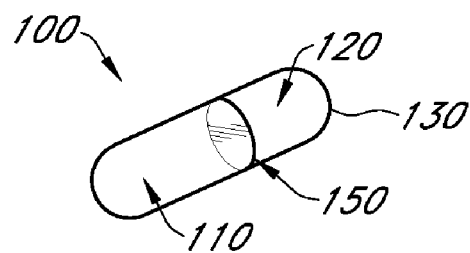
FIG. 6 is a perspective view of an exemplary inflation subcomponent in a delivery state, in accordance with a preferred embodiment.
Figure 8:
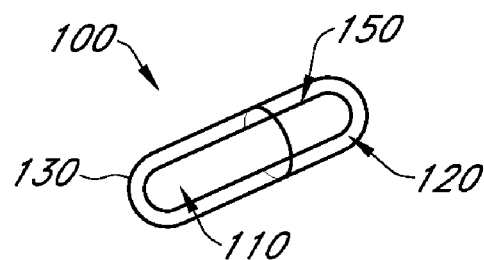
FIG. 8 is a perspective view of an exemplary inflation subcomponent in a delivery state, in accordance with a preferred embodiment.

For example, the embodiments illustrated in FIGS. 6 and 8 have an inflation subcomponent 100 that includes a liquid 110 and a solid reactant 120 packaged into a two-part capsule 130. For example, the solid reactant 120 may be in the form of a carbonate such as bicarbonate. The liquid 110 and solid reactant 120 are separated by a mechanical barrier 150 present within the capsule 130. To initiate the chemical reaction between the liquid 110 and the solid reactant 120, a force is applied to the capsule 130 causing the capsule 130 to break and the liquid 110 and solid reactant 120 to mix and react with one another. The resulting reaction produces a gas byproduct which thereby inflates the volume-occupying subcomponent with which the inflation subcomponent 100 is associated. Other configurations are also contemplated, e.g., an inflation agent mixture (e.g., solid sodium bicarbonate and solid citric acid) in an inner container, where gas generation is initiated by an activation agent (e.g., water, or an aqueous citric acid solution) that causes dissolution or degradation of the inner container so as to contact the inflation agent mixture.

In one embodiment, the barrier or barriers may incorporate an environmentally-sensitive shape-memory material, e.g. a polymer or a metal such as Nitinol (a shape memory alloy of nickel and titanium). The shape-memory material may, for example, be treated to change configuration at or above a certain temperature thereby mechanically disrupting the barrier and allowing mixing of the inflationary reactants. For example, such disruption may be triggered when the Nitinol contained in the barrier is heated to its transition temperature by the environment of the stomach (in which case it may be necessary to store the device below room temperature prior to administration) or such disruption may be triggered when the Nitinol is heated to its transition temperature above the body temperature. Such source of heat may be generated by any means of heat generation described below. The transition temperature of Nitinol may be modified so as to achieve the metal's configuration change at the desired temperature or temperature range.

Figure 7:
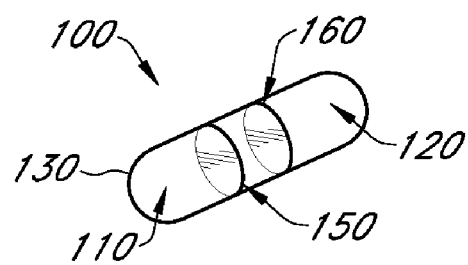
FIG. 7 is a perspective view of an exemplary inflation subcomponent in a delivery state, in accordance with a preferred embodiment.

It may be advantageous to delay the initiation of such reaction until the volume-occupying subcomponent has had sufficient time to reach the stomach. Accordingly, as illustrated in FIG. 7, another embodiment of the device may contain an additional soluble barrier 160 positioned between the solid reactant 120 and the mechanical barrier 150 to be broken. Such additional barrier 160 may be, for example, a dissolvable polysaccharide barrier that dissolves within several minutes of contact with the liquid 110 such that inflation agents do not mix and the chemical reaction does not occur until several minutes following the breaking of the capsule 130.

Figure 9:
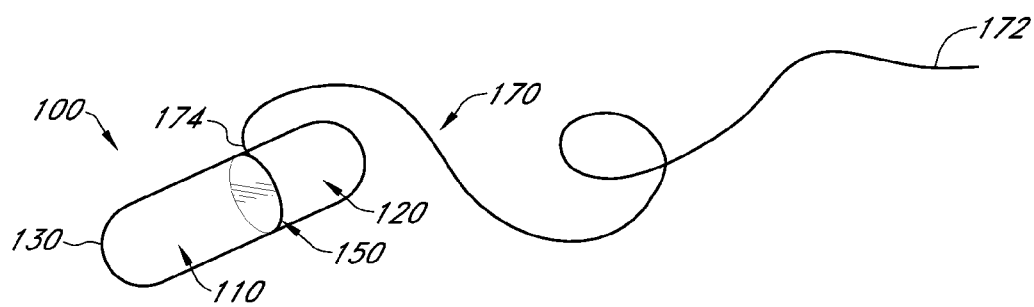
FIG. 9 is a perspective view of an exemplary inflation subcomponent in a delivery state, in accordance with a preferred embodiment.

In another example, as illustrated in FIG. 9, the barrier 150 separating the chemical inflation agents is connected to the end of a string or tubing 170 whose length is approximately the distance from the patient's mouth to stomach. In this example, a distal end 172 of the string or tubing 170 is held by the administrator of the device to the patient while the device is being administered to the patient, and the length of the string or tubing 170 provides a measure indicating when the device has reached the stomach. Upon the device's reaching of the stomach, the administrator of the device can then pull the distal end 172 of string 170 to disrupt or move the barrier 150 sufficiently for the chemical agents to mix and react with one another and initiate the inflation process. The proximal end 174 of the string or tube 170 may be directly connected to the barrier 150 and, upon its detachment from the barrier 150, pass through a self-sealing portion of the volume-occupying subcomponent wall (not shown). Alternatively, the proximal end 174 of the string or tube 170 need not be directly connected to the barrier 150 and instead can be connected to the device in any manner such that tension from a pull of the string 170 is transferred to the barrier 150 sufficiently to cause its movement or breakage. For example, the string or tubing 170 may be connected to a portion of the volume-occupying subcomponent wall that is connected to a portion of the barrier 150. It may be necessary for the outer coating of the device to dissolve at least partially so that tension from the pull may be transferred to the barrier 150. The pull of the string 170 will also initiate or contribute to the detachment of the string 170 from the device. The string 170 may be able to detach from the device as a result of the pull from the administrator or a combination of such pull and other means. For example, the proximate end 174 of string 170 or the materials attaching it to the device may be comprised of materials that dissolve or degrade in the stomach environment that facilitate the detachment of the string 170.

In another example, the barrier separating the chemical inflation agents is ultraviolet, or UV, sensitive. The device in the delivery state may include a UV blocking outer layer that can be removed immediately prior to ingestion of the device. Once the UV blocking layer is removed the UV sensitive barrier is exposed to UV. The exposure initiates a timed degradation of the barrier, subsequent mixing of the agents, and inflation of the volume-occupying subcomponent. Such UV exposure to the barrier may occur prior to administration of the device to the patient or may be performed following administration of the device to the patient. UV exposure to the barrier following administration of the device to the patient may be accomplished by exposing the barrier to a UV light source external to the volume-occupying subcomponent, e.g., by inserting an endoscope or wand with a UV light source at its end orally down the gastrointestinal tract and which then emits UV light at the barrier. In such case the device may be tethered to the UV light source such that the UV light source and the device are administered orally concurrently or one immediately following the other, resulting in the UV light source and the device being located proximate to each other to allow for accurate direction of UV light onto the barrier. Alternatively, UV exposure to the barrier following administration of the device to the patient may be accomplished by exposing the barrier to a UV source within the volume-occupying subcomponent that is activated at the time of administration to the patient to emit UV light.

In another embodiment, an intragastric volume-occupying device is engineered with a power source and radiofrequency transformer such that an external wireless RF signal is able to be transformed into electric energy and create a voltage difference to inflate the volume-occupying subcomponent. The RF signal may be received by means of an antenna adjacent to the power source. For example, the external RF energy may be utilized to power a pump to pump stomach acids into an internal reservoir of the device to react with an inflationary agent such as a carbonate. Alternatively, the external RF energy may be used to open a valve or barrier situated between inflation reactants.

In an alternative example, inflation may be achieved by means of a polymer microfilm situated adjacent to at least one inflationary reactant. The electric energy triggered by the RF signal causes the microfilm to heat at least one reactant which in turn may be sufficient to generate a gas or may be sufficient to provide the necessary reaction energy for the combination of multiple inflationary reactants to form a gas. The at least one reactant may include sodium carbonate and the gas may include carbon dioxide.

In another embodiment, inflation of the volume-occupying subcomponent is actuated by an externally applied magnetic field. For example, following ingestion of the device to the stomach, a magnetic field, introduced into the vicinity of the device, can cause a solenoid to close which in turn closes a circuit configured to generate heat when in a closed state. The generated heat in turn heats a temperature sensitive sealing element incorporated in the barrier separating the inflation agents. Upon achieving a predetermined temperature, the temperature sensitive sealing element is disrupted or breached and the inflation agents mix, thereby inflating the volume-occupying subcomponent. Alternatively, the generated heat may be sufficient to heat at least one reactant which in turn may be sufficient to generate a gas or may be sufficient to provide the necessary reaction energy for the combination of multiple inflationary reactants to form gas.

Figures 10A, 10B:
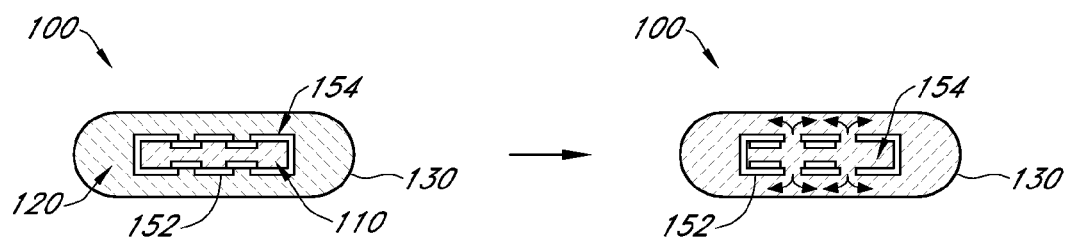
FIGS. 10A and B are cross-sectional views of an exemplary inflation subcomponent, in accordance with a preferred embodiment.

As a further example, the device may contain a pump that is actuated by pulsatile magnetic energy applied externally and that pumps acid or other fluids in the stomach into the volume-occupying subcomponent and which react with an inflation agent (such as carbonate) inside of the volume-occupying subcomponent causing the volume-occupying subcomponent to inflate. Such actuation may be by means of a voltage electromagnetically induced by means of a conducting wire forming a closed loop connected to such pump. As a further example, the barrier separating inflation agents may contain a magnet, metal or other magnetophilic substance that, upon external application of a magnetic field, is disrupted or otherwise moved sufficiently to allow a breakage or opening in the barrier sufficient for the inflation agents to mix, thereby inflating the volume-occupying subcomponent. FIGS. 10A and 10B illustrate another example in which the barrier 152 between inflation agents may contain a valve or valves 154 (such as a spool valve) that, upon external application of a magnetic field, are opened to allow the inflation agents to mix, thereby inflating the volume-occupying subcomponent.

As a further example, one or more portions of the barrier separating inflation agents may be stabilized or held together by a magnetic field emanating from a magnet in the device that, upon external application of a degaussing or demagnetizing force, eliminates or reduces the magnetic field sufficiently for one or more portions of the barrier to be destabilized or otherwise moved sufficiently to allow a breakage or opening in the barrier sufficient for the inflation agents to mix, thereby inflating the volume-occupying subcomponent. Destabilization or movement of the barrier upon elimination or reduction of the magnetic field may be aided by incorporating one or more spring loaded elements into the barrier that are constrained by the magnetic field.

In other embodiments, the barrier separating the inflation reactants may be a valve that is initially held closed by a spring-loaded element and that is subsequently released to allow the valve to open thereby allowing the reactants to mix and inflation to commence. The release of such spring-loaded element may be accomplished by any of the methods described in this application to actuate a mechanical movement or breakage in the device.

In other embodiments, inflation of the volume-occupying subcomponent may be actuated by emission of a gas within the volume-occupying subcomponent that is generated via an oxidation-reduction reaction. For example, oxygen and hydrogen gas may be generated to expand the volume-occupying subcomponent by electrolyzing a water subcomponent within the volume-occupying subcomponent using stainless steel electrodes. As a further example, the volume-occupying subcomponent may be inflated by the emission of oxygen gas generated by an electricity-actuated oxidation-reduction reaction between two different metals, where one metal contains an oxide. As a further example, oxalic acid may be electrolyzed. An electrical current to actuate the reaction examples described above may be generated by any of the means for generating such current described elsewhere in this application.

Means for generating electricity or heat to actuate any of the inflation mechanisms described in this application may also include incorporation of a miniature battery (e.g. a button cell) in the device, which may, for example, be activated prior to device delivery or by an external RF or magnetic signal.

Heat or electricity may also be generated by a source external to the device and may be transmitted to the device via a tube or string attached to the device at its distal end and attached to the external source at its proximal end. Such tube or string may be released by means of an electric signal or by any of the means for releasing a tube or string attached to the device described in the "Inflation Subcomponents" and "Deflation Subcomponents" sections of this application, and, in addition, may perform any of the tube or string functions described in the "Inflation Subcomponents" and "Deflation Subcomponents" sections of this application.

In another embodiment, an intragastric volume-occupying subcomponent is engineered with a sealed container inside of it, with such container containing a mixture of one or more compressed gases and with inflation achieved by the release of gas from this container. Alternatively, the volume-occupying subcomponent may be engineered in inflated form with the desired amount of gas inside of it and compressed inside a container sufficiently small to be administered to the patient. Such compressed gas or mixture of gases may include, but are not limited to, one or more of the following: carbon dioxide, oxygen, nitrogen, and argon. Release of gas (in the case of the invention embodiment where a gas container is engineered inside of the volume-occupying subcomponent) or expansion of the volume-occupying subcomponent (in the case of the invention embodiment where a volume-occupying subcomponent filled with the desired amount of gas is compressed into a delivery container) may be achieved by degradation or destruction of all or a part of the container unit containing the gas. Such degradation or destruction may be achieved by any of the means described above as example methods to destroy a mechanical barrier between reactants. For example, all or part of the container may be composed of a polysaccharide or polymer structure.

It has been hypothesized that in order to produce the desired feeling of satiety in a patient, a portion of the intragastric volume-occupying subcomponent must settle within or below the surface of the stomach fluids. It may therefore be advantageous to incorporate a weight into or on the intragastric volume-occupying subcomponent. To this end, in certain additional preferred embodiments, the inflation subcomponent may be formed so as to also incorporate or otherwise perform a weighting function.

Figure 11A:
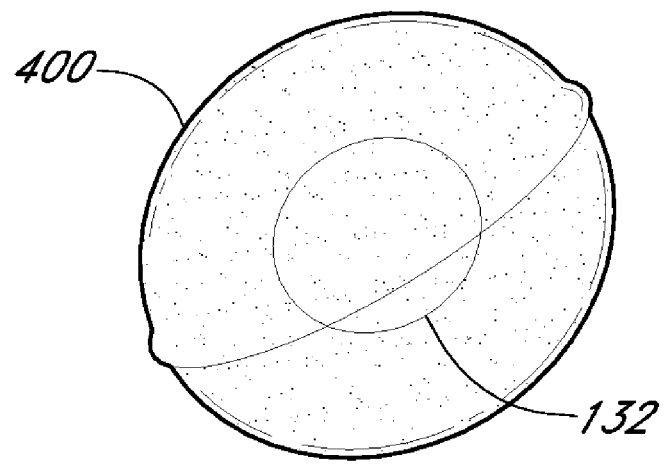
FIGS. 11A and B are perspective views of an exemplary intragastric volume-occupying device in an inflated state, in accordance with a preferred embodiment.
Figure 11B:
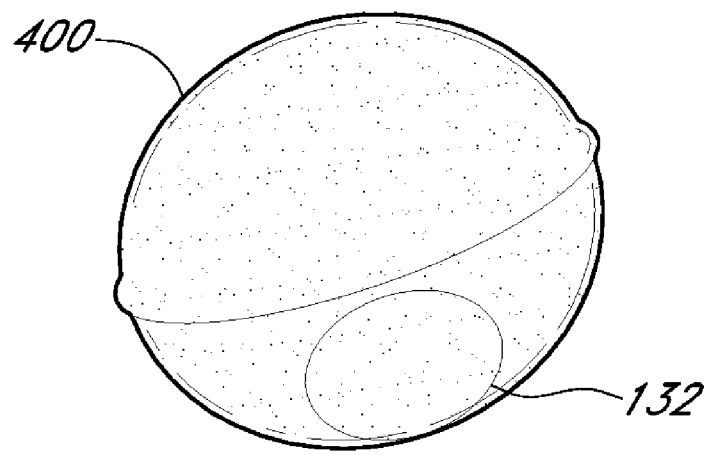

For example, in embodiments employing multiple agents or chemical components which react with one another to inflate the volume-occupying subcomponent, the proportions and amounts of each agent may be manipulated such that the inflation reaction stops prior to exhaustion of all of one of the agents. The remaining quantity of agent will thereby function as a weight in the volume-occupying subcomponent. Alternatively, various other elements of the inflation subcomponent may be designed to ultimately serve as a weight, e.g. the capsule or other retaining element that otherwise serves to separate the reactive agents may also provide a weighting function after inflation. Alternatively, one or more solids or liquids produced as reaction byproducts may serve to weigh or orient the volume-occupying subcomponent. As illustrated in FIGS. 11A and B, one manner in which remaining reactants and/or reactant byproducts may be caused to weigh or orient the volume-occupying subcomponent 400 comprises engineering all or part of the container 132 holding the reactants to be at least partially solid and/or liquid impermeable, for example engineering the container to function as a filter. In this manner the solid and/or liquid reactants and/or byproducts are at least partially confined in the container 132, resulting in the container 132 maintaining its weight sufficiently to influence the orientation of the volume-occupying subcomponent 400. For example, tiny holes may be made in the reactant container 132 (by means of a laser or other apparatus) to make the container 132 at least partially solid impermeable or such container may be designed to be gas permeable only. In addition, the reactant container 132 may also serve to keep inflation reactants in close proximity to facilitate their mixing for the generation of gas and the inflation of the volume-occupying subcomponent 400.

As a further example, the volume-occupying subcomponent may be formed of a shape-memory or thermo-elastic polymer designed to assume a volume-occupying shape when in its natural, low energy state. Such a volume-occupying subcomponent may initially assume a restricted or constrained form, of a size and shape for ingestion by a patient while causing minimal discomfort, through packaging of the subcomponent into a dissolvable or biodegradable material or other container. Once the shape-memory volume-occupying subcomponent enters the stomach, the chemical or temperature environment of the stomach causes the restrictive element to break or disintegrate, by dissolution, degradation or other means, allowing the volume-occupying subcomponent to expand to its natural state. Means for restricting such shape-memory volume-occupying subcomponent include, but are not limited to, a polysaccharide capsule. Devices according to the present embodiment may, but need not necessarily employ a cover or sheath. When employed, such cover or sheath may function to create an internal cavity within the device that is isolated from the exterior environment and/or contents of the stomach. Possible thermo-elastic or memory shaped polymers for the above embodiments include latex, silicon, polyurethane, ethylene vinyl acetate (EVA) and ethylene vinyl alcohol (EVOH).

As a further example, the volume-occupying subcomponent may be converted into its expanded state by the unfolding and/or expansion of a metal frame. Such frame may be formed from a memory metal, such as Nitinol, that is manufactured and treated to assume a configuration small enough to fit within the device in delivery form, and to transition to the shape of an expanded frame for the volume-occupying subcomponent at a temperature at or below body temperature, e.g., such temperature mediated expansion acts to deploy the volume-occupying subcomponent to its expanded state. In the case of a Nitinol frame, transition would occur at Nitinol's transition temperature which is modifiable by methods well known in the art. Devices according to the preferred embodiments may, but need not necessarily employ a cover or sheath. When employed, such cover or sheath may function to create an internal cavity within the device that is isolated from the exterior environment and/or contents of the stomach. In order to keep the frame in its small configuration prior to delivery, it may be necessary to store the device at a temperature below room temperature. Alternatively, the frame may be mechanically constrained following its manufacture/treating to maintain its small configuration, and the degradation/disintegration/disruption of such constraint may act as the trigger for expansion of the frame. Potential means for actuating the degradation/disintegration/disruption of such constraint may include any of the means described above for degradation/disintegration/disruption of a barrier between two chemical agents.

Figure 12:
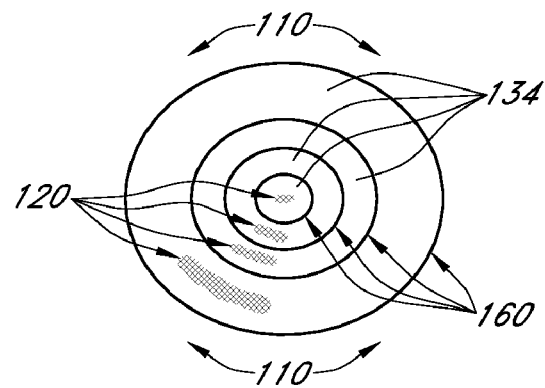
FIG. 12 is a cross-sectional view of an inflation subcomponent, in accordance with a preferred embodiment.
Figure 13:
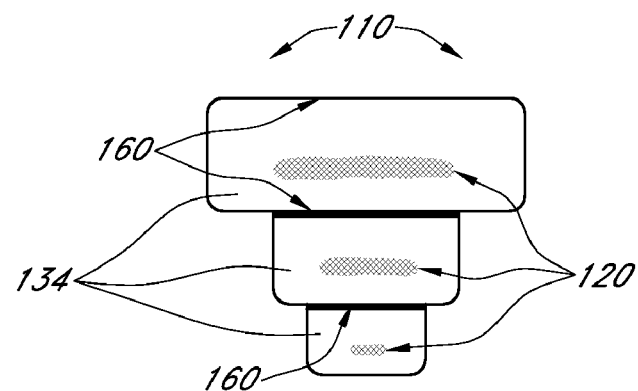
FIG. 13 is a cross-sectional view of an inflation subcomponent, in accordance with a preferred embodiment.
Figure 14:
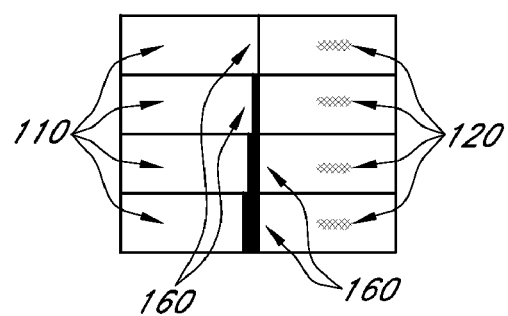
FIG. 14 is a cross-sectional view of an inflation subcomponent, in accordance with a preferred embodiment.

In certain embodiments, as illustrated in FIGS. 12-14, it may also be advantageous for the volume-occupying subcomponent to inflate gradually or in several steps over time. For example, if gas escapes the volume-occupying subcomponent prior to the desired deflation time, it would be beneficial for the device to reinflate in order to preserve it in its expanded state. To this end, in certain additional preferred embodiments, the volume-occupying subcomponent may contain one or more inflation subcomponents 100 that cause the volume-occupying subcomponent to inflate gradually or in steps over time. For example, the chemical components which react with one another to inflate with the volume-occupying subcomponent may be separated in several compartments 134 such that they will react gradually or in steps over time. For example, as illustrated in FIGS. 12-14, solid reactants 120 and liquid 110 may be separated by barriers 160 designed to degrade at different times. As a further example, a first barrier 160 may be designed to degrade several minutes following activation of the device while other barriers 160 may be designed to degrade over the course of days, weeks or months. Such degradable barriers 160 may be composed of any biodegradable or dissolvable material such as polyacetals or polyketals, with the degradation properties of the barrier 160 determined by altering the composition thereof. The commencement of the barrier 160 degradation process may be initiated by any of the trigger mechanisms described herein. Another way to achieve gradual inflation would be for one of the gas generating reactants to be produced gradually by the degradation of a precursor over time (e.g. over hours, days, weeks or months). For example, a polymer such as polylactic glycolic acid (PLGA) may be degraded over time to produce acid byproducts that react with another reactant contained in the volume-occupying subcomponent to generate gas. The commencement of the precursor degradation process may be initiated by any of the trigger mechanisms described herein.

Figure 42:
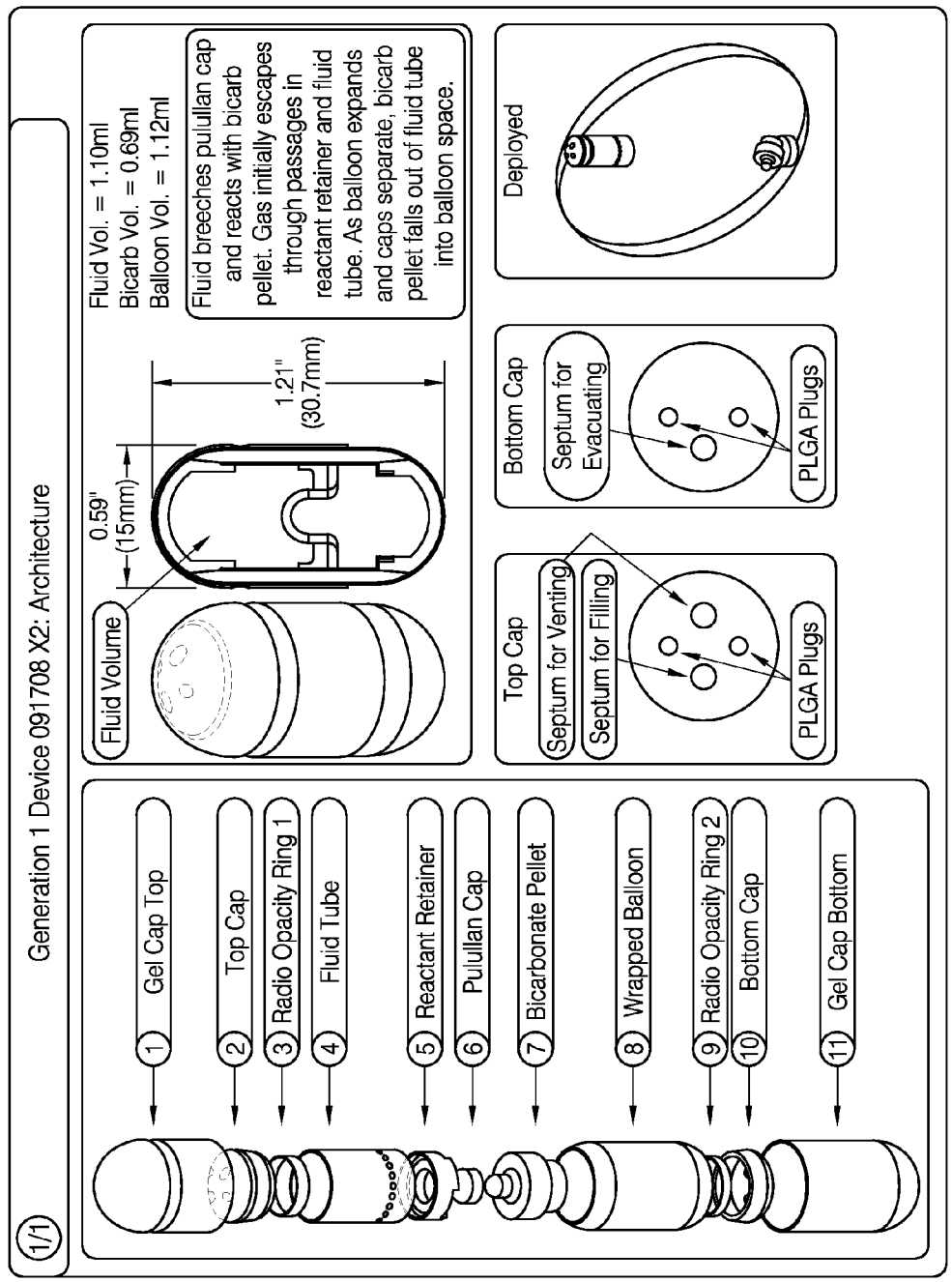
FIG. 42 is an illustration of various views of exemplary device in accordance with a preferred embodiment.
Figure 43A:
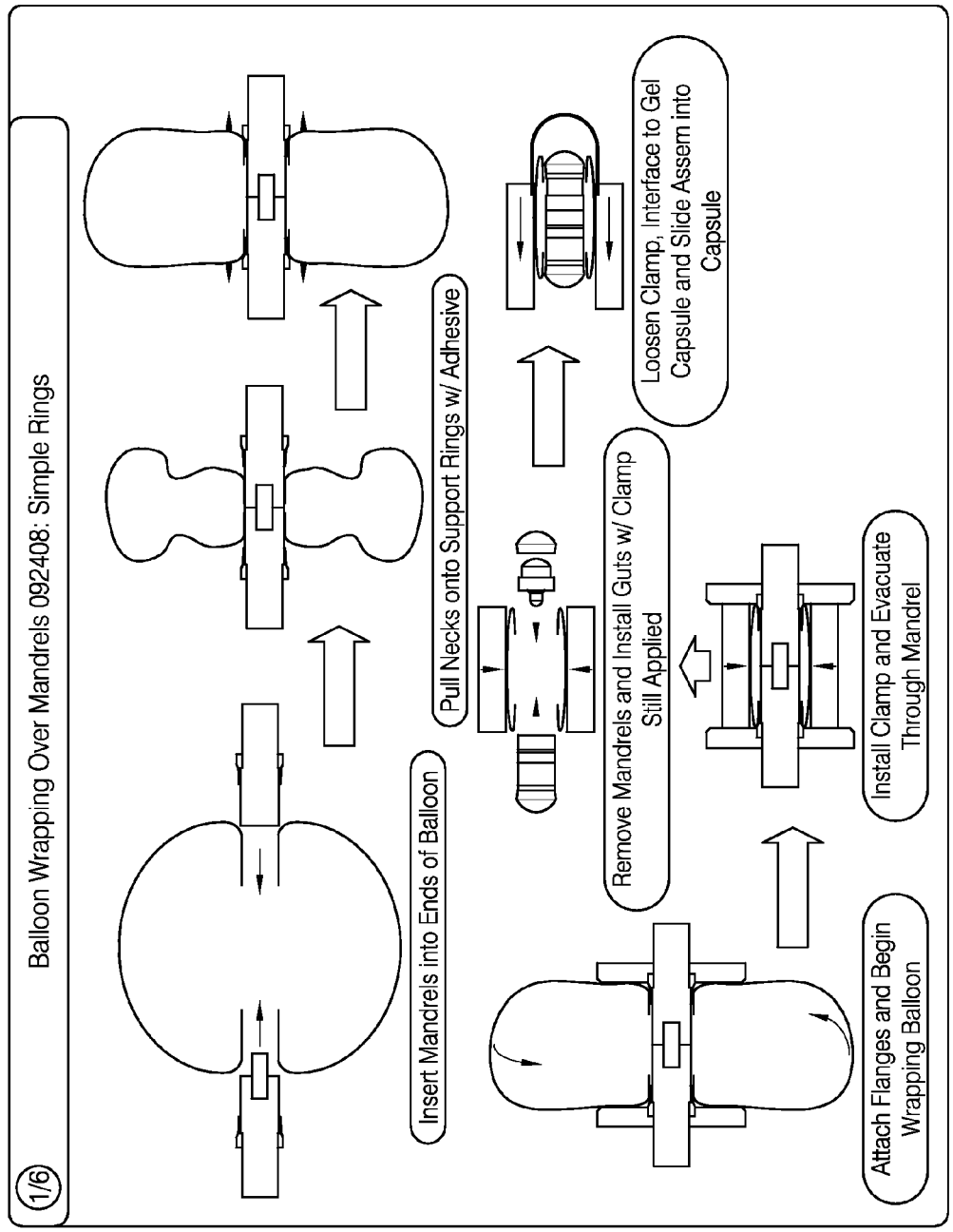
FIG. 43A-C is an illustration of various methods of assembling devices in accordance with a preferred embodiment.
Figure 43B:
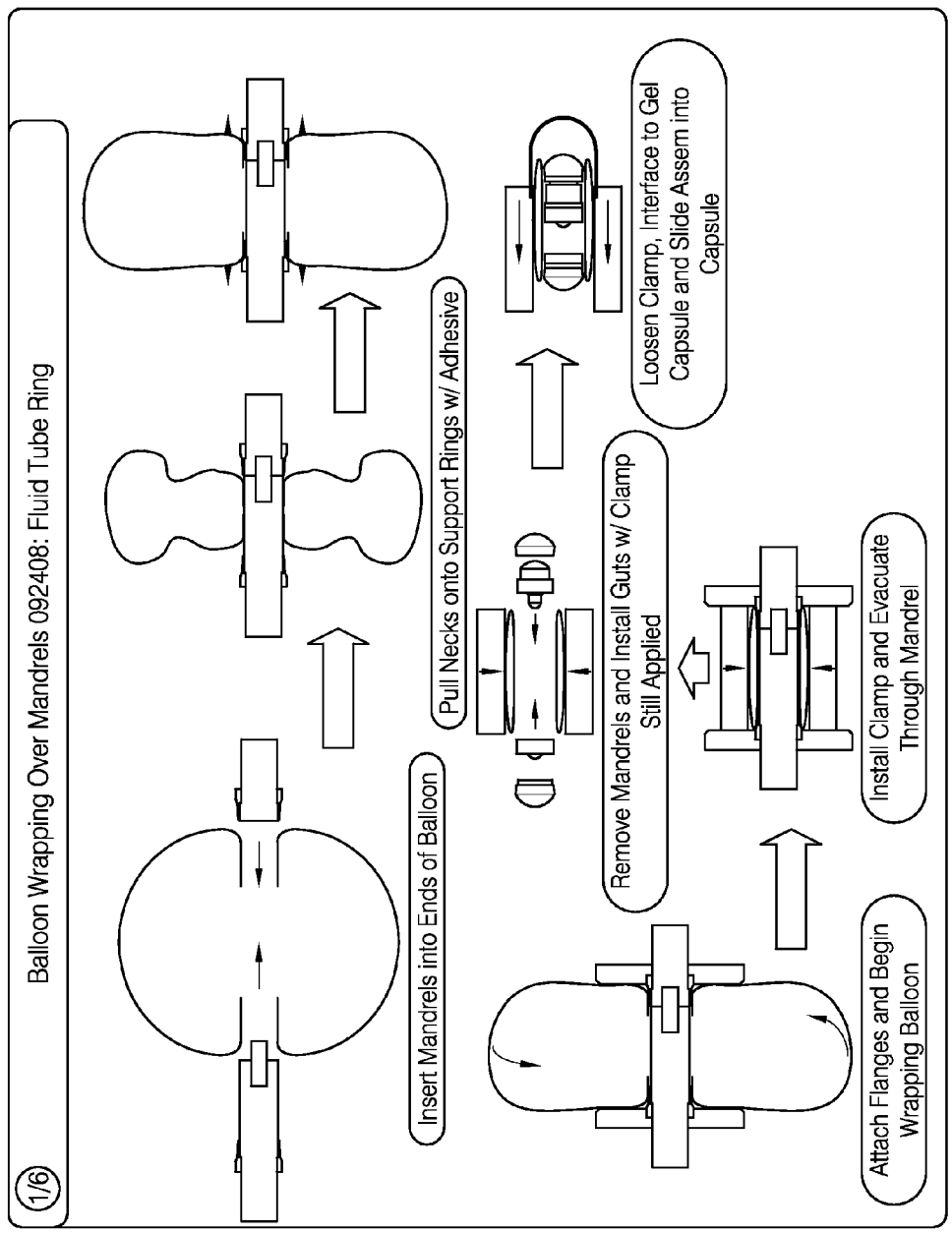
Figure 43C:
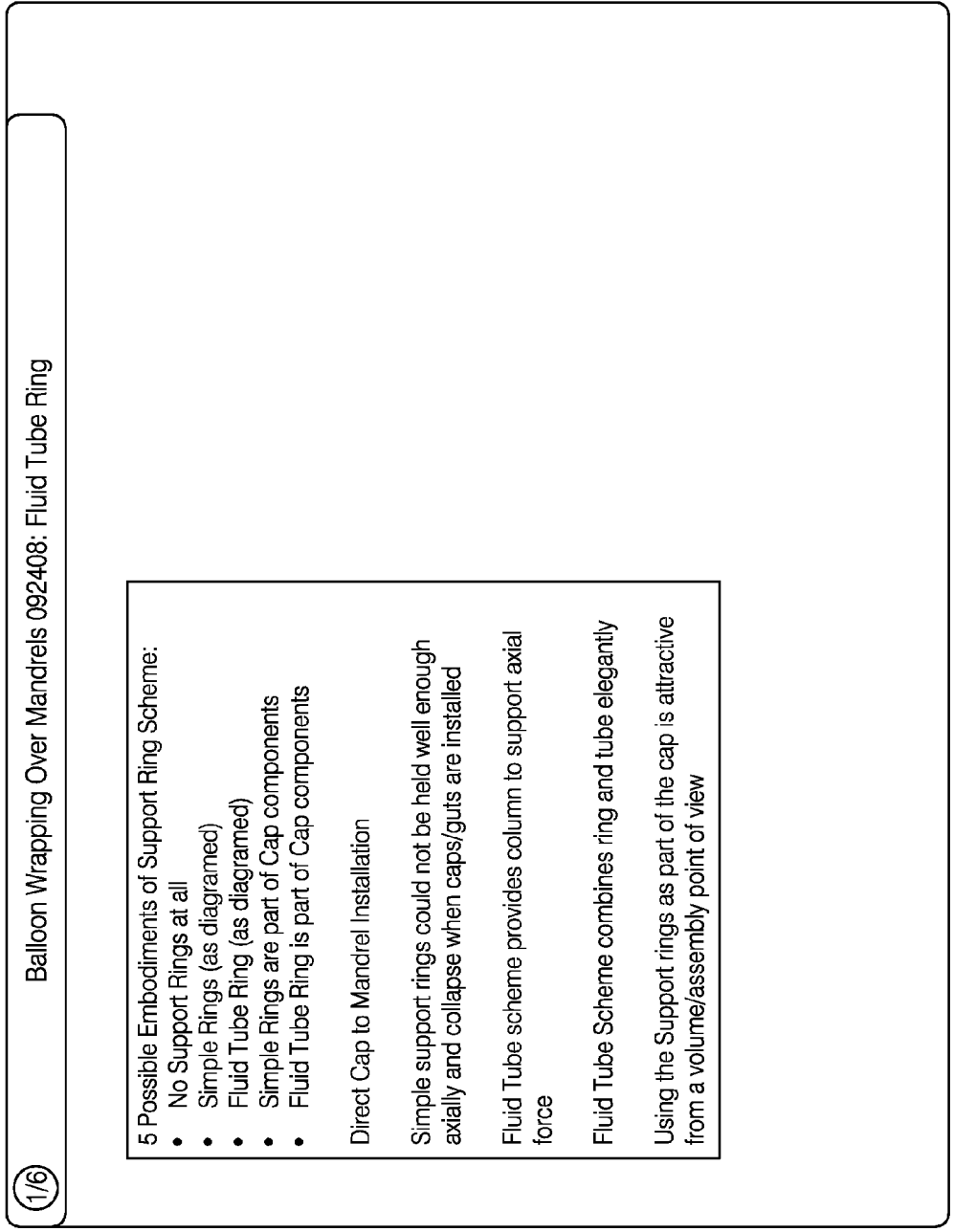

In other embodiments, it may be desirable that once the delivered device reaches the stomach, the volume-occupying subcomponent inflates quickly to a desired size in order to reduce the danger of the volume-occupying subcomponent passing through the pyloric sphincter following delivery. To achieve such a rapid inflation, one of the inflation agents, e.g. bicarbonate, may be deployed in such a manner so as to maximize its surface area. Accordingly, upon mixing of the inflation agents, a greater amount of gas may be generated at the beginning of the reaction, resulting in a more rapid expansion of the volume-occupying subcomponent earlier following delivery. Similarly, it may be advantageous for the inflationary reactants to be engineered such that a reaction between small portions of the reactants occurs initially to help to catalyze a larger reaction between the remaining reactants. Such initial smaller reaction may also be used to cause an initial expansion of the device to dislocate or move other components within the device into a state necessary or desirable for inflation or for the device's inflated state. For example, the reactants may be constructed such that, upon initiation of the inflation step, citric acid first comes into contact with a small concentration of carbonate, triggering an initial reaction that helps to mix the remaining reactants to initiate a larger reaction. FIG. 42 illustrates an embodiment of the device designed to provide for an initial smaller inflationary reaction that helps to catalyze a subsequent larger inflationary reaction and to initiate the movement of other components within the device to positions necessary or desirable for inflation or the device's inflated state. Alternatively, a reagent may be deployed so as to have an initially rapid rate of reaction and a subsequently decreasing rate. Such a variable rate of reaction and thereby inflation of the volume-occupying subcomponent may be achieved by deploying, for example, a solid reagent in the form of a compressed ball.

Figure 15B:
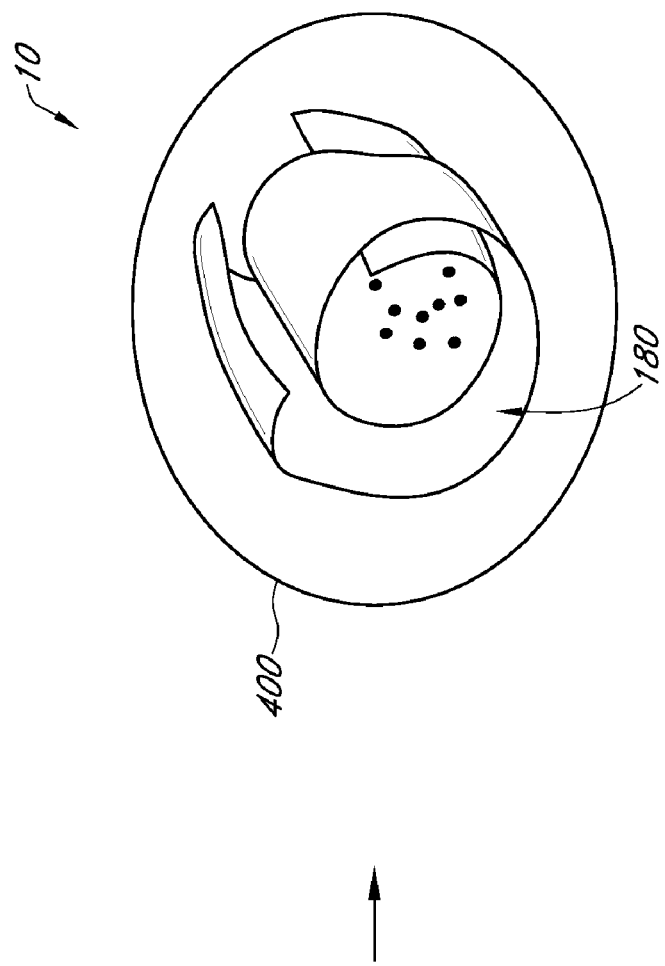
FIGS. 15A and B are cross-sectional views of an exemplary intragastric volume-occupying device and associated inflation subcomponent, in accordance with a preferred embodiment.
Figure 15A:
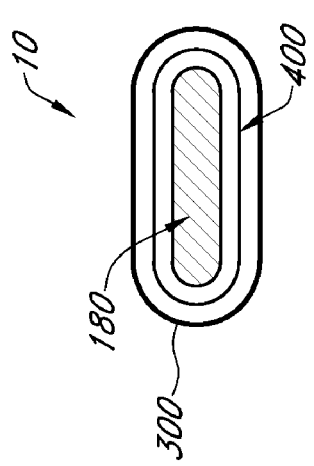

In another embodiment, illustrated in FIGS. 15A and 15B, the device may contain a wicking element 180 in proximity to the gas generating reactants that, once in contact with a liquid reactant, serve as a medium for the liquid reactant to travel on in order to contact the solid reactant to initiate the inflation reaction. FIG. 15A shows a cross-sectional view of the device 10 in the delivery state, and FIG. 15B shows a cross-sectional view the device 10 in the deployed or expanded state. Such an embodiment would be advantageous because it would facilitate the chemical reaction by facilitating contact between reactants, and it may also enable a more complete reaction by facilitating contact between a higher proportion of the reactants than could be accomplished in the absence of the wicking element 180. For example, the wicking element 180 may be composed of a hydrophilic material, such as paper, that allows a liquid reactant to travel to a solid reactant by means of capillary action. In another embodiment, the wicking element 180 may contain or be implanted with the solid reactant on all or a part of its surface.

It may also be advantageous for the device to contain subcomponents that aid in the mixing of inflation agents to increase the rate and/or completion of their reaction in order to increase the rate or degree of volume-occupying subcomponent inflation. This would be beneficial, for example, because it would allow the device to be engineered to contain a lesser quantity of reactants so that it can be configured to assume a smaller size, facilitating its swallowability and passage to the stomach. For example, methods of generating heat in the device using an external RF or magnet field source similar to those described can be used to heat the inflation agents to increase their mixing. For example, methods of generating electrical energy in the device using an external RF, magnet field, or pulsatile magnetic energy source similar to those described above can be used to power a mixing element proximate to the inflation agents. Such mixing element may be, for example, a pump. As another example, such mixing element may be one or more magnetophilic agents whose movement is stimulated by an external magnetic field or magnet pulses. In another embodiment, mixing of the inflation elements may be achieved by an external lithotripter emitting high-intensity acoustic pulses towards such elements. Any of the foregoing methods used to mix inflation elements may also be used to increase their association so as to enhance the reaction between them.

In another example, the barrier separating the chemical inflation agents is susceptible to disruption by lithotripsy techniques. Lithotripter, externally-applied, focused, high-intensity acoustic pulses, may be applied to the barrier to disrupt or otherwise breach the elements and thereby allow the chemical agents to mix and the balloon to inflate. The barrier may also be comprised of materials that resonate at a certain frequency such that when such frequency is applied using an external source such frequency will cause the barrier materials to oscillate sufficiently to disrupt or otherwise breach the elements and thereby allow the chemical agents to mix and the balloon to inflate. The range for such frequency would include the infrasonic, acoustic and ultrasonic frequency ranges. Materials that may be disrupted by lithotripsy or that may be designed to resonate at a certain frequency may include glass, ceramics, calcium, alkaline composites and/or brittle materials.

Deflation Subcomponents

According to preferred embodiments, deflation of the volume-occupying subcomponent is achieved without resort to invasive procedures. Deflation subcomponents may function as a programmed time based deflation in which, after a certain period of time has lapsed since deployment or delivery of the device, the device self-deflates, without external stimulus. Alternatively, deflation may be externally triggered by a stimulus applied by the physician. Devices according to the present invention may employ a combination of the deflation subcomponents to provide greater ease of operation and greater control and safety of the device.

Figure 16B:
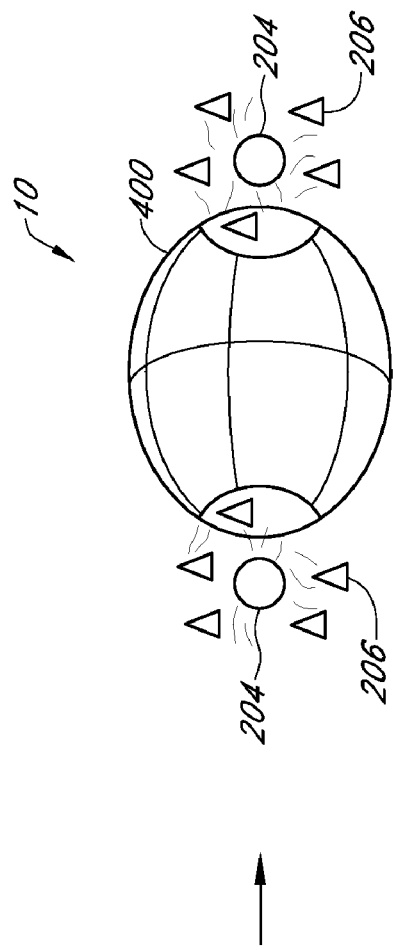
FIGS. 16A and B are perspective views of an exemplary intragastric volume-occupying device and associated deflation subcomponent in an inflated state, in accordance with a preferred embodiment.
Figure 16A:
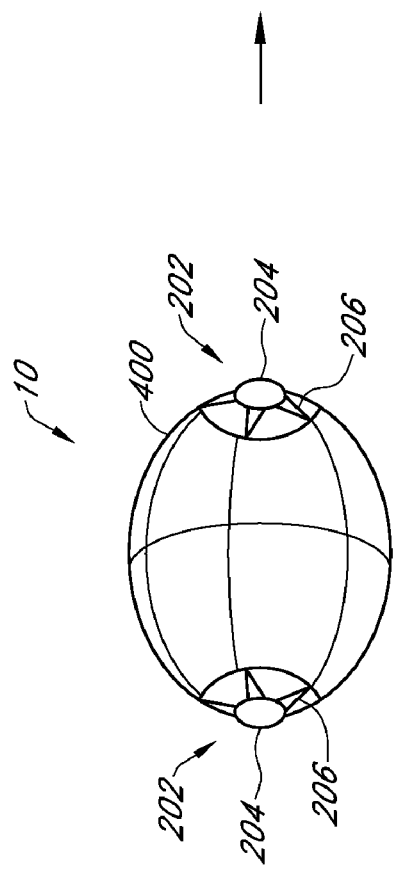

In a preferred embodiment, the volume-occupying subcomponent 400 may contain a biodegradable or dissolvable head 202 that upon degradation allows fluid to escape and the volume-occupying subcomponent 400 to deflate. The head 202 may be constructed in such a manner that disintegration of the head 202 materials from the volume-occupying subcomponent 400 accelerates after a degree of degradation has occurred. For example, as illustrated in FIGS. 16A and 16B, a first portion 204 of the head 202 may be designed to degrade faster than a second portion 206 of head 202 with the first portion 204 stabilizing the second portion 206 of the head 202 such that when the first portion 204 degrades, second portion 206 destabilize and is released from the head 202, thereby accelerating the deflation process. Examples of head 202 designs can include outer portions held together by a faster degrading centerpiece, a head 202 with a slower degrading outer half and faster degrading inner half. An inner portion may also be partially held together by a water soluble adhesive that, upon degradation of the outer half of the head, becomes in contact with the contents of the stomach, resulting in accelerated disintegration of the inner half of the head. FIGS. 16A, 16B also illustrate further embodiments in which the deflation subcomponent 200 may contain more than one head 202 through which fluid is released upon deflation.

In certain preferred embodiments, the degradable head may contain materials that are degraded by enzymes that are normally present in the stomach, such as pepsin or other proteases.

Alternatively, as illustrated in FIGS. 17A and 17B, the head 202 may incorporate a tension element 210, such as a spring, a degradable link 212, and one or more plug elements 214. The degradable link 212 serves to secure the tension element 210 around plug element 214 such that, upon degradation of the degradable link 212, tension element 210 releases all or part of plug element 214 from the head 202, thereby allowing for the escape of fluid from the volume-occupying subcomponent 400.

In a preferred embodiment, deflation subcomponents 200 may be employed that are susceptible to disruption by lithotripsy techniques. For example, as illustrated in FIGS. 18 and 19, the deflation subcomponent 200 may incorporate a trigger element 220 such as a small head, vial, or glass membrane in the wall of the volume-occupying subcomponent 400. Lithotripter, externally-applied, focused, high-intensity acoustic pulses, may be applied to the trigger element 220 to disrupt or otherwise breach the elements and thereby allow the inflation fluid to escape and the volume-occupying subcomponent 400 to deflate. The trigger element 200 may also be comprised of materials that resonate at a certain frequency such that when such frequency is applied using an external source such frequency will cause the materials to oscillate sufficiently to disrupt or otherwise breach the elements and thereby allow the inflation fluid to escape and the volume-occupying subcomponent 400 to deflate. The range for such frequency would include the infrasonic, acoustic and ultrasonic frequency ranges. Materials that may be disrupted by lithotripsy or that may be designed to resonate at a certain frequency may include glass, ceramics, calcium, alkaline composites and/or brittle materials.

In another preferred embodiment, the deflation subcomponent employs an externally applied magnetic field. For example, the deflation subcomponent may be configured such that a magnet field, introduced into the vicinity of the deployed device, causes a solenoid to close which in turn closes a circuit configured to generate heat when in a closed state. The generated heat in turn heats a temperature sensitive sealing element incorporated in the volume-occupying subcomponent wall. Upon achieving a predetermined temperature, the temperature sensitive sealing element is disrupted or breached and the fluid inside the volume-occupying subcomponent escapes, thereby deflating the volume-occupying subcomponent. Alternatively, a microfilm may be activated by the magnetic field and used to heat and disrupt the volume-occupying subcomponent.

As a further example, the deployed device may contain a pump that is actuated by pulsatile magnetic energy applied externally and that pumps fluid out of the volume-occupying subcomponent causing the volume-occupying subcomponent to deflate. Such actuation may be by means of a voltage electromagnetically induced by a conducting wire forming a closed loop connected to such pump.

As a further example, the wall or head of the volume-occupying subcomponent may contain a magnet, metal or other magnetophilic substance that, upon external application of a magnetic field, is disrupted or otherwise moved sufficiently to allow a breakage or opening in the volume-occupying subcomponent or head of the volume-occupying subcomponent sufficient for fluid inside of the volume-occupying subcomponent to escape, thereby deflating the volume-occupying subcomponent.

FIGS. 20A-D illustrate a further example in which the head 202 of the deflation subcomponent 200 may contain one or more valves 230, such as spool valves, that, upon external application of a magnetic field, is opened to allow fluid inside of the volume-occupying subcomponent 400 to escape, thereby deflating the volume-occupying subcomponent 400. FIG. 20A illustrates a top-view of the head 202 in which the valves 230 are closed. FIG. 20B illustrates a top-view of the head 202 in which the valves 230 are open. FIG. 20C illustrates a cross-section view of the head 202 in which the valves 230 are closed. FIG. 20C illustrates a cross-section view of the head 202 in which the valves 230 are open and the fluid inside the volume-occupying subcomponent 400 is flowing out from the volume-occupying subcomponent 400.

As a further example, one or more portions of the head of the volume-occupying subcomponent may be stabilized or held together by a magnetic field emanating from a magnet in the volume-occupying subcomponent. Upon application of an external degaussing or demagnetizing force, the magnetic field is sufficiently reduced or eliminated so as one or more portions of the head are destabilized to allow a breakage or opening in the volume-occupying subcomponent or head of the volume-occupying subcomponent. Destabilization or movement of the head upon elimination or reduction of the magnetic field may be aided by incorporating one or more spring loaded elements into the head that are constrained by the magnetic field.

A further embodiment provides for the deflation to occur by production of magnetic field gradients which will melt a hole in the side of the volume-occupying subcomponent sufficient to release the inflation fluid. A magnetic field can be created by current flowing through the coil of a relay which would alter micro switch contacts.

Alternatively, the device may employ a magnetized sealing element within or on the volume-occupying subcomponent. For example, a spring loaded sealing element may be incorporated into the wall of the volume-occupying subcomponent. Application of an external magnet field to the vicinity of the device within the patient will counter the spring loaded sealing element and thereby deflate the device.

In certain alternative preferred embodiments, the deflation subcomponent utilizes a chemical-based technique. For example, after the device has been deployed for a specific time period within the patient, the patient will ingest a substance designed to target and degrade the material from which the volume-occupying subcomponent is formed or a sealing element incorporated within the volume-occupying subcomponent. The degrading substance may be ingested by the patient in the form of a pill, capsule, or liquid. Preferably, the degrading substance is operable to cause deflation within a predictable, short period of time between 0 and 24 hours following administration of the degrading substance. For example, the all or part of the volume-occupying subcomponent wall or head may be composed of a polymer that is degraded by one or more specific enzymes or bacteria, with the degrading substance to be administered being the applicable enzyme or bacteria.

One embodiment of the deflation subcomponent utilizes a remotely adjustable implantable microchip which would open and close a valve controlling fluid within the volume-occupying subcomponent. This valve can also be opened using an electrokinetic pump actuation or by pressure activation.

In yet another embodiment, the deflation subcomponent is engineered with a power source and radiofrequency transformer such that an external wireless RF signal is able to be transformed into electric energy and create a voltage difference to deflate the volume-occupying subcomponent. For example, deflation may be achieved in this manner by means of a polymer microfilm adjacent to the wall of the volume-occupying subcomponent or the materials in the head of the volume-occupying subcomponent, the electric energy triggered by the RF signal causing such microfilm to melt a part of the wall or such materials sufficiently to cause a breach in the volume-occupying subcomponent to allow deflation. The RF signal may be received by means of an antenna adjacent to the power source. Alternatively, no power source may be required for the conversion of the RF signal to electric energy, for example by employing "ping and listen" technology.

In another embodiment, an RF signal may be employed to power a pump that causes deflation by pumping a fluid out of the volume-occupying subcomponent. Alternatively, an RF signal may be used to open a valve to release fluid from the volume-occupying subcomponent and thereby cause deflation.

In a further embodiment, the deflation subcomponent employs a light-absorbing compound such as a chromophore incorporated into a valve. Application of an appropriate light source functions to modify the valve composition in vivo. The modification results in a heating of the valve to a temperature at which the material ruptures, and thereby deflates. Light exposure to the barrier following administration of the device to the patient may be accomplished by exposing the barrier to a light source external to the volume-occupying subcomponent, e.g. by inserting an endoscope or wand with a light source at its end orally down the gastrointestinal tract and which then emits light at the valve.

In other embodiments, deflation of the volume-occupying subcomponent may be achieved, in part or entirely, through a change in the internal pressure in the volume-occupying subcomponent. For example, the volume-occupying subcomponent's internal pressure may activate a pneumatic valve in the volume-occupying subcomponent so as to open and release a fluid and deflate.

Figure 21A:
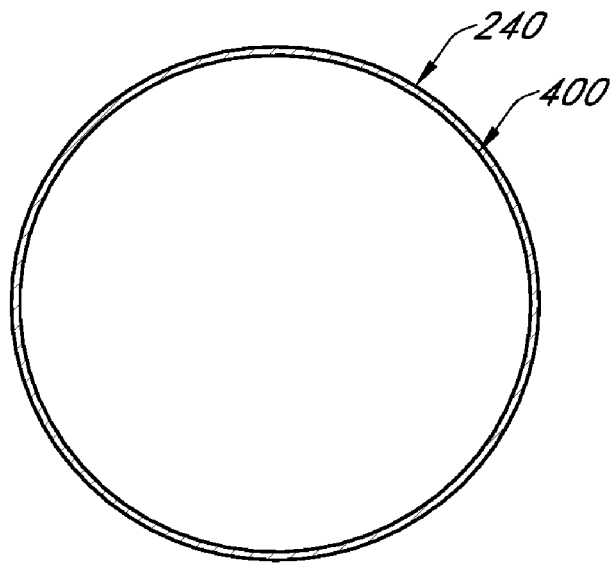
FIGS. 21A and B are cross-sectional views of a deflation subcomponent, in accordance with a preferred embodiment.
Figure 21B:
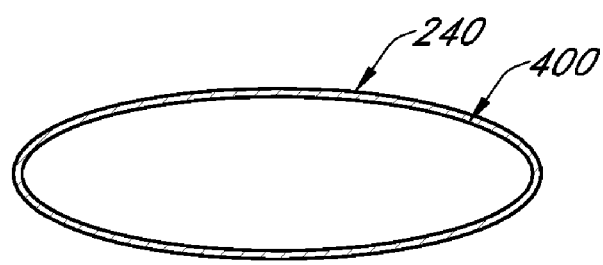

It may be advantageous to design the device in ways that improve the rate of deflation of the volume-occupying subcomponent or cause it to deflate more completely. To this end, as illustrated in FIGS. 21A and B, all or part of the volume-occupying subcomponent 400 may incorporate a elastomeric material (silicon, for example) that forms a sheath or wall 240 that applies a contracting force on the volume-occupying subcomponent 400 and facilitates deflation once the volume-occupying subcomponent 400 has been breached. FIG. 21A illustrates a volume-occupying subcomponent 400 in the inflated or deployed state that employs a sheath wall 240. The contraction force applied by sheath or wall 240 may be applied in an asymmetric manner to the volume-occupying subcomponent 400. For example, as illustrated in FIG. 21B, the contraction force may act primarily along a longitudinal axis such that the deflated volume-occupying subcomponent 400 has a first dimension that is greater than a second dimension.

It may be advantageous for the volume-occupying subcomponent to contain a duct valve or other type of valve that allows fluid to exit the volume-occupying subcomponent upon initiation of the deflation step but that permits little or no fluid to enter or flow back into the subcomponent.

Delivery Subcomponents

In the delivery state, devices according to the preferred embodiments employ a configuration that facilitates swallowing of the device while producing minimal discomfort to the patient. Preferably, the volume-occupying subcomponent is in a compressed configuration and other device subcomponents are sized so that the entire device may conform to the general shape of a capsule. As illustrated in FIGS. 2A-5B, in the delivery state, the device 10 may be configured in any number of shapes, including the following: round (see FIGS. 3A and B), oblong (see FIGS. 2A and B), oval (see FIGS. 5A and B), suppository-shaped, mushroom-shaped, finger-shaped, bullet-shaped or torpedo-shaped (see FIGS. 4A and B). A bullet-shaped capsule, for example, may contain the contents of the volume-occupying subcomponent more efficiently.

In a preferred embodiment, the device is fitted into a standard sized gelatin capsule. The capsule may be formed of a material that has a know rate of degradation such that the device will not be released from the capsule or otherwise deployed prior to entry into the stomach. For example, the capsule materials may include one or more polysaccharide and/or one or more polyhydric alcohols.

Alternatively, the device, in its delivery state, may be coated in a substance that confines the device in its delivery state while also facilitating swallowing. The coating may be applied by a dipping, sputtering, vapor deposition, or spraying process which may be conducted at an ambient or positive pressure.

In certain preferred embodiments, the encapsulated or coated device is lubricated or otherwise treated so as to facilitate swallowing. For example, the encapsulated or coated device may be wetted, heated, or cooled, prior to swallowing by the patient. Alternatively, the encapsulated or coated device may be dipped in a viscous substance that will serve to lubricate the device's passage through the esophagus. Examples of possible coatings would be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may also be applied by a sputtering, vapor deposition or spraying process.

In additional embodiments the coating or capsule is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

In certain embodiments, the capsule may be weighted at a certain end in order for it to be oriented appropriately when it is administered, as it travels down the esophagus, and/or when it is in the stomach. The weighting components may include polymer materials or inflation reactants.

Figure 22A:
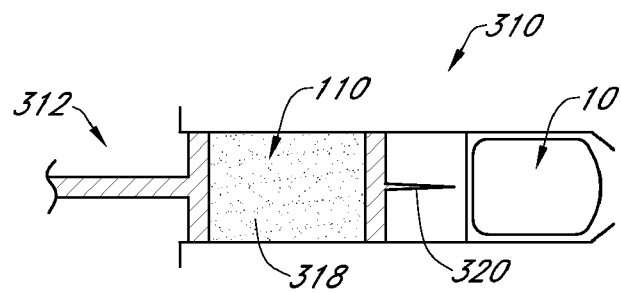
FIGS. 22A-C are cross-sectional views of a delivery subcomponent, in accordance with a preferred embodiment.
Figure 22B:
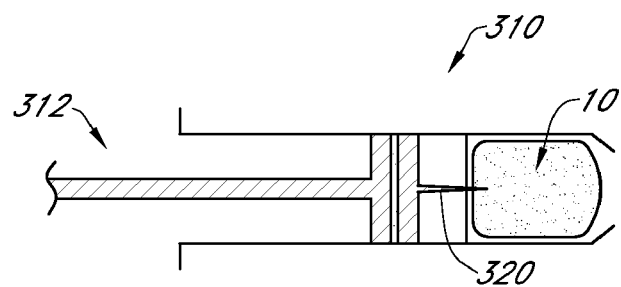
Figure 22C:
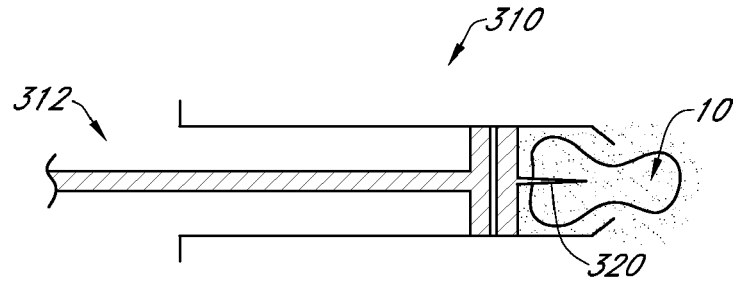
Figure 23:
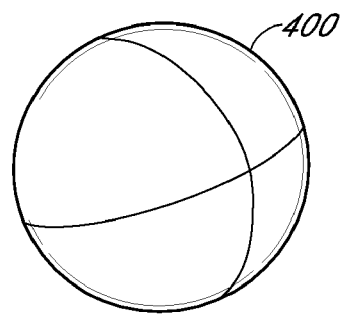
FIG. 23 is a perspective view of an exemplary volume-occupying subcomponent in an expanded state, in accordance with a preferred embodiment.
Figure 24:
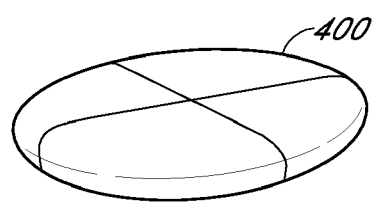
FIG. 24 is a perspective view of an exemplary volume-occupying subcomponent in an expanded state, in accordance with a preferred embodiment.
Figure 25:
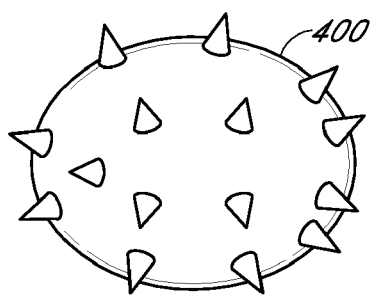
FIG. 25 is a perspective view of an exemplary volume-occupying subcomponent in an expanded state, in accordance with a preferred embodiment.

It may advantageous for an administrator of the device to use a delivery tool 310 for delivering the device 10 to the mouth or facilitating its passage through the esophagus in the optimal orientation. A delivery tool 310 may enable the device administrator to inject the device 10 with one or more inflation agents as the device 10 is being administered to the patient. In a preferred embodiment, such injection may be accomplished in the same mechanical action(s) of the administrator that are employed to release the device 10 from the delivery tool 310 into the mouth or esophagus. For example, with reference to FIG. 22A, the delivery tool 310 may include a plunger 312, a reservoir 318 having a liquid 110, and an injection needle 320. As shown in FIGS. 22B and C, the administrator pushes the plunger 312 which, either in sequence or approximately simultaneously, forces the injection needle 320 into the device 10 and thereby injects the liquid 110 contained in reservoir 318 into the device 10. Subsequent application of force to the plunger 312 pushes the device out of the delivery tool 310 and into the desired location within the patient. Furthermore, the delivery tool 310 may also include a subcomponent that administers an anesthetic or lubricant into the patient's mouth or esophagus to ease the swallowability of the device.

It may be advantageous for the administrator of the device to have a means of retrieving the device if it were to get stuck in the patient's esophagus following administration. Accordingly, certain embodiments of the device in its delivery state may include a string with one end attached to the device and with the other end able to be held by the administrator. The string may be attached to the device firmly enough to allow the administrator to exert enough force on the string to pull the device from the patient's esophagus if it is lodged there. The string would be long enough to allow the device to reach the patient's stomach while still having the other end held by the administrator. The string may be attached to the device in such a manner that it detaches within minutes after the device is in the stomach. For example, the string may be attached to the device by means of a water or stomach acid soluble adhesive.

Volume-Occupying Subcomponent

The volume-occupying subcomponent of the preferred embodiments is generally formed of a flexible material forming a wall which defines an exterior surface and an interior cavity. Various of the above-described subcomponents may be either incorporated into the wall or interior cavity of the volume-occupying subcomponent. FIGS. 23-32 are perspective views of various volume-occupying subcomponents 400. As shown, volume-occupying subcomponent 400 will vary in size and shape according to the patient's internal dimensions and the desired outcome. The volume-occupying subcomponent 400 may be engineered to be semi-compliant, allowing the volume-occupying subcomponent 400 to stretch or expand with increases in pressure and/or temperature.

It may advantageous for the volume-occupying subcomponent 400 to orient itself in a certain position and/or in a certain area of the stomach in order, for example, to induce satiety by interacting with a certain area in the stomach or to avoid interacting with a certain area of the stomach that would cause nausea. Accordingly, the volume-occupying subcomponent 400 may be designed in one or more ways to achieve a desired orientation/position. For example, the volume-occupying subcomponent 400 may contain a second component, such as a ring, that inflates around all or a portion of the volume-occupying subcomponent 400 and that facilitates the desired orientation/position of the volume-occupying subcomponent 400.

Figure 26:
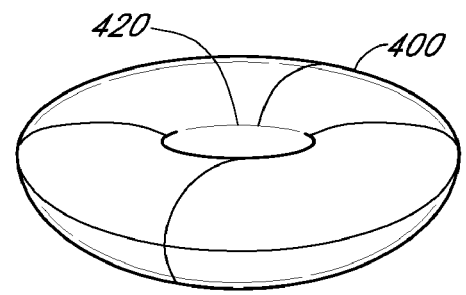
FIG. 26 is a perspective view of an exemplary volume-occupying subcomponent in an expanded state, in accordance with a preferred embodiment.
Figure 27:
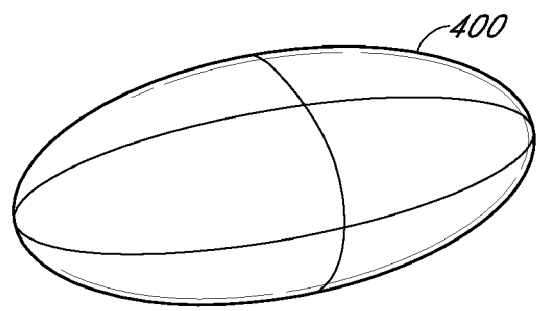
FIG. 27 is a perspective view of an exemplary volume-occupying subcomponent in an expanded state, in accordance with a preferred embodiment.
Figure 28:
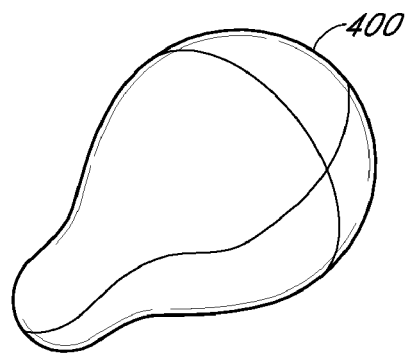
FIG. 28 is a perspective view of an exemplary volume-occupying subcomponent in an expanded state, in accordance with a preferred embodiment.
Figure 30:
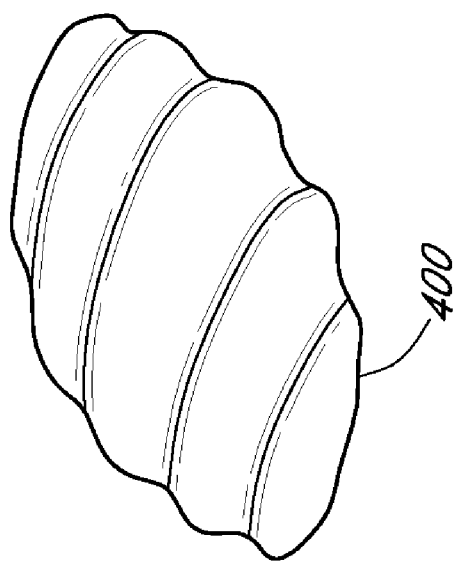
FIG. 30 is a perspective view of an exemplary volume-occupying subcomponent in an expanded state, in accordance with a preferred embodiment.
Figure 29:
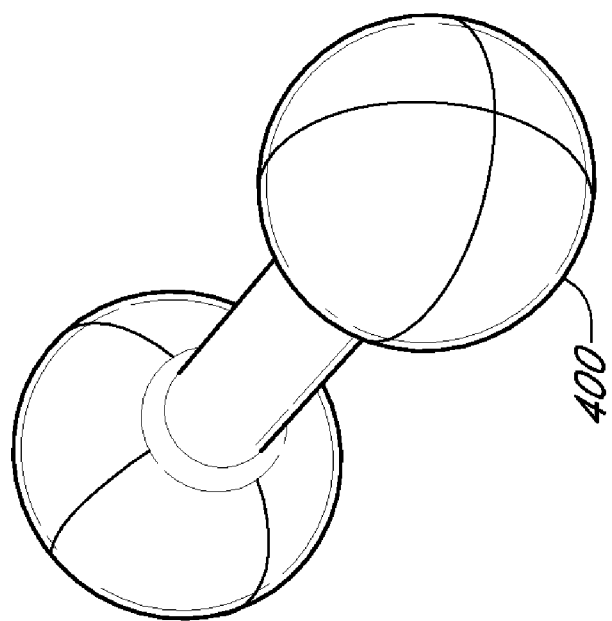
FIG. 29 is a perspective view of an exemplary volume-occupying subcomponent in an expanded state, in accordance with a preferred embodiment.
Figure 32:
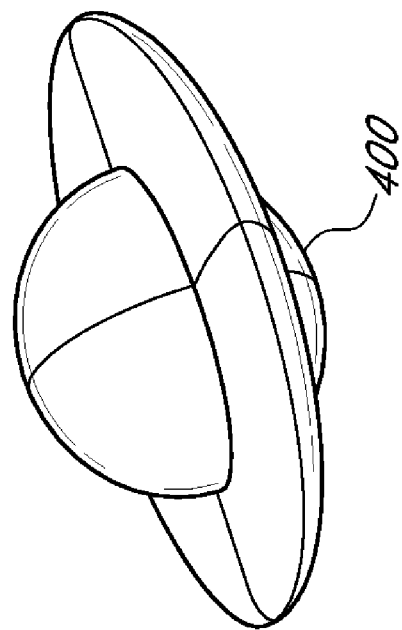
FIG. 32 is a perspective view of an exemplary volume-occupying subcomponent in an expanded state, in accordance with a preferred embodiment.
Figure 31:
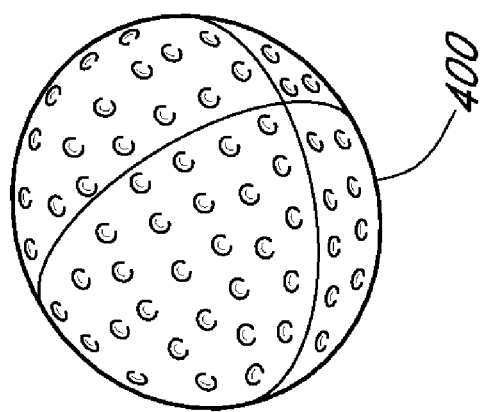
FIG. 31 is a perspective view of an exemplary volume-occupying subcomponent in an expanded state, in accordance with a preferred embodiment.
Figure 34:
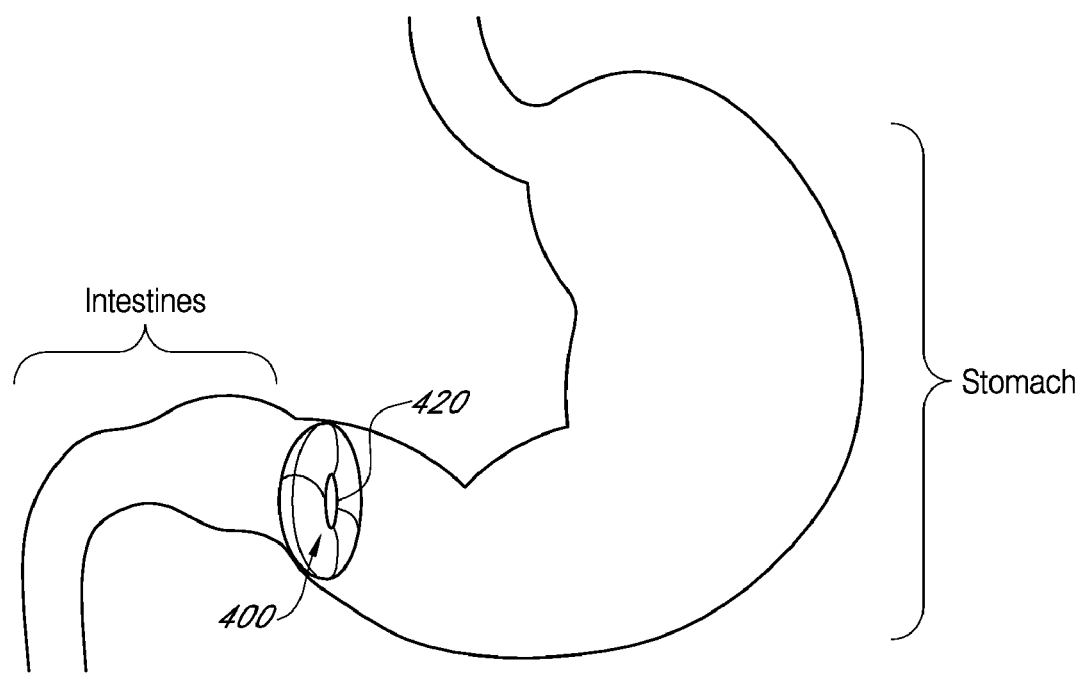
FIG. 34 is a perspective view of an exemplary volume-occupying subcomponent in an expanded state deployed within a patient's stomach, in accordance with a preferred embodiment.

Alternatively, the volume-occupying subcomponent 400 may be constructed to be donut-shaped, see FIGS. 26 and 34, with a hole 420 in the middle of it, and may be weighted and shaped in such a way that it orients in the stomach to cover all or part of the pyloric sphincter, similar to a check valve. The hole 420 in the middle of the volume-occupying subcomponent 400 would then serve as the primary passage for the contents of the stomach to enter the small intestine, limiting the passage of food out of the stomach and inducing satiety by reducing gastric emptying. Volume-occupying subcomponent 400 may be manufactured with different-sized donut-holes according to the degree that gastric emptying is desired to be reduced. Delivery, inflation and deflation of the volume-occupying subcomponent 400 may be accomplished by any of the methods described above.

It would be advantageous for the volume-occupying subcomponent wall to be both high in strength and thin. Accordingly, the volume-occupying subcomponent wall materials may be manufactured with a biaxial orientation that imparts a high modulus value to the volume-occupying subcomponent.

In one embodiment, a device according to the present invention is constructed of a polymeric substance such as polyurethane, polyethylene terephthalate, polyethylene naphthalate, polyvinyl chloride (PVC), Nylon 6, Nylon 12, or polyether block amide (PEBA). The volume-occupying subcomponent may be coated with one or more layers of substances that aid in achieving greater gas-barrier characteristics, such as a thermoplastic substance.

Preferably, the gas-barrier materials have a low permeability to carbon dioxide or other fluids that may be used to inflate the volume-occupying subcomponent. The barrier layers should have good adherence to the base material. Preferred barrier coating materials include biocompatible poly(hydroxyamino ethers), polyethylene naphthalate, polyvinylidene chloride (PVDC), saran, ethylene vinyl alcohol copolymers, polyvinyl acetate, silicon oxide (SiOx), acrylonitrile copolymers or copolymers of terephthalic acid and isophthalic acid with ethylene glycol and at least one diol. Alternative gas-barrier materials may include polyamine-polyepoxides. These materials are commonly acquired as a solvent or aqueous based thermosetting composition and are generally spray-coated onto a preform and then heat-cured to form the finished barrier coating. Alternative gas-barrier materials which may be applied as coatings to the volume-occupying subcomponent include metals such as silver or aluminum. Other materials that may be used to improve the gas impermeability of the volume-occupying subcomponent include, but are not limited to, gold or any noble metal, PET coated with saran, conformal coatings and the like, as listed, for example, in Table 1.

In certain preferred embodiments, the volume-occupying subcomponent is injection, blow or rotational molded. Either immediately following such molding, or after a period of curing, the gas-barrier coating may be applied.

In another embodiment, the intragastric volume-occupying subcomponent is formed using a Mylar polyester film coating silver, aluminum or kelvalite as a metallicized surface, to improve the gas impermeability of the volume-occupying subcomponent.

In the event that the volume-occupying subcomponent's wall is composed of multiple layers of materials, it may be necessary to use certain substances or methods to connect, attach or hold together such multiple layers. Such substances can include a solvent or an ether-based adhesive. Such multiple layers may also be heat-bonded together. Once such layers are attached together to form (for example) a sheet of material to be made into a volume-occupying subcomponent, it may also be necessary to apply additional treatment steps to such material to allow it to seal together (for example, by application of a certain degree of heat and pressure) in order to be made into a volume-occupying subcomponent. Accordingly, it may be advantageous to include as an additional layer in the volume-occupying subcomponent certain materials that seal. For example, a volume-occupying subcomponent comprised of a combination of PET and SiOx layers, which impart favorable mechanical and gas impermeability characteristics to the volume-occupying subcomponent, may be sealed by including a layer of sealable polyethylene in such volume-occupying subcomponent.

According to another embodiment of the preferred embodiments, the functionality of the volume-occupying subcomponent and the deflation component is combined either in part or in whole. For example, the volume-occupying subcomponent may be formed of a substance that is degraded within the stomach over a desired period of time. Once the degradation process has formed a breach in the wall of the volume-occupying subcomponent, the volume-occupying subcomponent deflates, continues to degrade and passes through the remainder of the digestive tract.

Preferably, an automated process is employed that takes a fully constructed volume-occupying subcomponent, evacuates all of the air within the interior cavity and folds or compresses the volume-occupying subcomponent into the desired delivery state. For example, the evacuation of air from the volume-occupying subcomponent may be actuated by vacuum or mechanical pressure (e.g. rolling the volume-occupying subcomponent). In certain embodiments, it is desirable to minimize the number of creases produced in the volume-occupying subcomponent when in the delivery state.

Figure 33:
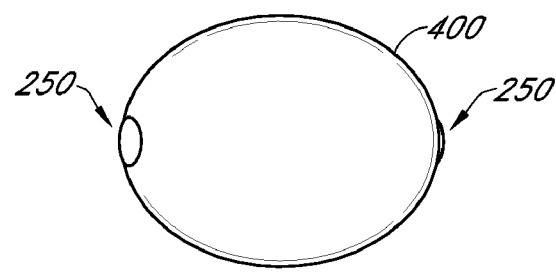
FIG. 33 is a perspective view of an exemplary volume-occupying subcomponent in an expanded state, in accordance with a preferred embodiment.

In another embodiment, illustrated in FIG. 33, deflation of the volume-occupying subcomponent 400 may be achieved through one or more injection site 250 within the wall of the volume-occupying subcomponent may be used. For example, two self-sealing injection sites can be incorporated at opposite sides of the volume-occupying subcomponent, see FIG. 33. The volume-occupying subcomponent may be positioned within a fixture that employs two small-gauge needles to evacuate the air from the volume-occupying subcomponent.

In one embodiment, the self-sealing injection sites may further be used to insert chemical elements of the inflation subcomponent into the interior of the volume-occupying subcomponent. After injection of the chemical elements into the volume-occupying subcomponent, the same needles may be used to perform evacuation of the volume-occupying subcomponent.

It may be desirable that the volume-occupying subcomponent is packed into the delivery state under, for example, a negative vacuum pressure or under a positive external pressure.

The volume-occupying subcomponent wall materials may also be engineered to, once they are initially punctured or torn, tear relatively easily from the point of such puncture or tear. Such properties would, for example, be advantageous if deflation of the volume-occupying subcomponent were initiated by a tearing or puncturing of the volume-occupying subcomponent wall, since such initial tear or puncture may then increase in scope, hastening and/or maximizing the deflation process.

The volume-occupying subcomponent may also be coated by a lubricious substance that facilitates its passage out of the body following its deflation. Examples of possible coatings would be any substances with lubricious and/or hydrophilic properties and include glycerine, polyvinylpyrrolidone (PVP), petroleum jelly, aloe vera, silicon-based materials (e.g. Dow 360) and tetrafluoroethylene (TFE). The coating may be applied by a dipping, sputtering, vapor deposition or spraying process which may be conducted at an ambient or positive pressure.

Tracking and Visualization Subcomponent

It may also be beneficial to implement tracking and visualization functionality into devices according to the present inventions. Due to the non-invasive nature of the present device, physicians may desire to determine, or confirm, the location and orientation of the device prior to inflation or during the course of treatment.

Figure 35:
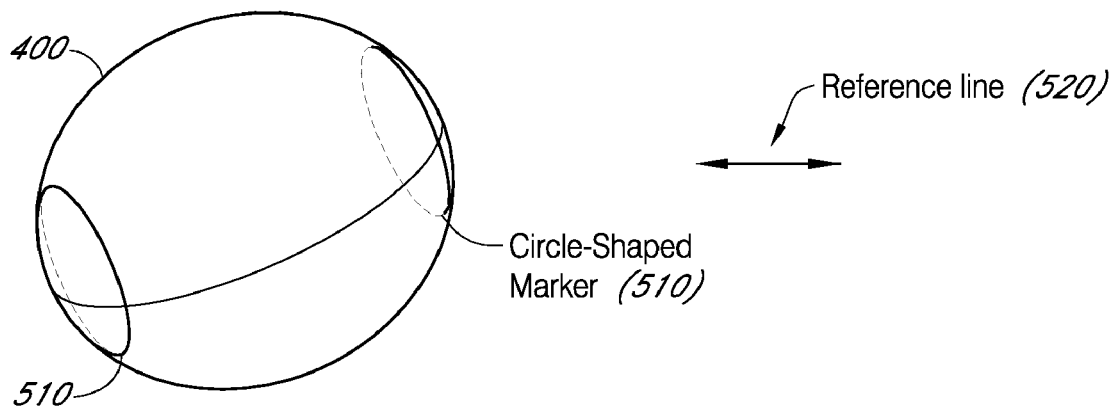
FIG. 35 is a perspective view of an exemplary visualization and tracking subcomponent in an expanded state, in accordance with a preferred embodiment.
Figure 36:
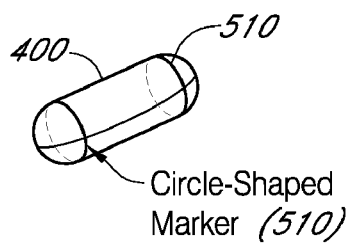
FIG. 36 is a perspective view of an exemplary visualization and tracking subcomponent in a deflated or contracted state, in accordance with a preferred embodiment.
Figure 37:
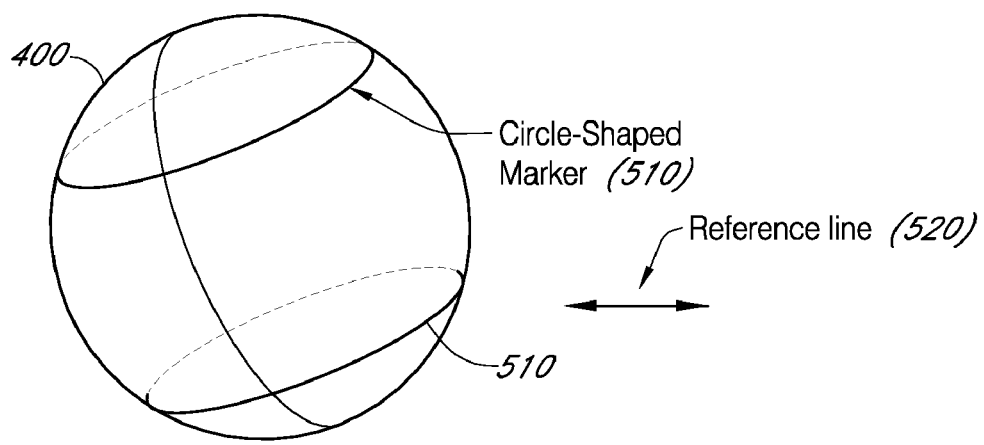
FIG. 37 is a perspective view of an exemplary visualization and tracking subcomponent in an expanded state, in accordance with a preferred embodiment.

In one embodiment, the volume-occupying subcomponent incorporates a barium sulfate or other radioopaque marker, e.g., a metallic substance. The marker may be implemented so as to form an identifiable geometric pattern on the inflated volume-occupying subcomponent when imaged or otherwise viewed on x-ray or other visualization equipment. For example, the marker may form a circular stripe at the equator and/or a stripe around each pole of the volume-occupying subcomponent. As shown in FIG. 35, the markers 510 form expanded circles and are positioned relatively far apart, indicating that the volume-occupying subcomponent 400 is in the deployed or inflated state. The approximately horizontal position of the markers 510 indicates that the axes of the volume-occupying subcomponent 400 that are bounded by the markers 510 are approximately parallel with respect to the illustrated reference line 520. In FIG. 36, the markers 510 form condensed circles positioned relatively close together, indicating that the volume-occupying subcomponent 400 is in a deflated state. In FIG. 37, the distance between the markers 510 indicates that the volume-occupying subcomponent 400 is inflated, and their approximately vertical position indicates that the axis of the volume-occupying subcomponent 400 that is bounded by the markers 510 is approximately perpendicular with respect to the illustrated reference line 520.

Alternatively, the marker may be applied to the volume-occupying subcomponent when the volume-occupying subcomponent is in a creased or folded state such that when the volume-occupying subcomponent is in its deflated state the marker appears concentrated when viewed on visualization equipment, and when the volume-occupying subcomponent is inflated the marker appears less concentrated when viewed on visualization equipment. Alternatively, the marker may be applied or incorporated into the volume-occupying subcomponent so as to facilitate identification and location of the various subcomponents of the device, such as a valve, head, or weight. The marker may be printed or painted onto a surface of the volume-occupying subcomponent or between layers of the material forming the volume-occupying subcomponent. Alternatively, a metal coating as described below may be used as a marker to identify and/or locate the volume-occupying subcomponent. Metal coatings for visualizing the volume-occupying subcomponent may include silver, gold, tantalum or any noble metal. Alternatively, the marker may be applied to an elastomeric sleeve that covers all or part of the volume-occupying subcomponent.

In another embodiment, the volume-occupying subcomponent incorporates a subcomponent that changes mechanically upon inflation of the volume-occupying subcomponent, which mechanical change can be visualized using x-ray or other visualization equipment. For example, a mechanical portion of the volume-occupying subcomponent containing a visualization marker may elongate upon an increase in pressure in the volume-occupying subcomponent.

Alternatively, a marker may be formed using a metalized mesh located between layers of the material from which the volume-occupying subcomponent is constructed. The pattern or patterns formed by the imbedded marker will appear when the volume-occupying subcomponent is in an inflated, deployed state.

In another embodiment, other visualization approaches are utilized as position markers including an infrared LED tag, ultraviolet absorbing compounds, fluorescent or colored compounds and a metalized strip on the volume-occupying subcomponent that is positioned in a pattern.

It is envisioned that marker materials may be incorporated into the volume-occupying subcomponent to facilitate various visualization techniques such as, for example, MRI, CT and ultrasound.

The volume-occupying subcomponent may also contain a dye or marker that is released upon deflation to indicate that the volume-occupying subcomponent cavity has been breached. Such dye or marker may, for example, be apparent in the patient's urine as an indication that the volume-occupying subcomponent has begun to deflate.

In yet further embodiments, microchips and other components employing electronic modalities may be used to locate and identify a device. Microchips analogous to those utilized for the identification of pets may be used to communicate device specific information and its approximate location. For example, a Wheatstone or other bridge circuit may be incorporated into the device and, together with RF "ping and listen" technology may be used as part of a system to determine the device's approximate location and measure and communicate device specific information. Such device specific information can include internal volume-occupying subcomponent pressure, which can indicate the degree of inflation of the volume-occupying subcomponent.

In yet further embodiments, mechanical, chemical, visual and other sensors may be included as part of the device to measure, record and/or transmit information relating to the device and/or the patient's internal environment. For example, the device may contain a camera or any of the other imaging and transmission components of a Pillcam device. As an additional example, the device may contain sensors that measure, record and/or transmit information relating to stomach pH, stomach pressure, hormone levels, organ health, and organ safety.

Drug Delivery Subcomponent

It is also envisioned that the device of the preferred embodiments may further achieve the objective of delivering and administering various pharmaceutical therapies and treatments. Pharmaceutical substances may be incorporated into the material forming the volume-occupying subcomponent, into degradable pockets formed on the interior or exterior surfaces of the volume-occupying subcomponent, and/or coated on the outside of the volume-occupying subcomponent. Alternatively or additionally, pharmaceutical substances may be incorporated into or on one or more of the various other subcomponents of the device.

Figure 38A:
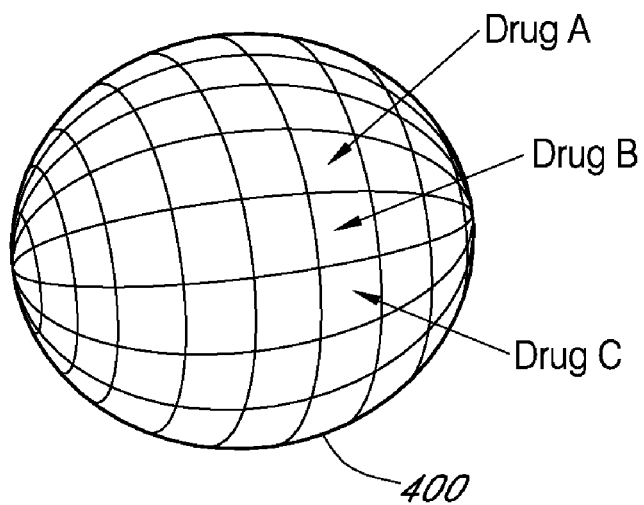
FIGS. 38A and B are perspective views of exemplary drug delivery subcomponents in expanded states, in accordance with a preferred embodiment.
Figure 38B:
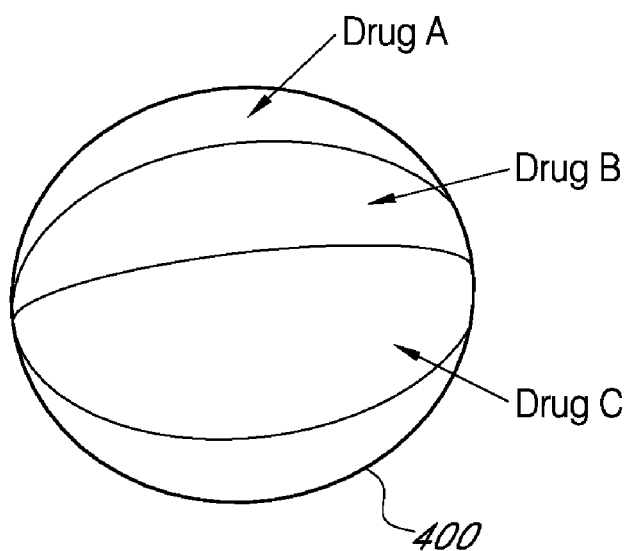
Figure 39A:
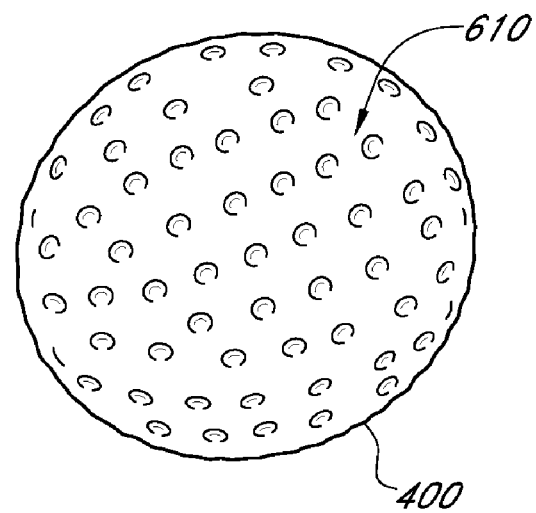
FIGS. 39A and B are perspective views of exemplary drug delivery subcomponents in expanded states, in accordance with a preferred embodiment.
Figure 39B:
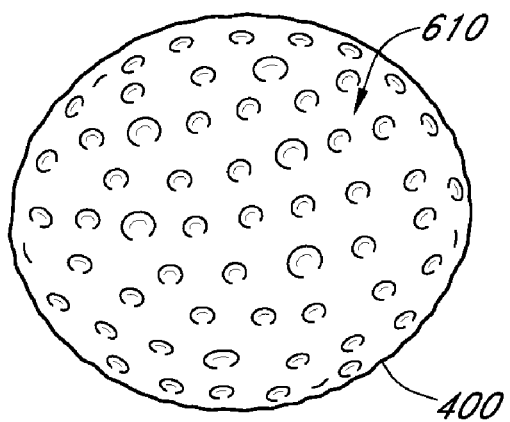

For example, FIGS. 38A and B illustrate how different drugs, A, B, and C, may be applied in different regions on the surface of the volume-occupying subcomponent 400. Alternatively, the outside of the volume-occupying subcomponent may be comprised of a microporous or meshed exterior designed to facilitate deposition and release of drug materials. FIGS. 39A and B show a volume-occupying subcomponent 400 containing a mesh or microsphere 610 like surface where drugs may be deposited or embedded.

Figure 40B:
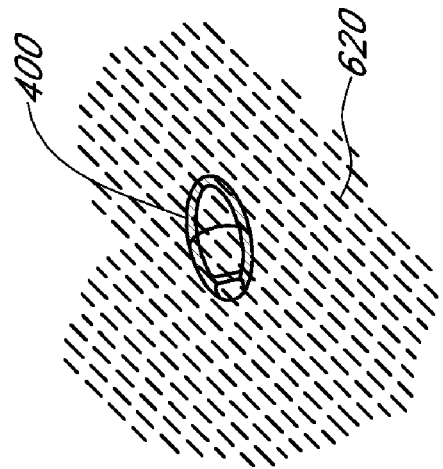
FIGS. 40A and B are perspective views of exemplary drug delivery subcomponents, in accordance with a preferred embodiment.
Figure 40A:
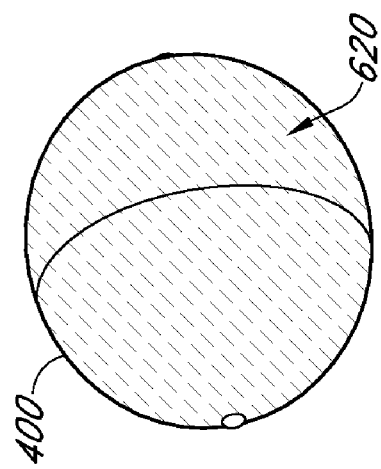
Figure 41A:
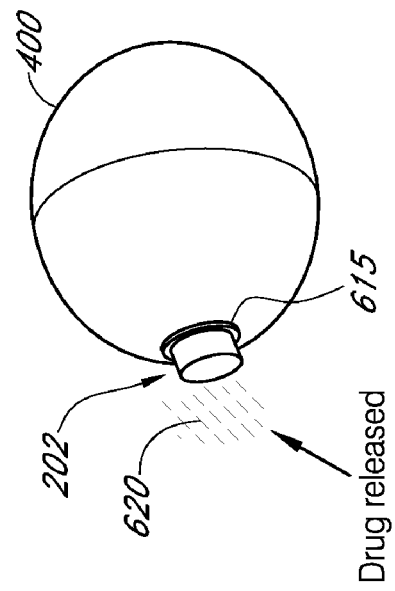
FIGS. 41A and B are perspective views of exemplary drug delivery subcomponents, in accordance with a preferred embodiment.
Figure 41B:
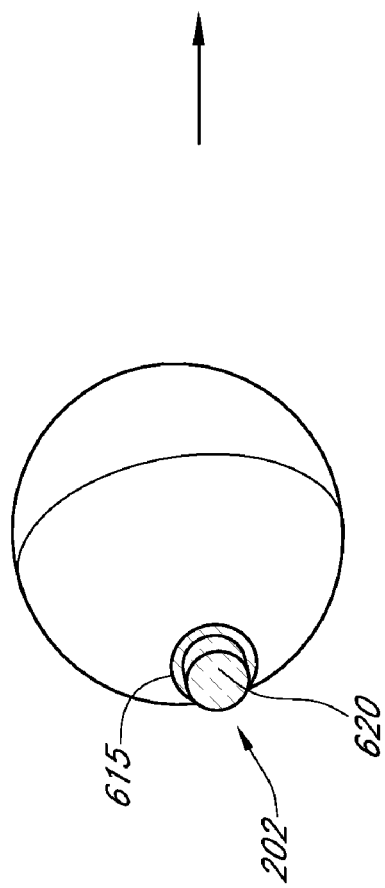

In certain embodiments, as seen in FIGS. 40A through 41B, the volume-occupying subcomponent 400 may contain pharmaceutical substances in an interior cavity. FIG. 40A shows the volume-occupying subcomponent 400 in a deployed or inflated state containing a drug 620 in an interior volume of the volume-occupying subcomponent 400. FIG. 40B shows the volume-occupying subcomponent 400 in a deflated state and the subsequent release of the drug 620 from the interior of the volume-occupying subcomponent 400. FIG. 41A shows a volume-occupying subcomponent 400 containing a drug 620 in a sub-compartment 615 of the volume-occupying subcomponent 400 that is adjacent to the head 202. FIG. 41B shows the subsequent release of drug 620 from the sub-compartment 615. Release of the drug 620 from sub-compartment 615 may be achieved by any number of means such as by a pump, valve or head breakage.

Alternatively, the inflation subcomponent may be configured to gradually release pharmaceutical substances as the head component(s) disintegrate or in bulk when the head component separates from the volume-occupying subcomponent. For example, a pharmaceutical may be fixed in biodegradable plug materials and released as such materials degrade in the stomach. Such substances may be incorporated or implanted into a polymer (e.g. by means of diffusion or hydrolysis) which can be sprayed, sputter coated, vapor deposited or applied in liquid form onto the outside of the volume-occupying subcomponent.

Furthermore, pharmaceutical substances may also be incorporated into one or more of the barrier coatings of the volume-occupying subcomponent or a lubricious coating applied to the volume-occupying subcomponent. Release of the drug may, for example, be modulated by diffusion of the drug from the coating or by degradation of the coating itself, resulting in the release of the drug. The release or diffusion properties of the drug may be influenced by modifying the characteristics of the polymer, such as by changing the ratio of hydrophobic to hydrophilic molecules in the composition of the polymer. Release of drug may also be modulated by electrophoresis actuated by remotely by an external source.

It may be advantageous to treat the volume-occupying subcomponent such that its outer layer has antimicrobial properties so that it may treat or prevent stomach infections. For example, certain portions of the outer layer of the volume-occupying subcomponent may contain silver. As a further example, the outer layer of the volume-occupying subcomponent may be made of a material (such as polyurethane) that allows for ion transfer across of it, with silver materials behind such layer such that the silver ions are able to diffuse out of the volume-occupying subcomponent or onto its exterior surface.

For example, the volume-occupying subcomponent may be coated with a drug, or combination of drugs, to control stomach acid and other gastrointestinal conditions such as ulcers and GERD. The drugs may, but need not be selected from the group of drugs including proton pump inhibitors such as Prilosec, Nexium, Prevacid, Protonix and Aciphex or $H_2$ receptor antagonists such as Tagamet, Pepcid, Axid, Zantac and Rotane.

The volume-occupying subcomponent may be treated with anti-emetics drug or combinations of anti-emetics to control nausea and vomiting including, but not limited to, 5HT3 antagonists such as compazine, dolasetron, granisetron, ondansetron, tropisetron, palonosetron or dopamine antagonists such as domperidone, droperidol, haloperidol, chlorpromazine, promethazine, prochlorperazine, metoclopramide, alizapride or antihistamines (H1 receptor antagonists) such as cyclizine, diphenhydramine, dimenhydrinate, meclizine, promethazine, hydroxyzine or cannabinoids.

The volume-occupying subcomponent may be coated with drugs or combinations of drugs to control body weight including serotonin re-uptake inhibitors (e.g., fluoxetine), noradrenergic re-uptake inhibitors (e.g., phentermine), a serotonin and noradrenergic re-uptake inhibitor (sibutramine) and an intestinal lipase inhibitor (orlistat), Leptin, amylin, melanocortin-4 receptor agonists, neuropeptide Y antagonists, beta(3) adrenergic agonists and glucagon-like peptide-1 agonists and CB1 endocannabinoid receptor antagonists and CNS modulators that mediate appetite and energy expenditure.

The volume-occupying subcomponent may also be coated with drugs or combinations of drugs to control blood glucose levels including but not limited to sulfonylureas, meglitinides, nateglinides, biguanides, thiazolidinediones, and alpha-glucose inhibitors.

Example drugs may also include satiety signaling substances or substances that modulate hormone levels.

Example drugs may also include laxative agents. Such laxative agents may be useful in facilitating the passage of the volume-occupying subcomponent from the body when it is in its deflated state.

Example drugs may also include substances that modulate gastric emptying such as cholestyramine, or that modulate gastric absorption.

Example drugs may also include analgesics such as acetaminophen, the non-steroidal anti-inflammatory drugs (NSAIDs) such as the salicylates and narcotic drugs such as morphine.

Example drugs may also include substances that reduce nicotine and/or tobacco craving such as varenicline, bupropion and nortriptyline.

Example drugs may also include birth control substances such as combinations of estrogen and progestin, and selective estrogen receptor modulators.

Example drugs may also include antibiotics or other anti-bacterial substances.

Example drugs may also include antacids.

A possible alternative to a coated volume-occupying subcomponent is a volume-occupying subcomponent containing reservoirs that contain the pharmaceutical of interest. For example, the present invention provides a volume-occupying device that could be used as a subcomponent for delivering drugs to the stomach, possibly including a framework with a plurality of reservoirs and a drug polymer or combination of drug polymers positioned in the reservoirs. In one embodiment, a plurality of microcapsules on the exterior of said volume-occupying subcomponent, each of said microcapsules carrying a drug or combination of drugs for treatment with the stomach when said volume-occupying subcomponent, is positioned and inflated such that the drug or drugs may be released from said microcapsules.

A possible alternative to a coated volume-occupying subcomponent is a volume-occupying subcomponent containing the pharmaceutical of interest in its plug materials. Any of the means to initiate deflation described above may be used to modulate erosion or breakage of the plug materials to initiate release of drug substance.

A possible alternative to a coated volume-occupying subcomponent is a volume-occupying subcomponent containing the pharmaceutical of interest in its creases when it is in is delivery form, with release of the drug initiated by expansion of the volume-occupying subcomponent.

A possible alternative to a coated volume-occupying subcomponent is a volume-occupying subcomponent containing the pharmaceutical of interest in its cavity. Release of the drug may be modulated by a pump that may be actuated as described above.

The drug delivery components of the volume-occupying subcomponent may be designed in such way as to incorporate multiple drugs and to release select drugs upon command. For example, drugs may be layered on top of one another or adjacent to each other on certain portions of the volume-occupying subcomponent.

The contents of the following publications, which recite methods of controlled drug delivery are hereby incorporated into this application by reference: Langer, R. (1998) "Drug Delivery and Targeting," Nature vol. 392/Supp, pp. 5-10; Controlled Drug Delivery Systems, Xue Shen Wu, PhD., Technomic Publishing Co, 1996.

Alternatively, the volume-occupying subcomponent may contain a subcomponent that may electro-modulate certain nerves in the stomach (such as the vagus nerve) to induce satiety. Such subcomponent may be recharged inductively by an exterior power source.

Swallowable, Self-Inflating Intragastric Balloon System

A swallowable, self-inflating intragastric balloon system according to selected preferred embodiments includes the following components: a balloon in a deflated and compacted state ("balloon"); an inner capsule or other container ("inner container") that contains one or more $CO_2$ generating components and that is present inside the lumen of the balloon; and an outer capsule, container, or coating ("outer container") that contains the balloon. The balloon further comprises a self-sealing valve system, preferably attached to the inner surface of the balloon by an adhesive or other means (e.g., welding), and an inoculation spacer to prevent puncture of the wall of the balloon and inner container by a needle or other means for injecting an liquid activation agent into the lumen of the balloon via the self-sealing valve. The outer container preferably incorporates the balloon in a compacted state (e.g., folded and rolled) with sufficient space to allow for activation liquid to be injected into the balloon. The liquid activation agent initiates separation, erosion, degradation, and/or dissolution of the inner container and generation of $CO_2$ upon contact with the inflation agent contained within the inner container, which subsequently causes outer container separation, erosion, degradation, and/or dissolution due to $CO_2$ gas pressure.

Figure 44A:
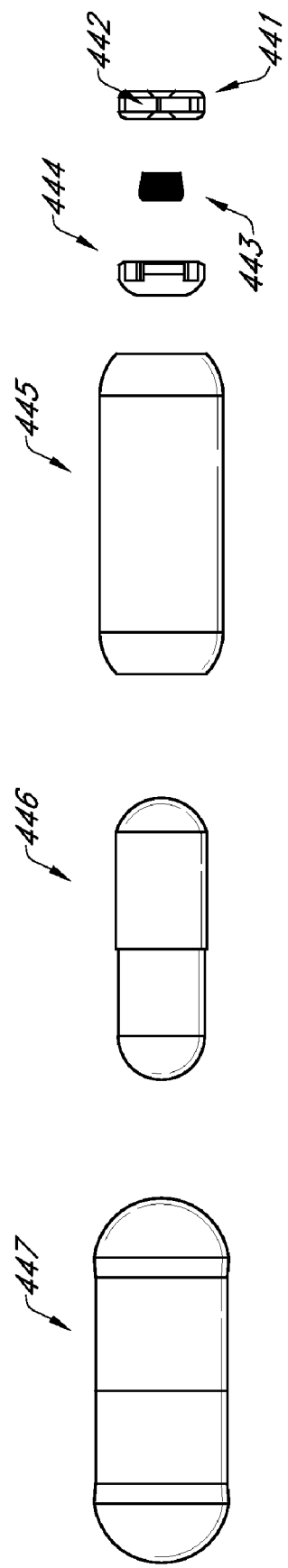
FIGS. 44A and B depicts components of a swallowable, self-inflating intragastric balloon system.
Figure 44B:
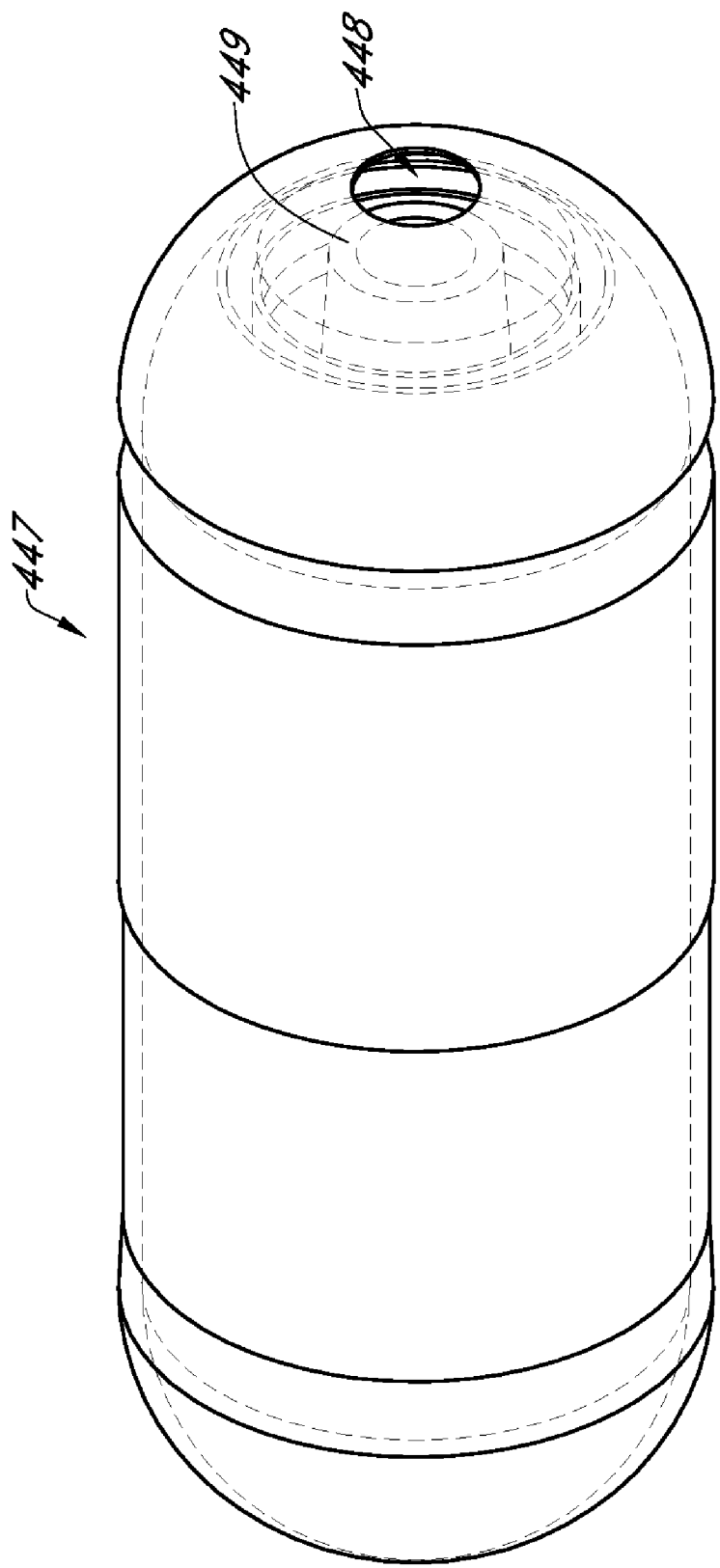
FIG. 44B depicts a fully assembled outer container 447 including vent hole 448 aligned with septum 449 for puncture to inject liquid activation agent.

FIG. 44A depicts selected components of a swallowable, self-inflating intragastric balloon system of a preferred embodiment, including a silicone head 441 with radioopacity ring 442, trimmed 30 D silicone septum 443, Nylon 6 inoculation spacer 444, compacted balloon 445, inner container 446, and outer container 447 as constituents of the system in unassembled form. FIG. 44B depicts a fully assembled outer container 447 including vent hole 448 aligned with septum 449 for puncture to inject liquid activation agent. As discussed further below, the components of particularly preferred systems possess the attributes described herein; however, in certain embodiments systems can be employed which utilize components having other attributes and/or values.

Balloon

The balloon is fully sealed 360 degrees around with no external opening or orifice to the central lumen. The balloon has an "inverted" configuration. The term "inverted" as used herein is a broad term, and is to be given its ordinary and customary meaning to a person of ordinary skill in the art (and is not to be limited to a special or customized meaning), and refers without limitation to a balloon having a smooth external surface with seams, welds, or the inside the balloon. In order to create a balloon with an inverted configuration, e.g., a balloon with no external seam allowance (no wall material between the edge of the balloon and the weld, seam, or other feature joining the sides together), two balloon halves are joined together in some fashion (e.g., adhered using adhesive or heat or the like based on the balloon material used). One of the balloon halves encompasses an opening to allow for the balloon to be pulled through itself after adherence of the two halves and to have the seams of the balloon on the inside. The opening created is preferably circular but can be any similar shape, and the diameter of the opening preferably does not exceed 3.8 cm; however, in certain embodiments a larger diameter may be acceptable. A patch of material is adhered (adhesively, heat welded, or the like, based on the material used) to cover the original balloon-half opening. The inversion hole thus created that is subsequently patched is small enough that the forces exerted during inflation do not compromise the material used to maintain $CO_2$ gas in the balloon. The preferred shape for the inflated balloon in final assembly is ellipsoid, preferably spheroid or oblate spheroid, with nominal radii of from 1 inch (2.5 cm) to 3 inches (7.6 cm), a nominal height of from 0.25 inches (0.6 cm) to 3 inches (7.6 cm), a volume of from 90 $cm^3$ to 350 $cm^3$ (at 37° C. and at internal nominal pressure and/or full inflation), an internal nominal pressure (at 37° C.) of 0 psi (0 Pa) to 15 psi (103421 Pa), and a weight of less than 15 g. The balloon is configured for self-inflation with $CO_2$ and is configured to retain more than 75% of the original nominal volume for at least 25 days, preferably for at least 90 days when residing in the stomach.

Figure 45A:
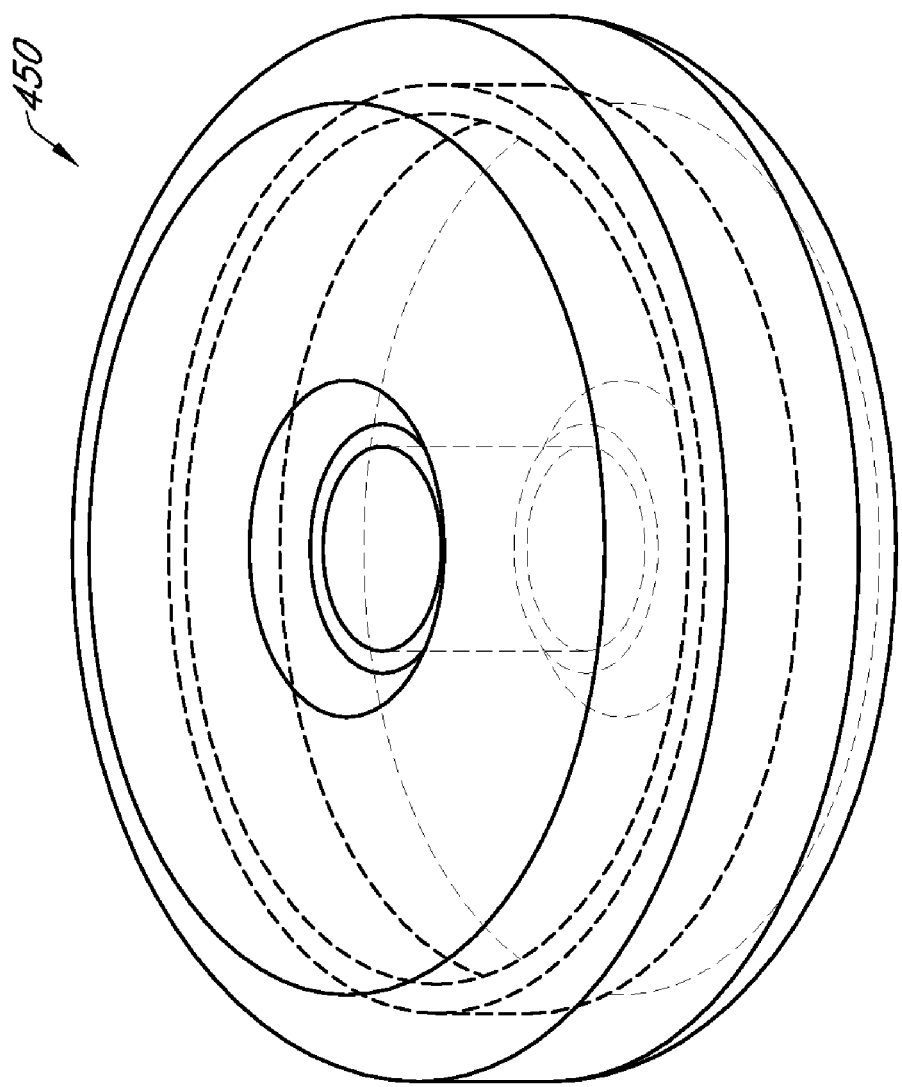
FIGS. 45A-B depict a silicone head 451 and opacity ring 452 of a self-sealing valve system 450 of a preferred embodiment.
Figure 45B:
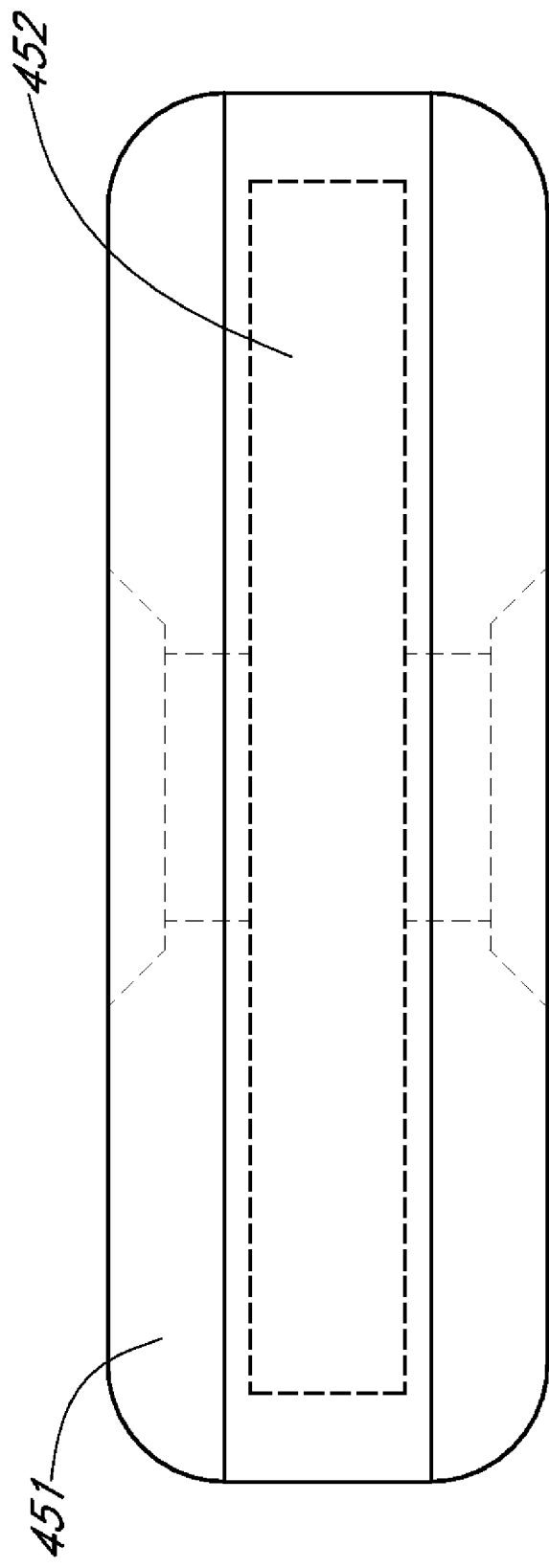
Figure 46A:
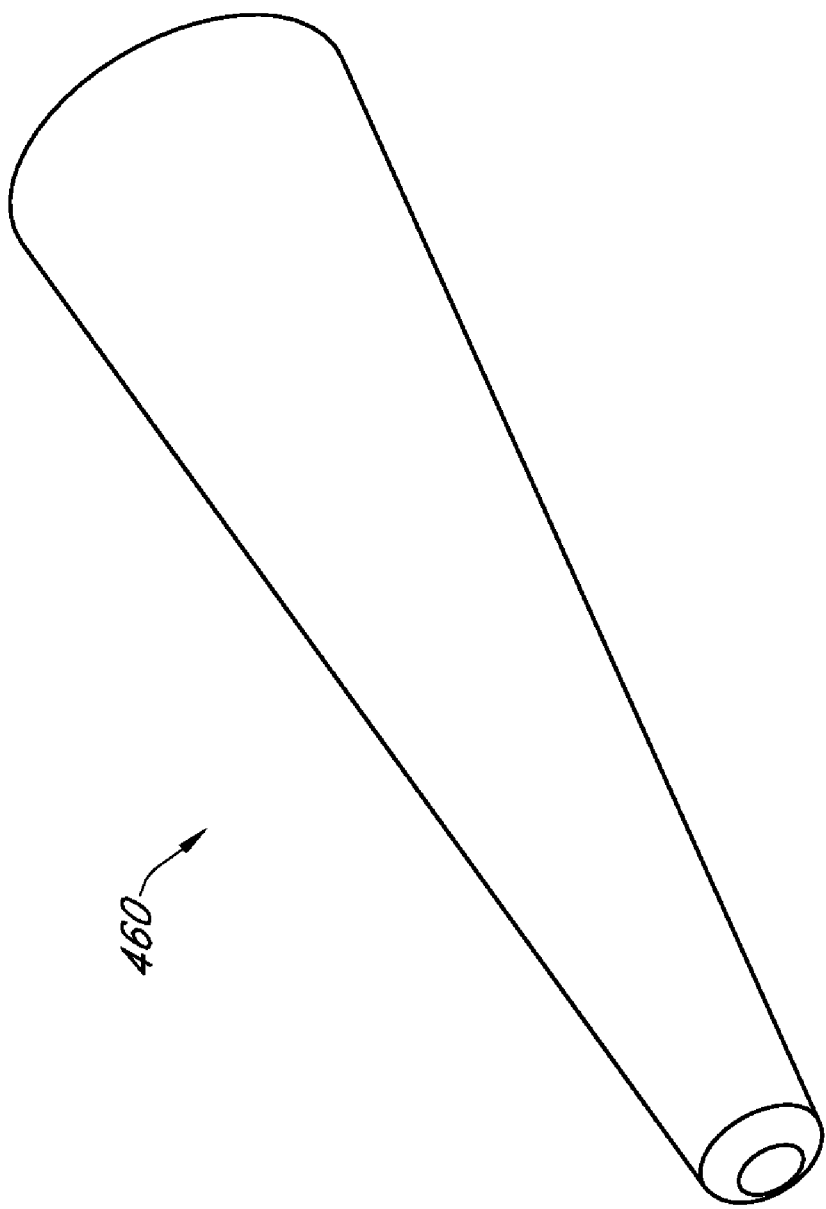
FIGS. 46A-C depict a wedge-shaped septum 460 of a preferred embodiment.
Figure 46B:
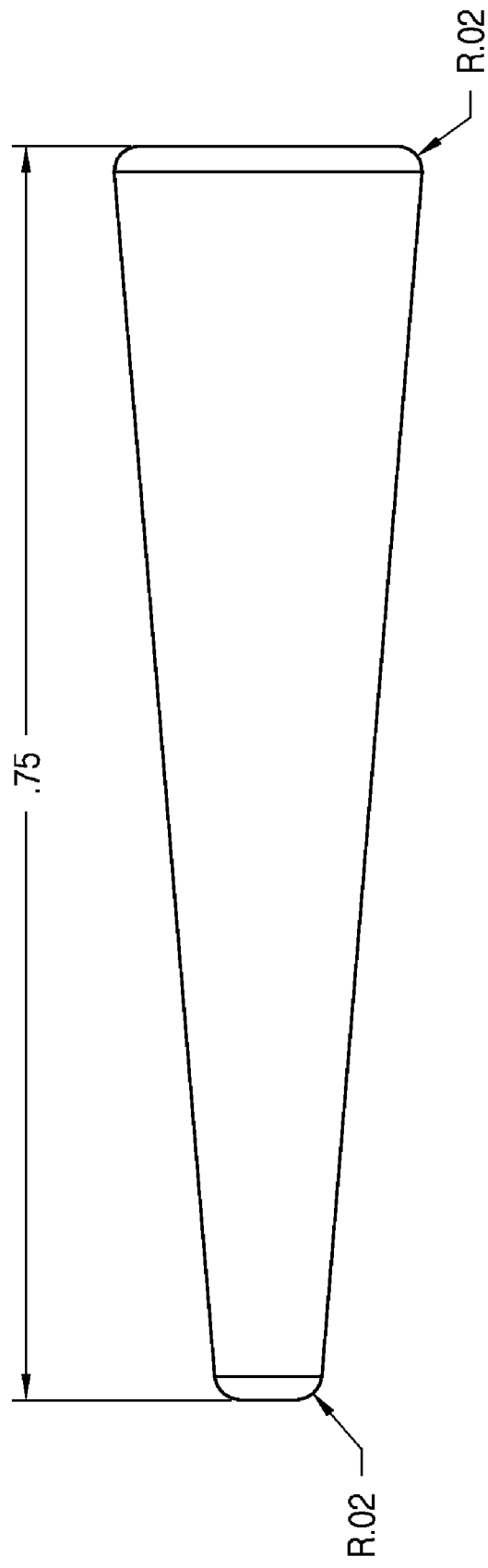
Figure 46C:
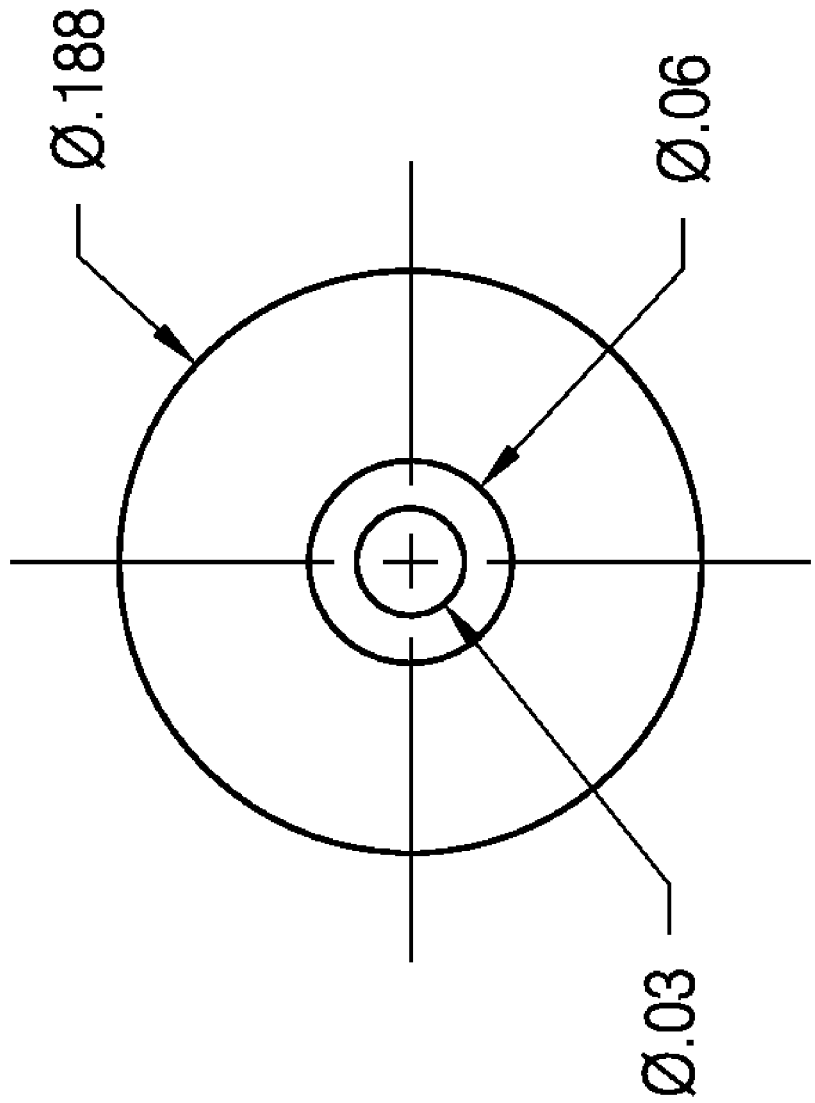
Figure 47A:
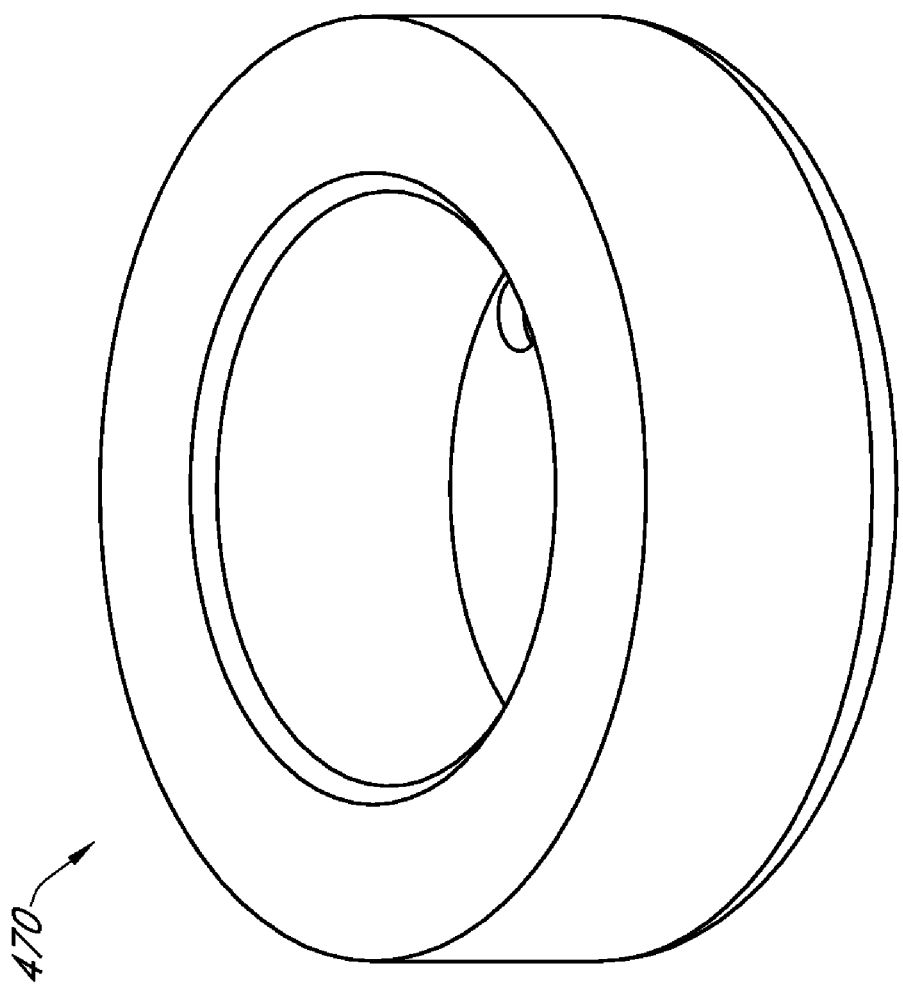
FIGS. 47A-E depict a cupped needle stop (inoculation spacer) 470 of a preferred embodiment.
Figure 47B:
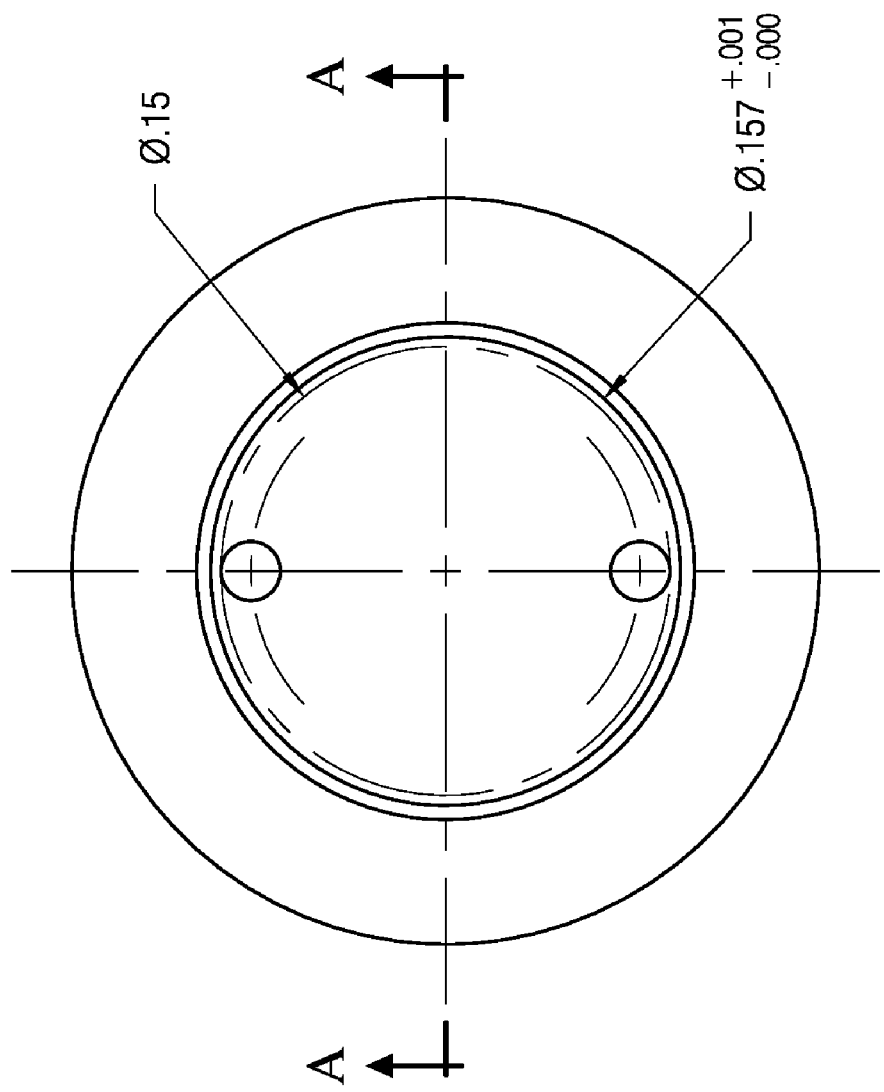
Figure 47C:
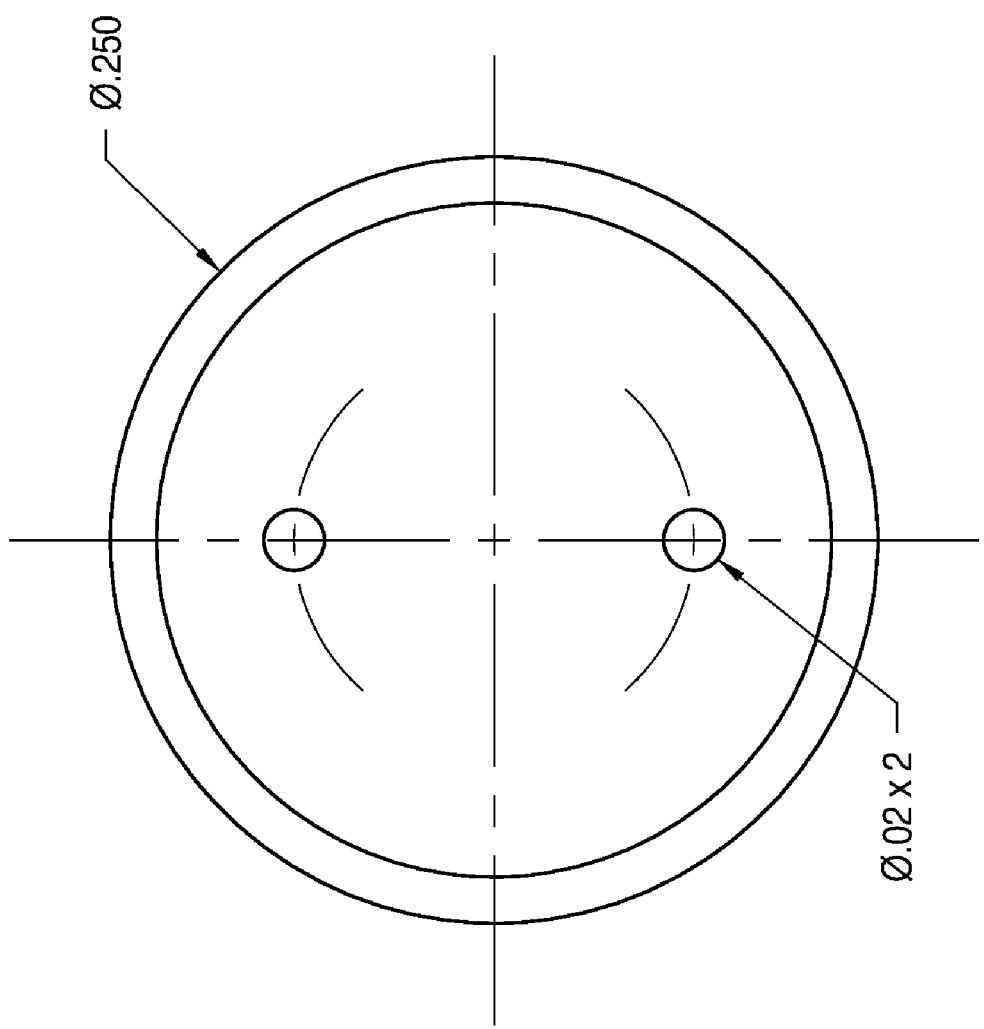
Figure 47D:
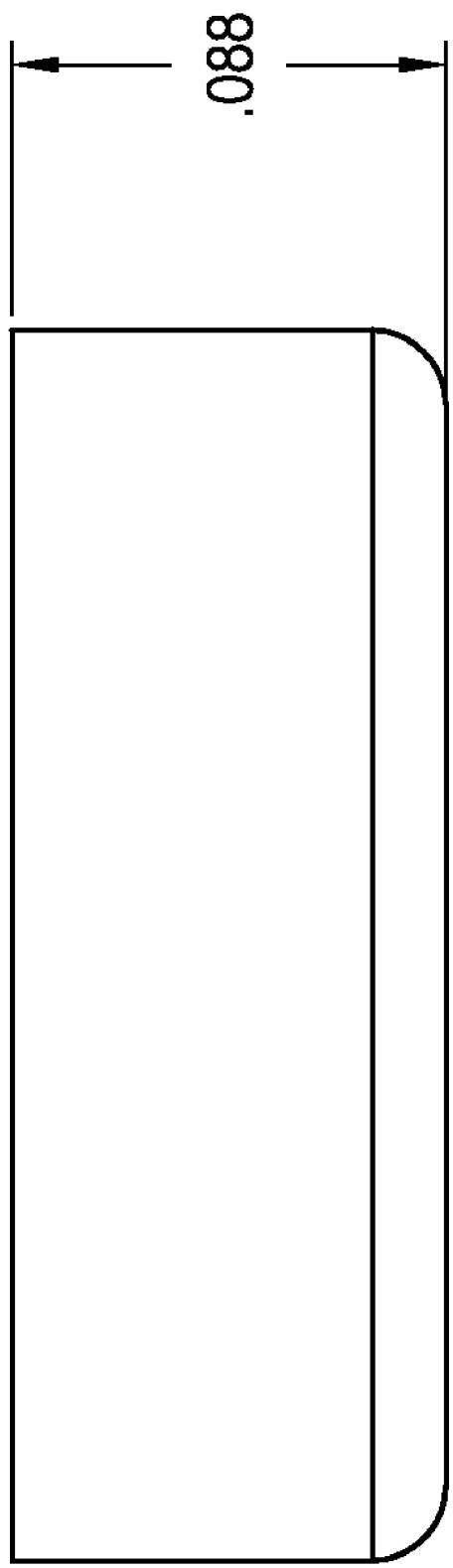
Figure 47E:
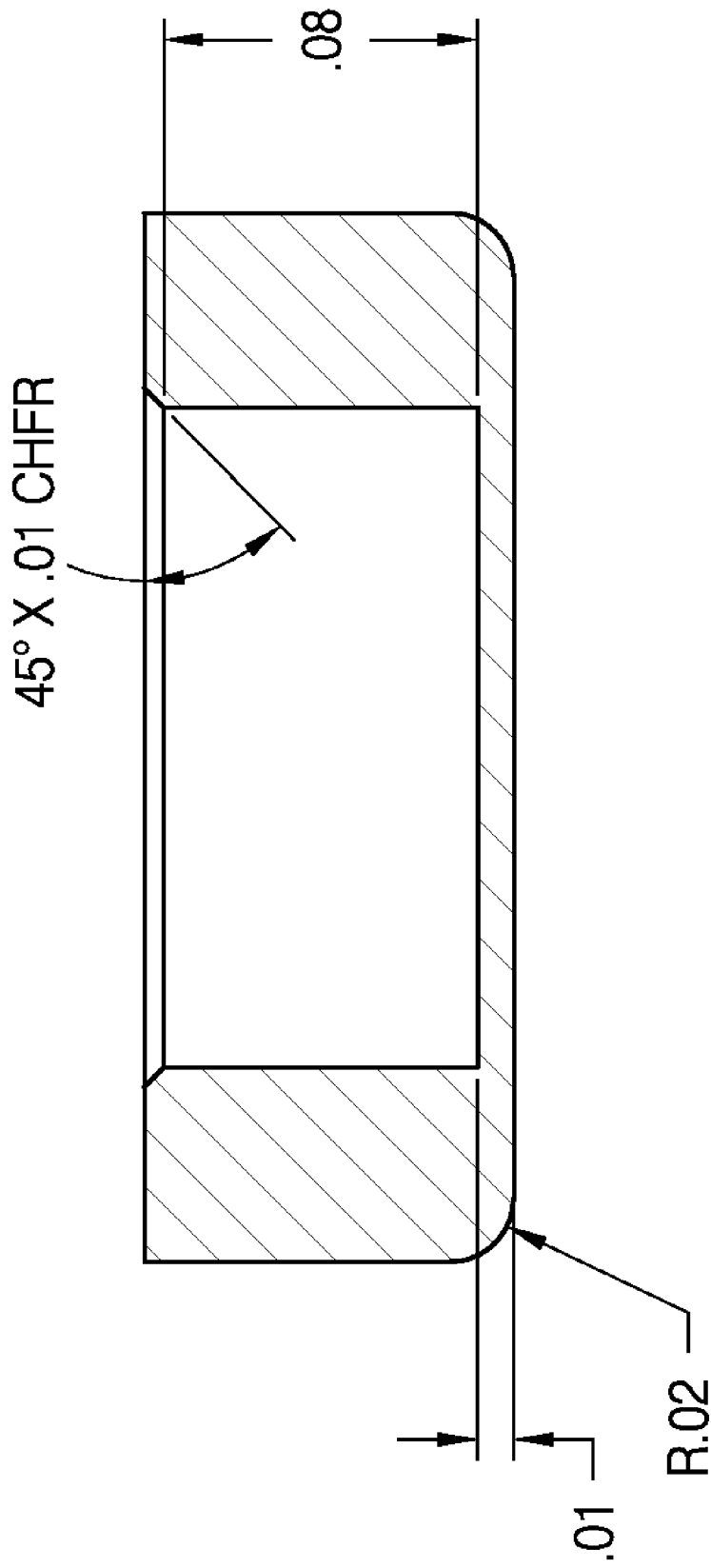

A self-sealing valve system is attached to the balloon (e.g., on its inside surface) without the use of an opening, orifice, or other conduit in the wall of the balloon. The valve system utilizes a septum with a durometer of 20 Shore A to 60 Shore D. The valve is inserted or otherwise fabricated into a retaining structure that has a higher durometer, e.g., 40 Shore D to 70 Shore D or more. The retaining structure is fabricated from a silicone, rubber, soft plastic or any suitable non-metallic polymeric material such as an acrylic, an epoxy, a thermoplastic elastomer, or thermoplastic polyurethane. Preferably, a structure, such as a ring, that is metallic or non-metallic but radioopaque (e.g., barium) and visible under X-ray, is embedded in the retaining structure. Using a mechanical fit mechanism of two structures of different durometers, one softer (septum) with a large diameter, is inserted into a snug, more rigid durometer structure creates compressive forces in the once open orifice to enable $CO_2$ retention and reduce susceptibility for $CO_2$ gas leaks. The metallic ring for radio-opacity also helps to create compressive forces on the septum. The self-sealing septum allows air to be evacuated from the balloon for processing/compacting and inserting in the outer container, and also allows for the inflation agent to be injected into the outer container for inflation initiation. Additional septums can be provided, if desired; however, it is generally preferred to employ a single septum so as to maintain the volume of the deflated/folded balloon (and thus the outer capsule) as small as possible. The valve system is preferably attached to the inner surface of the balloon such that a shear force greater than 9 lbs (40 N) is required to dislodge the valve system. FIGS. 45A-B depict various views of a silicone head 451 and opacity ring 452 of a self-sealing valve system 450 of a preferred embodiment; FIGS. 46A-C depict various views of a wedge-shaped septum 460 of a preferred embodiment.

Inner Container

The inner container is contained within the lumen of the balloon and contains the $CO_2$ generator for balloon self-inflation. The $CO_2$ generator comprises an inflation agent mixture housed within the container. Preferably, from about 10% to about 80% of the total inflation agent used comprises powdered citric acid, with the remainder comprising powdered sodium bicarbonate. Sufficient inflation agent is provided such that upon completion of the $CO_2$ generating reaction, the balloon achieves inflation at the nominal inflation pressure described above. Preferably, a total of from about 0.28 to 4 grams inflation agent mixture is employed, depending upon the balloon size to be inflated; preferably up to 1.15 grams of sodium bicarbonate is used with the remainder being powdered citric acid to generate 300 $cm^3$ of $CO_2$ at nominal pressure.

The inflation agent is compressed, formed or otherwise held in a shape which provides good surface area availability for the reactants for $CO_2$ generation, while minimizing the space and/or volume sufficient to hold the inner container. Preferably, the inner container has a length (longest dimension) of from about 0.748 inches (1.9 cm) to 1.06 inches (2.7 cm) and a diameter or width of from about 0.239 inches (0.6 cm) to about 0.376 inches (1 cm). The volume of the inner container is preferably from about 0.41 ml to about 1.37 ml. The inner container is preferably in the form of a standard gelatin capsule but a gelatin tape may be used in lieu of a push fit capsule. The container is preferably relied upon for containing the inflation agent; however, additional sealing or other encapsulation can be employed to control timing of inflation. Gelatin is particularly preferred for use as the inner container; however other materials can also be suitable for use, e.g., cellulose. In order to minimize the internal volume of the system, it is generally preferred to include only a single inner container; however, in certain embodiments two or more internal containers can advantageously be employed. Timing of self-inflation is selected based on a normal esophageal transit time and a normal time of gastric emptying of large food particles, such that the balloon does not inflate to a size that would block the esophageal passageway or prematurely pass through the pyloric sphincter. Timing is also derived by compacting the balloon such that the activation agent is substantially localized in the balloon next to the inner capsule, creating an efficient $CO_2$ self-inflation method. I was able to get through the body this evening and attached are a few edits (very minor). Balloon inflation is initiated by the liquid activation agent causing degradation of the inner container, such that the inflation agent in the inner container contacts the liquid activation agent, thereby initiating the gas generation reaction.

An inoculation spacer is preferably incorporated to guide a needle into the self-sealing valve for injection of liquid activation agent into the lumen of the balloon and to prevent the needle from penetrating the wall of the deflated/folded balloon elsewhere such that pressure within the lumen of the balloon cannot be maintained. The inoculation spacer also facilitates preventing liquid activation agent from penetrating the inner container or the folded balloon material, thereby focusing the activation agent in an appropriate manner to properly mix the reactants for $CO_2$ generation according to the criteria described above. The inoculation spacer is generally in the form of a tube or cylinder. The inoculation spacer is preferably attached to the inner container and/or the self-sealing valve system with an adhesive or other fixing means; however, in certain embodiments the inoculation spacer can be "free-floating" and maintained in position by the folding or rolling of the walls of the balloon. The inoculation spacer can comprise any suitable material that can be passed after separation, erosion, degradation, digestion, and/or dissolution of the outer container; however, preferable materials include non-metallic materials with a minimum Shore D durometer of 40 or more, any metallic material, or a combination thereof. FIGS. 47A-E depict various views of a cupped needle stop (inoculation spacer) 470 of a preferred embodiment.

Outer Container

The balloon is preferably provided in a deflated and folded state in a capsule or other retaining, containing or coating structure ("outer container"). The outer container is preferably in the form of a standard push-fit gelatin capsule, with the push-fit relied upon for containing the deflated/folded balloon; however, a gelatin wrap can advantageously be employed in certain embodiments. Gelatin is particularly preferred for use as the outer container; however other materials can also be suitable for use, e.g., cellulose, collagen, and the like. Preferably, the outer container has a length (longest dimension) of from about 0.95 inches (2.4 cm) to 2.5 inches (6.3 cm) and a diameter or width of from about 0.35 inches (0.9 cm) to about 0.9 inches (2.4 cm). The volume of the inner container is preferably from about 1.2 ml to about 8.25 ml. The outer container is preferably configured with one or more holes, slits, passageways or other egresses, preferably on each end, which act as vents such that any gas created due to inflation agent exposure to condensation or other ambient moisture present during processing does not cause premature separation or degradation of the inner container prior to 30 seconds after inoculation of the liquid activation agent, which may have an undesirable effect on reaction efficiency. The outer capsule degrades (e.g., separates, dissolves, or otherwise opens) due to pressure build up caused by inflation of the balloon.

Inflation

The swallowable, self-inflating intragastric balloon is provided with mechanisms to reliably control timing of self-inflation such that premature inflation while in the esophagus during swallowing is avoided and sufficient inflation once in the stomach so as to prevent passage through the pyloric sphincter is ensured. Normal esophageal transit time for large food particles has been documented as 4-8 seconds, and gastric emptying of large food particles through the pylorus does not occur for at least 15-20 minutes. The outer container is preferably configured to separate, dissolve, degrade, erode, and/or otherwise allow the deflated/folded balloon to begin unfolding not less than 60 seconds but not more than 15 minutes after inoculation with liquid activation agent. The inner container is preferably configured chemically, mechanically or a combination thereof to retard the initial $CO_2$ generating chemical reaction such that sufficient $CO_2$ to begin inflating the balloon is not available earlier than 30 seconds after inoculation with the liquid activation agent, but to permit generation of sufficient $CO_2$ such that at least 10% of the occupyable volume of the balloon is filled within 30 minutes, at least 60% of the occupyable volume of the balloon is filled within 12 hours, and at least 90% of the occupyable volume of the balloon is filled within 24 hours. This timing allows for injection of the activation agent into the outer container by the medical professional, passing the device to the patient, and swallowing by normal peristaltic means by the patient. This timing also prohibits potential passing of an uninflated balloon into the duodenum by the balloon being inflated to a sufficient size such that gastric emptying of the balloon would not be easy, as objects more than 7 mm in diameter do not readily pass.

The activation agent is preferably injected using a syringe having a needle with a gauge diameter of from 25 to 32. The needle length is preferably from about 0.25 inches (0.6 cm) to 1 inches (2.54 cm) in length so as to create a flow rate that allows for delivery of the full volume of inflation agent within 30 seconds, but in a manner/stream/flow that does not physically damage the inner container, thereby causing premature $CO_2$ generation and inflation. The activation agent is preferably pure water, or a solution containing up to 50% concentration of anhydrous citric acid at 20° C., or the equivalent thereof at varying solution temperatures based on solubility of anhydrous citric acid. Preferably, the system is configured to have an occupyable void space in the central lumen of the balloon when in compacted form in the outer container of from about 0.3 ml to about 4.5 ml, such that a corresponding volume of activation agent can be injected into the void space.

Prior to placement in the outer container of the balloon containing the inner container, the balloon is deflated and folded. In a deflated state, the balloon is flat, with the inverted seam extending around the perimeter of the balloon. The self-sealing valve system is affixed to the inner wall of the lumen close to the center of the deflated balloon, with the inner container positioned adjacent to the self-sealing valve system. The walls of the balloon are then folded. As part of the balloon design, the self-sealing valve system is manufactured in a manner such that it is placed "off center" to minimize the number of folds upon themselves (e.g., doubling or tripling up) required to fit the balloon in the outer container. For example, the self-sealing valve system can advantageously be placed ½ r±¼ r from the center of the balloon, wherein r is the radius of the balloon along a line extending from the center of the balloon through the septum.

Figure 48A:
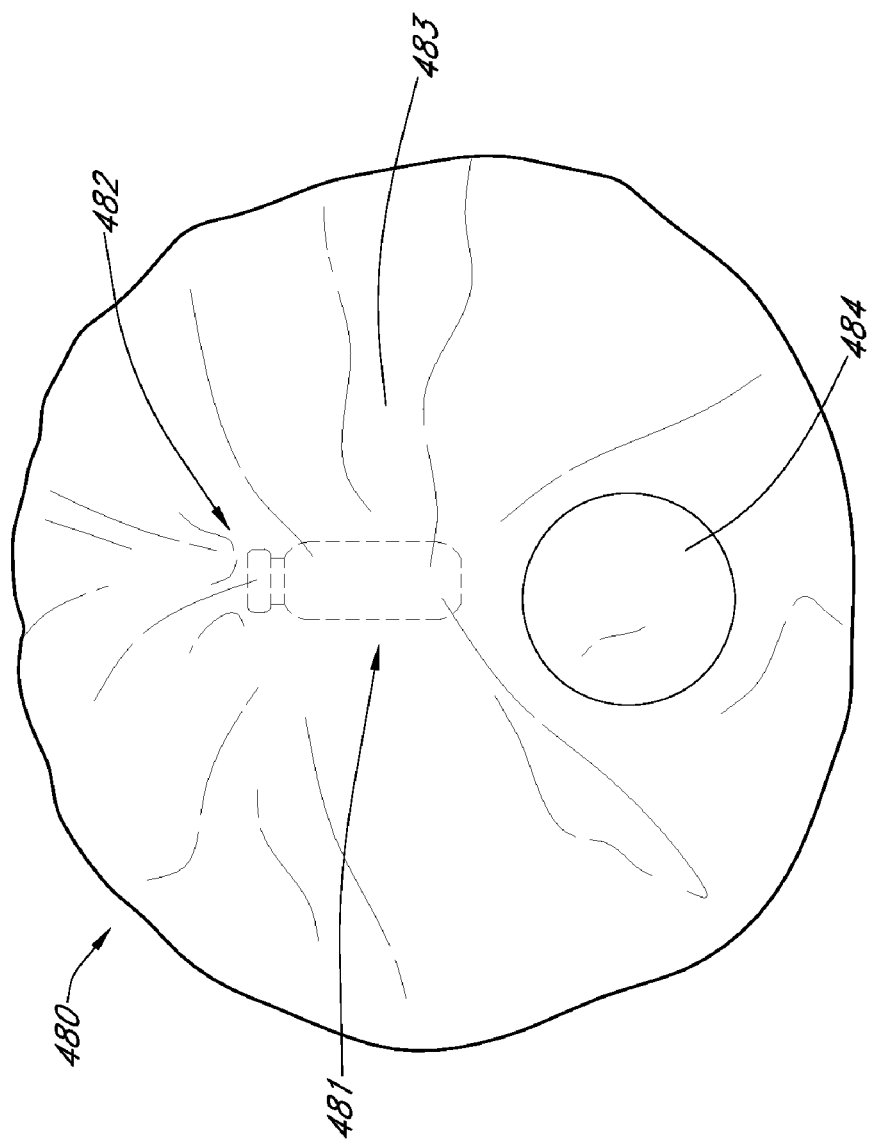
FIGS. 48A-G depict a process for folding a balloon of a preferred embodiment for placement in an outer container. The balloon 480 contains an inner container 481. A self-sealing valve system 482 is adhesively adhered to the interior of the wall 483 of the balloon, and the inverted configuration of the balloon is provided by inversion through a hole sealed with a patch 484.
Figure 48B:
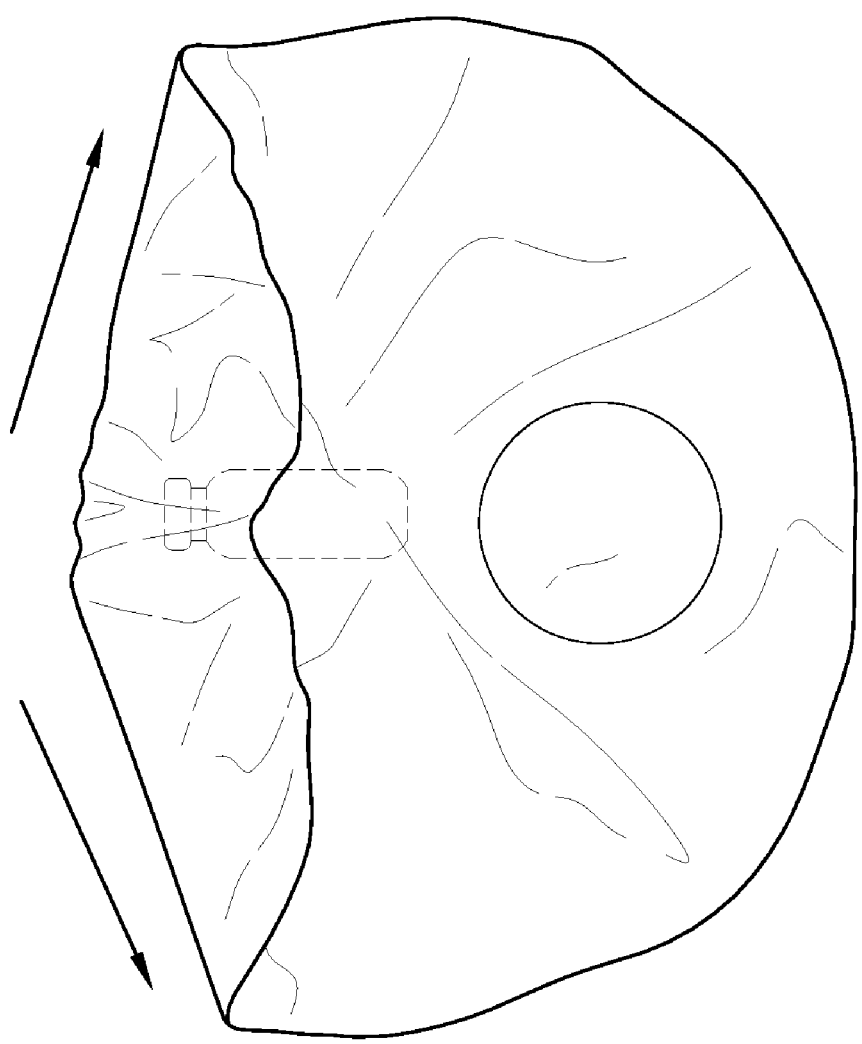
Figure 48C:
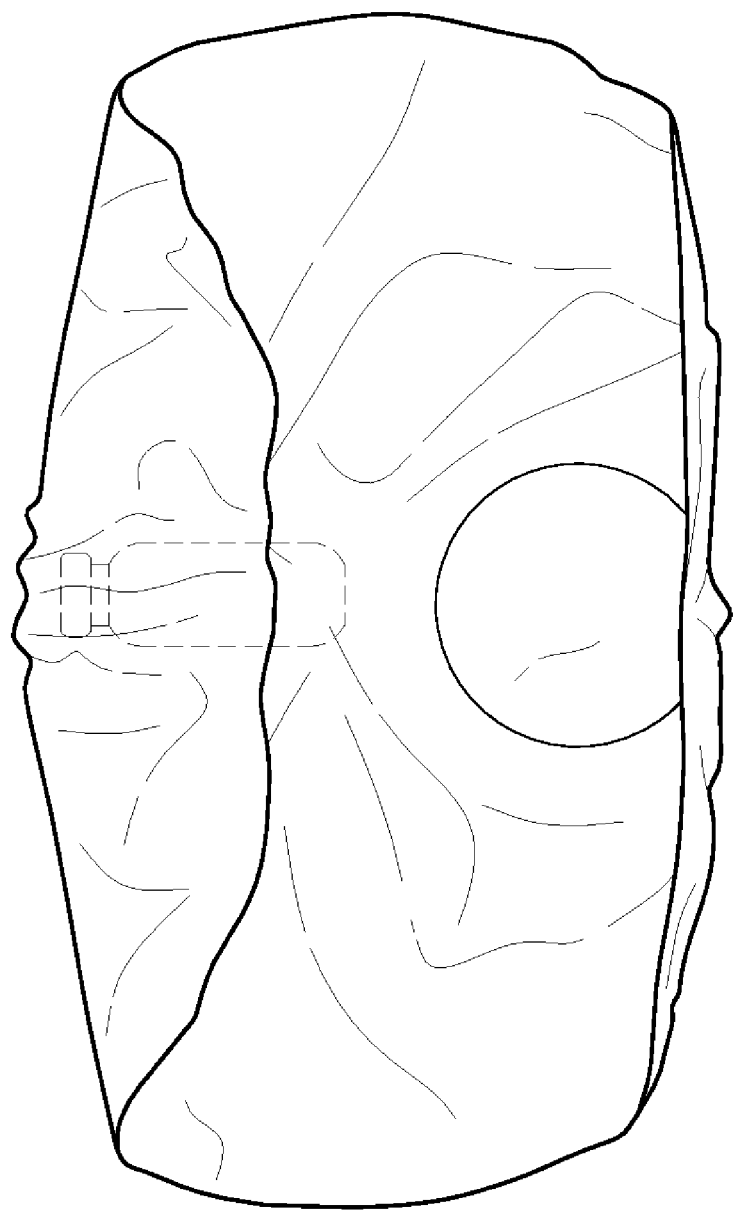
Figure 48D:
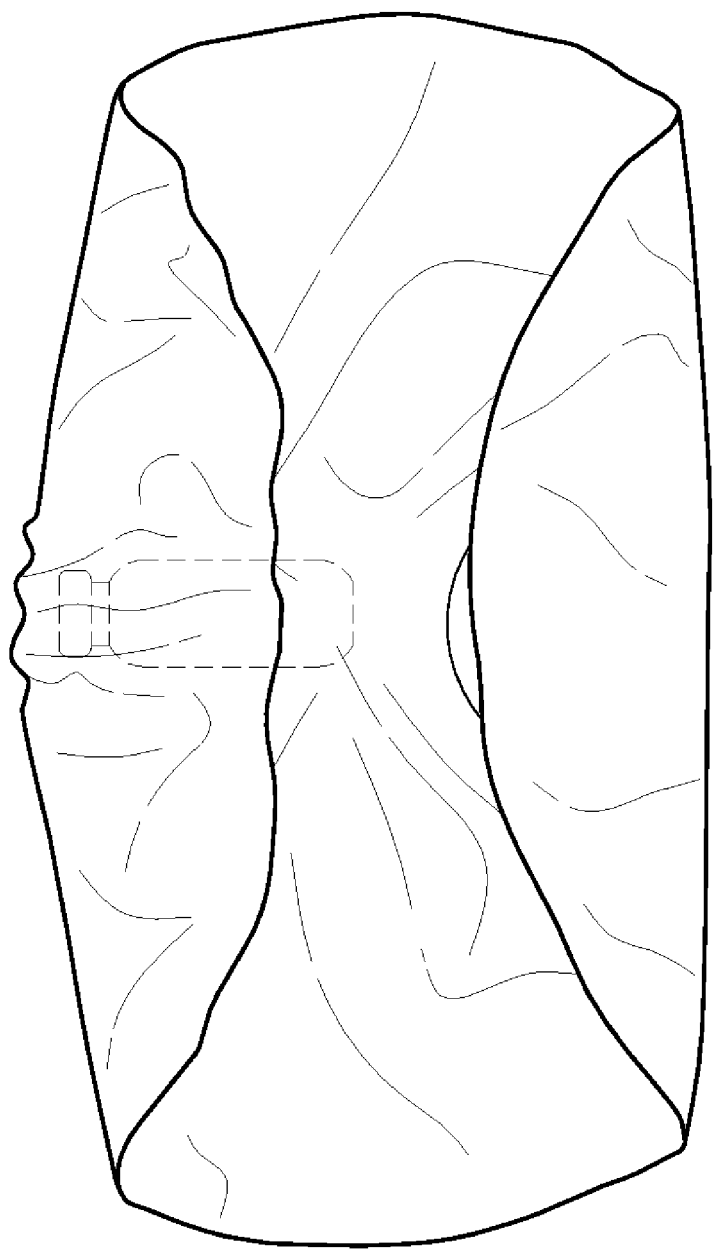
Figure 48E:
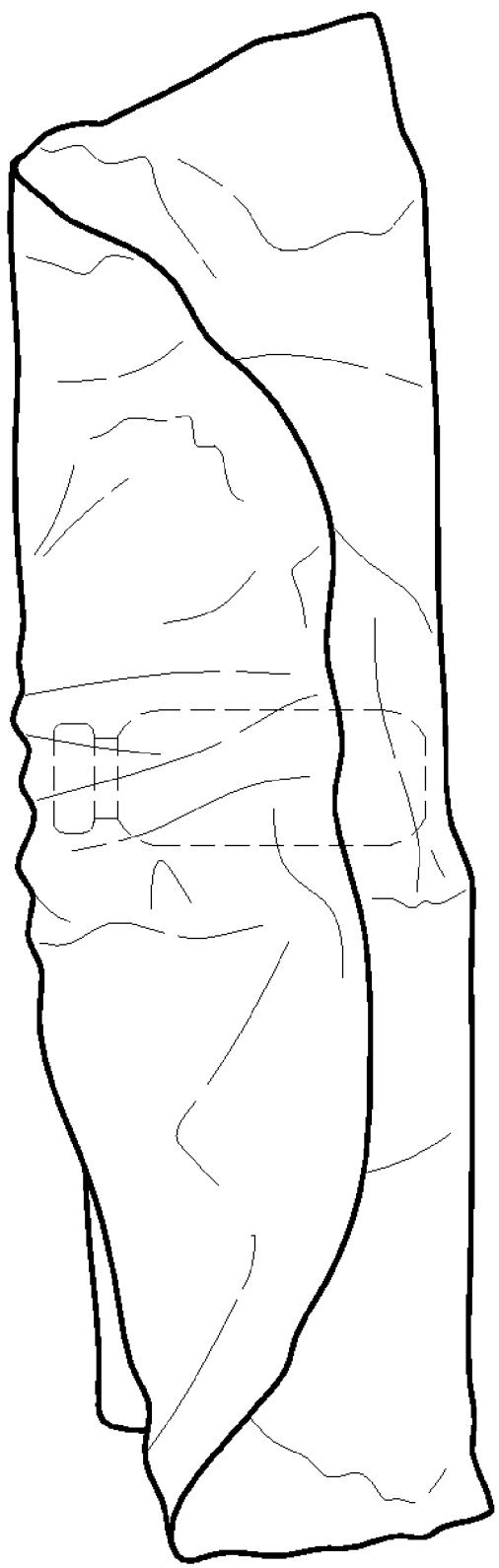
Figure 48F:
Figure 48G:
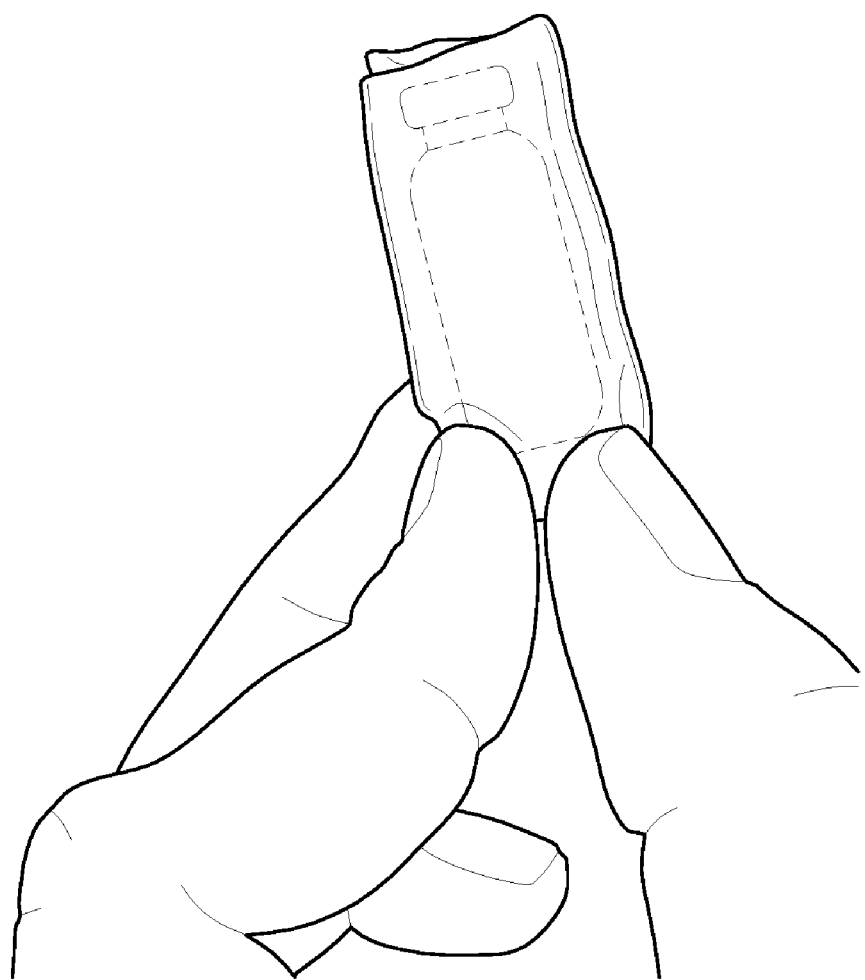

Prior to folding, the free-floating inner container with inflation agent for $CO_2$ generation is preferably vertically aligned with the self-sealing valve system such that the septum/inoculation spacer is placed directly above the tip of the capsule (FIG. 48A). The balloon 480 contains an inner container 481. A self-sealing valve system 482 is adhesively adhered to the interior of the wall 483 of the balloon, and the inverted configuration of the balloon is provided by inversion through a hole sealed with a patch 484. The top approximate ¼ of the balloon wall is folded over the inner capsule, and the pleats where the capsule is are creased similar to the pleats formed in the second step of making a paper airplane, then folded over to the left or to the right (FIG. 48B). The bottom approximate ¾ of the sphere is then accordioned using no more than 2 creases and folded over the capsule (FIG. 48C-E). The left half is then folded over the right half of the capsule or vice versa so that the wings touch (FIG. 48F). Then the material is rolled over until it creates a tight roll (FIG. 48G). The device is then placed in the outer container.

The balloon is folded so as to form a pocket around the inner capsule is formed to insure that the liquid injected through the self-sealing valve system is contained in an area less than 10% of the entire balloon surface area. The balloon is folded such that the number of total folds is minimized so as to minimize possible damage to the outer material or compromise of $CO_2$ barrier properties. The number of total folds is preferably less than 10 folds. The balloon material is rolled when at all possible such that the number of creases required to fit the balloon in an outer container is minimized. This is done in effort to also to prevent lumen material damage. The self-sealing valve is also preferably constructed off-center of the balloon so as to minimize the number of folds that layer on top of each other.

The material forming the wall of the balloon is processed and folded to maximize reaction efficiency by localizing the initiation agent injected into the balloon so that it is maintained proximal to the reactants within the inner container. The balloon is folded such that once the reaction initiates and the outer container separates, the balloon unfolds in a manner that creates the largest possible surface area, which prohibits the balloon from readily passing through the pyloric sphincter. The ratio of reactants in the inflation agent and activation agent are selected such that the pH of any remnant liquid inside the lumen of the balloon is acidic, with a pH of less than 6, such that any balloon leakage or breach that allows stomach acid to enter does not cause additional $CO_2$ generation and resulting unintentional reinflation.

Deflation

The swallowable, self-inflating intragastric balloon is provided with mechanisms to reliably control timing of deflation. In preferred embodiments, the balloon auto-deflates and passes through the stomach, through the lower gastrointestinal tract, and out of the body. In the preferred embodiments described below, the timing of deflation can be accomplished via the external gastric environment (by conditions of temperature, humidity, solubility, and/or pH, for example) or via the environment within the lumen of the inflated balloon.

In other embodiments, the patch applied to allow for inverted seams as described above and/or one or more additional patches or other structures added to the balloon construction are made out of an erodible, degradable, or dissolvable material (natural or synthetic) and are incorporated into the wall of the balloon. The patch(es) are of sufficient size to ensure opening of a sufficient surface area to cause rapid deflation, and to prevent reinflation by seepage of stomach fluid into the balloon. The balloon patch(es) comprise materials that can be applied to the balloon such that a substantially smooth surface is maintained, and preferably comprise a single layer or multi-layered material. The patch(es) are constructed using an erodible, disintegrable, degradable or other such material that is preferably tissue-compatible and degrades into non-toxic products or is a material that slowly hydrolyzes and/or dissolves over time (e.g., poly(lactic-co-glycolic acid) (PLGA), polyvinyl alcohol (PVOH), polylactic acid (PLA), poly-L-lactic acid PLAA, Pullulan, Polyethylene Glycol (PEG), polyanhydrides, polyorthoesters, polyaryletherketones (PEEK), multi-block polyetheresters, poliglecaprone, polydioxanone, polytrimethylene carbonate, and other similar materials). These erodible, disintegrable, or degradable materials can be used alone, or in combination with other materials, or can be cast into/co-extruded, laminated, and/or dip coated in conjunction with non-erodible polymers (e.g., PET or the like) and employed in the construction of the balloon. Degradation/erosion occurs, is initiated by, and/or is controlled by the gastric environment (e.g., by conditions of temperature, humidity, solubility, and/or pH, for example), or is controlled within the lumen of the balloon (e.g., by conditions of humidity and/or derived pH, for example) based on what the patch is exposed to. Thickness of the polymer as well as environment which affects degradation and time of exposure can also facilitate degradation timing. Degradation/erosion are timed such that they occur once the pre-determined balloon useful life is completed (e.g., inflation is maintained for from 25 to 90 days in vivo in the stomach before degradation/erosion results in formation of an opening permitting deflation). As an alternative to (or in connection with) using an degradable material for the patch, the patch can comprise a similar $CO_2$ barrier film or the same film as the remaining wall of the balloon which is adhered to the balloon using a weak adhesive, or welded or adhered such that after a specified amount of time the patch delaminates from the applied area and allows for an opening for $CO_2$ release for deflation. The mechanism of using an erodible material, or a material that mechanically fails after a pre-specified time is be similar for all embodiments for deflation mechanisms described below as well. The timing of degradation or erosion can be controlled using the external gastric environment (e.g., by conditions of temperature, humidity, solubility, and/or pH, for example) and/or can be controlled by conditions within the lumen of the balloon (e.g., by conditions of humidity and/or pH of residual liquid in the balloon).

In other embodiments, a plug or plugs (optionally in conjunction another degradable retaining structure) can be incorporated into the balloon construction and can consist, all or in part, of an erodible, disintegrable, or otherwise degradable synthetic or natural polymer similar to those described above (e.g., PLGA, PLAA, PEG, or the like). The plug can be formed into various shapes (e.g., cylinder shape) to achieve various surface-to-volume ratios so as to provide a preselected and predictable bulk degradation pattern for the erodible polymer. The plug can incorporate a releasing mechanism that can be chemically initiated after degradation/erosion begins, such that the septum or plug material pops out of the balloon or falls inside of the balloon, thereby creating a passageway for $CO_2$ gas release and subsequent deflation of the balloon. Mechanical additions that can be used in conjunction with a plug include a compressed spring housed within the retaining structure or plug structure, or a degradable/erodible/disintegrable material that holds a plug (e.g., of a nondegradable or degradable material) in place. Once the material degrades, the spring is released and/or the plug/septum is pulled into the balloon or pushed out of the balloon, thus releasing $CO_2$ gas once an orifice has been created by release of the spring mechanism and pushing out or pulling in of the plug.

In certain embodiments, the balloon can incorporate one or more plugs in the wall of the balloon that contain a compressed pellet or gas releasing pellet. The pellet can be comprised of any combination of constituents that, when activated, emit $CO_2$ gas (e.g., sodium bicarbonate and citric acid, or potassium bicarbonate and citric acid, or the like). The pellet can be in tablet or rod form protected by an erodible, disintegrable, or degradable material that is preferably tissue-compatible and degrades into non-toxic products or that slowly hydrolyzes and/or dissolves similarly to the plugs and patches described above (e.g., poly(lactic-co-glycolic acid) (PLGA), polyvinyl alcohol (PVOH), polylactic acid (PLA), poly-L-lactic acid PLAA, Pullulan, Polyethylene Glycol, polyanhydrides, polyorthoesters, polyaryletherketones (PEEK), multi-block polyetheresters, poliglecaprone, polydioxanone, polytrimethylene carbonate, and other like materials). Degradation/erosion of the plug initiates the reaction of the two chemicals in the pellet and subsequently leads to formation of gas (e.g., $CO_2$). As sufficient gas is trapped or built up, sufficient gas is eventually generated to push out the softened polymer material and create a larger channel for the $CO_2$ gas in the balloon to escape. External pressure applied by the stomach to the balloon (e.g., squeezing) can contribute to the process of creating a larger channel. Dimensions and properties of the plug (diameter, thickness, composition, molecular weight, etc.) comprised of the polymer drives the timing of degradation.

In other embodiments, plugs or patches of different shapes or sizes similar to those of the plugs described above can be employed within the balloon lumen in a multi-layer configuration including a semi-permeable membrane to facilitate balloon deflation. The plug or patch is made of similar degradable/erodible/dissolvable material as described above (e.g., poly(lactic-co-glycolic acid) (PLGA), polyvinyl alcohol (PVOH), polylactic acid (PLA), PLAA, pullulan, and other like materials) and contains a compartment enclosed by a semi-permeable membrane (impermeable to an osmolyte) that contains a concentrated solution of a solute or osmolyte (such as glucose, sucrose, other sugars, salts, or combination thereof). Once the plug or patch begins to degrade or erode, the water molecules move by osmosis down the water gradient from the region of greater water concentration to the region of lower water concentration across the semi-permeable membrane into the hypertonic solution in the compartment. The compartment containing the osmolyte swells and eventually bursts, pushing the membranes and the degraded plug or patch out, thereby allowing rapid gas loss through the newly created channels or areas.

Another mechanism for self-deflation is to create a forced de-lamination scheme, which can provide a larger surface area to ensure rapid deflation. In, e.g., a balloon having a tri-layer wall, the outermost layer is substantially strong enough to hold $CO_2$ (e.g., polyethylene terephthalate (PET) or the like), the middle layer is comprised entirely of an erodible material (e.g., PVOH or the like) while the inner layer is comprised of a weaker material (e.g., polyethylene (PE) or the like). The PET or outermost layer is "scored" or hatched with erodible material to create small channels that erode over time. This creates channels such that the gastric fluid seeps into the balloon layers and starts degrading the fully erodible material. When the erodible layer degrades or dissolves, the material that composes the innermost layer also erodes, degrades or dissolves since it is not strong enough to withstand the gastric forces/environment on its own. The balloon then collapses on itself and eventually passes through the lower gastrointestinal tract. Having an erodible layer sandwiched between a strong and weak layer facilitates timing of erosion by creating a longer path length than an erodible plug or patch affected by the gastric environment. The distance between scores or openings can also be selected so as to provide a desired deflation rate.

A mechanism to facilitate passing involves an erosion mechanism that allows for the balloon to be broken down into a size that has a higher probability of predictably passing through the lower gastrointestinal system. Preferably, the size of the balloon as deflated is less than 5 cm long and 2 cm thick (similar to various foreign objects of similar size that have been shown to pass predictably and easily through the pyloric sphincter). This can be accomplished by providing the balloon with "erodible seams". One seam that breaks the balloon open into (at a minimum) two halves, or more seams are provided so that a plurality of smaller balloon pieces is produced in the dissociation reaction. The number of seams used can be selected based on the original surface area of the balloon and what is required to dissociate the balloon into pieces that are of a size that can predictably pass through the gastrointestinal tract more easily. The rate of seam erosion can be controlled by using a material affected by, e.g., the external gastric environment pH, liquid, humidity, temperature, or a combination thereof. Seams can be single layer consisting of only erodible material, or multi-layer. The timing of self-deflation can be further controlled by the design of the seam layers, e.g., making the reaction and/or degradation of the seam material dependent on the internal environment of the balloon instead of the external environment. By manipulating the reaction such that erosion or degradation is initiated by the internal environment (e.g., the balloon's internal pH, humidity, or other factors), any impact of person-to-person gastric variability (pH, etc.) that could affect erosion timing is minimized. The internal balloon environment can be manipulated by adding excess water at injection to create a more humid internal environment, or the amount of constituents added can be varied to manipulate the pH, etc.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

All references cited herein are incorporated herein by reference in their entirety. To the extent publications and patents or patent applications incorporated by reference contradict the disclosure contained in the specification, the specification is intended to supersede and/or take precedence over any such contradictory material.

To the extent publications and patents or patent applications incorporated by reference herein contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A swallowable, self-inflating intragastric balloon system comprising:

a balloon comprising a self-sealing valve system attached to a wall of the balloon in a central lumen of the balloon by an adhesive with a shear force greater than about 40 N, the self-sealing valve system comprising a septum, a retaining structure, and a continuous ring, wherein the septum has a durometer that is less than a durometer of the retaining structure, wherein the continuous ring is configured to exert a compressive force on the septum, wherein the balloon has a weight of less than about 15 g, wherein the balloon is configured to have a shape upon full inflation selected from the group consisting of ellipsoid, spheroid, and oblate spheroid, and wherein the balloon is configured to have a volume of from about 90 cm$^3$ to about 350 cm$^3$ upon full inflation;

an inner container within the central lumen of the balloon, the inner container containing from about 0.28 grams to about 4 grams of an inflation agent, wherein up to about 80 wt. % of a total amount of the inflation agent is powdered citric acid, with a remainder of the inflation agent comprising powdered sodium bicarbonate; and an outer container configured to be swallowed by a patient without assistance, the outer container comprising a material and a structure configured to control timing of inflation, and containing the inner container and the balloon in a compacted state.

2. The system of claim 1, wherein the retaining structure comprises a material selected from the group consisting of silicone, rubber, acrylic, epoxy, a thermoplastic elastomer, and a thermoplastic polyurethane.

3. The system of claim 1, further comprising an inoculation spacer situated in the central lumen of the balloon adjacent to the septum.

4. The system of claim 3, wherein the activation agent comprises an aqueous solution of up to about 50% citric acid in solution into the central lumen of the balloon, and wherein a total amount of citric acid in the inflation agent and the activation agent combined creates a pH of about 6 or less in a residual liquid remaining after completion of a $CO_2$ generating reaction of the inflation agent.

5. The system of claim 3, wherein the inoculation spacer is in a form of a tube or a cylinder.

6. The system of claim 1, wherein the balloon is situated in the outer container in a deflated and folded state, wherein folds of the balloon are configured to localize an activation agent injected into the central lumen of the balloon adjacent to the inner container.

7. The system of claim 6, further comprising a void space in the outer container configured for occupation by activation agent injected inside the central lumen of the balloon, wherein a volume of the void space is from about 0.3 ml to about 4.5 ml.

8. The system of claim 1, wherein the septum has a durometer of about 20 Shore A to about 60 Shore D, and wherein the retaining structure has a durometer of from about 40 Shore D to about 70 Shore D.

9. The system of claim 1, wherein the continuous ring is radio-opaque.

10. The system of claim 1, wherein the balloon is configured to have, upon full inflation, an internal nominal pressure at about 37° C. of from about 0 Pa to about 103421 Pa.

11. The system of claim 1, wherein the balloon is configured to have, upon full inflation, a nominal radius of from about 2.5 cm to about 7.6 cm, a nominal height of from about 0.6 cm to about 7.6 cm.

12. The system of claim 1, wherein from about 10 wt. % to about 80 wt. % of the total amount of the inflation agent is powdered citric acid.

13. The system of claim 1, wherein the inner container has a longest dimension of from about 1.9 cm to 2.7 cm, a width of from about 0.6 cm to about 1 cm, and a volume of from about 0.41 ml to about 1.37 ml.

14. The system of claim 1, wherein the outer container has a longest dimension of from about 2.4 cm to 6.3 cm, a width of from about 0.9 cm to about 2.4 cm, and a volume of from about 1.2 ml to about 8.25 ml.

15. The system of claim 14, wherein at least one of the inner container or the outer container comprises gelatin.

16. The system of claim 15, wherein at least one of the inner container or the outer container comprises a gelatin capsule.

17. The system of claim 1, wherein the balloon is fully sealed 360 degrees around with no external opening or orifice to the central lumen.

18. The system of claim 1, wherein the balloon has a smooth surface.

19. A method for fabricating a swallowable, self-inflating intragastric balloon system, the method comprising:

adhering a self-sealing valve system to a first half of a wall of a balloon by an adhesive with a shear force greater than about 40 N, the self-sealing valve system comprising a septum, a retaining structure, and a continuous ring, wherein the septum has a durometer that is less than a durometer of the retaining structure, wherein the continuous ring is configured to exert a compressive force on the septum;

joining the first half of the wall of the balloon to a second half of the wall of the balloon, wherein either the first half of the wall of the balloon or the second half of the wall of a balloon comprises a hole having a smallest dimension of at least about 0.6 cm, and a largest dimension of no more than about 3.8 cm;

inverting the balloon through the hole;

placing an inner container within a central lumen of the inverted balloon, the inner container containing from about 0.28 grams to about 4 grams of an inflation agent, wherein up to about 80 wt. % of a total amount of the inflation agent is powdered citric acid, with a remainder of the inflation agent comprising powdered sodium bicarbonate; and applying a patch of a material to seal the hole, whereby a balloon having a smooth outer surface is obtained, wherein the balloon has a weight of less than about 15 g, wherein the balloon is configured have a shape upon full inflation selected from the group consisting of ellipsoid, spheroid, and oblate spheroid, and wherein the balloon is configured to have a volume of from about 90 cm$^3$ to about 350 cm$^3$ upon full inflation.

20. The method of claim 19, wherein joining comprises welding or adhesively adhering.

21. A method for inflating a swallowable, self-inflating intragastric balloon, comprising:

a balloon comprising a self-sealing valve system attached to a wall of the balloon in a central lumen of the balloon by an adhesive with a shear force greater than about 40 N, the self-sealing valve system comprising a septum, a retaining structure, and a continuous ring, wherein the septum has a durometer that is less than a durometer of the retaining structure, wherein the continuous ring is configured to exert a compressive force on the septum, wherein the balloon has a weight of less than about 15 g, wherein the balloon is configured have a shape upon full inflation selected from the group consisting of ellipsoid, spheroid, and oblate spheroid, and wherein the balloon is configured to have a volume of from about 90 cm$^3$ to about 350 cm$^3$ upon full inflation;

an inner container within the central lumen of the balloon, the inner container containing from about 0.28 grams to about 4 grams of an inflation agent, wherein up to about 80 wt. % of a total amount of the inflation agent is powdered citric acid, with a remainder of the inflation agent comprising powdered sodium bicarbonate;

an outer container configured to be swallowed by a patient without assistance, the outer container comprising a material and a structure configured to control timing of inflation, and containing the inner container and the balloon in a compacted state; and an inoculation spacer configured to guide a needle into the septum for injection of an activation agent into the central lumen of the balloon while avoiding puncture of the inner container, wherein the inoculation spacer is situated in the outer container, adjacent to the septum;

injecting an activation agent into the central lumen of the balloon through the wall of the balloon atop the septum and through the septum itself using the inoculation spacer as a guide, whereby degradation of the inner container is initiated; thereafter allowing the system to be swallowed by a patient in need thereof;

degrading the outer container in a stomach of the patient;

initiating inflation by contact of the activation agent with the inflation agent via degradation of the inner container, wherein inflation is initiated no earlier than about 30 seconds after injection of the activation agent;

unfolding the balloon via inflation from about 60 seconds to about 15 minutes after injection of activation agent; and inflating the balloon such that at least about 10% of the occupyable volume of the balloon is filled within about 30 minutes, at least about 60% of the occupyable volume of the balloon is filled within about 12 hours, and at least about 90% of the occupyable volume of the balloon is filled within about 24 hours.

22. The method of claim 21, wherein the activation agent is substantially localized in the balloon adjacent to the inner container upon injection.

23. The method of claim 21, wherein the balloon is compacted such that, upon initiating inflation, the balloon unfolds in a manner that creates a surface area sufficiently large so as to prohibit the balloon from passing through the pyloric sphincter.

24. The method of claim 21, wherein a pH of any remnant liquid inside the central lumen of the balloon is acidic such that any balloon leakage or breach that allows stomach acid to enter the balloon does not initiate reinflation of the balloon.

25. The method of claim 21, wherein allowing the system to be swallowed by a patient in need thereof comprises swallowing, via normal peristalsis, the outer container containing the inner container, inoculation spacer, and the balloon in a compacted state.

26. The method of claim 21, wherein the inner container comprises a gelatin capsule.

* * * * *